(12) United States Patent
Orme et al.

(10) Patent No.: US 6,649,631 B1
(45) Date of Patent: Nov. 18, 2003

(54) COMPOSITIONS AND METHODS FOR TREATING BONE DEFICIT CONDITIONS

(75) Inventors: Mark W. Orme, Seattle, WA (US); Nand Baindur, Edmonds, WA (US); Kirk G. Robbins, Rendon, WA (US); Scott M. Harris, Seattle, WA (US); Maria Kontoyianni, Seattle, WA (US); Laurence H. Hurley, Austin, TX (US); Sean M. Kerwin, Round Rock, TX (US); Gregory Mundy, San Antonio, TX (US); Charles Petrie, Woodinville, WA (US)

(73) Assignees: The Board of Regents of the University of Texas System, Austin, TX (US); ZymoGenetics Corporation, Seattle, WA (US); OsteoScreen, San Antonio, TX (US)

( * ) Notice: Subject to any disclaimer, the term of this patent is extended or adjusted under 35 U.S.C. 154(b) by 0 days.

(21) Appl. No.: 09/297,188
(22) PCT Filed: Oct. 23, 1997
(86) PCT No.: PCT/US97/18864
§ 371 (c)(1), (2), (4) Date: Nov. 19, 1999
(87) PCT Pub. No.: WO98/17267
PCT Pub. Date: Apr. 30, 1998

(51) Int. Cl.[7] ............................................. A61K 31/44
(52) U.S. Cl. ...................... 514/332; 514/334; 514/255; 514/275; 514/256; 514/242; 514/245
(58) Field of Search ................................ 514/332, 334, 514/255, 275, 256, 242, 245

(56) References Cited

U.S. PATENT DOCUMENTS

| | | |
|---|---|---|
| 4,761,471 A | 8/1988 | Urist .......................... 530/840 |
| 5,280,040 A | 1/1994 | Labroo et al. .............. 514/442 |
| 5,393,306 A | 2/1995 | Tzikas et al. .................. 8/639 |
| 5,441,964 A | 8/1995 | Bryant et al. ............... 514/324 |
| 5,523,309 A | 6/1996 | Bryant et al. ............... 514/320 |
| 5,622,974 A | 4/1997 | Muehl ........................ 514/320 |

FOREIGN PATENT DOCUMENTS

| | | |
|---|---|---|
| EP | 3938561 | 5/1991 |
| GB | 1161492 | 8/1969 |
| WO | WO90/11366 | 10/1990 |
| WO | WO92/03125 | 3/1992 |
| WO | WO93/10113 | 5/1993 |
| WO | WO93/20859 | 10/1993 |
| WO | WO95/10513 | 4/1995 |
| WO | WO95/24211 | 9/1995 |
| WO | WO96/38590 | 12/1996 |
| WO | WO97/15308 | 5/1997 |

OTHER PUBLICATIONS

"27–Heterocycles," Chemical Abstracts, (1991) 115(1)(Abstract No. 115:8533):833.

"28–Heterocycles Compounds (More than One Hetero Atom)," Chemical Abstracts, (1997) 127(2)(Abstract No. 127:17703)566.

"2–Mammalian Hormones," Chemical Abstracts, (1988) 108(9)(Abstract No. 108:69162):97.

Alberti, G., et al., *Ricerche Sui Coloranti Cationici per Fibra Acrilica*, La Chimica E L'Industria, (1974) 56(7):495–97.

Ayyangar, N.R., et al., *Polycyclic Compounds Part VI Structural Features of C.I. Disperse Yellow 232*, Dyes and Pigments, (1990) 13:301–10.

Hagen, V. et al., "Synthese and Analgetische Wirkung Von 2–Aryliminomethylchinolinen," Die Pharmazie, (1983) 38:437–39 (No English Translation Included).

Harris, S.E., et al., "Effects of Transforming Growth Factor β on Bone Nodule Formation and Expression of Bone Morphogenetic Protein 2, Osteocalcin, Osteopontin, Phosphatase, and Type I Collagen mRNA in Long–Term Cultures of Fetal Rat Calvarial Osteoblasts," J. of Bone and Mineral Research, (1994) 9(6):855–863.

Irving, H.M.N.H. et al., "Studies with Dithizone Part XXI. A Novel Bicyclic Oxidation Product of Dithizone," Anal. Chim. Acta, (1970) 49:261–266.

Jordan, V.C., et al., "Effects of Anti–Estrogens on Bone in Castrated and Intact Female Rats," Breast Cancer Res. Treat., 1987, 10: 31–5.

Kandeel, M.M., "Synthesis of 4'–Nitrophenyl–2–Aminobenzthiazol–6–YL Sulfides and 4'–Nitrophenyl–2–Aminobenthiazol–6–YL Sulfones Containing Dithiocarbamate," Phosphorus, Sulfur, Silicon, (1990) 48:149–55.

Kaneko, C., et al., "Nucleophilic Substitution Reactions of 2–Chloropyridine with Polymethylenediols Using Phase–Transfer Catalysis: Selective Formation of Mono–or Diethers," Synthesis, (1982) 5:465–66.

Kawato, T., et al., "Selectivity of Nucleophilic Substitution on 3–Substituted 2,6–Dichloropyridines with Alkoxide. Pyridinophane Preparation," Heterocycles, (1990) 31(6):1097–104.

(List continued on next page.)

Primary Examiner—Jane Fan
(74) Attorney, Agent, or Firm—Morrison & Foerster, LLP

(57) ABSTRACT

Compounds containing two aromatic systems covalently linked through a linker containing one or more atoms, or "linker" defined as including a covalent bond per se so as to space the aromatic systems at a distance 1.5–15 Å, are effective in treating conditions associated with bone deficits. The compounds can be administered to vertebrate subjects alone or in combination with additional agents that promote bone growth or that inhibit bone resorption. They can be screened for activity prior to administration by assessing their ability to effect the transcription of a reporter gene coupled to a promoter associated with a bone morphogenetic protein and/or their ability to stimulate calvarial growth in model animal systems.

6 Claims, 177 Drawing Sheets

OTHER PUBLICATIONS

Kim, S., et al., "Preparation of Multivesicular Liposomes," Biochimica Biophysica Acta, (1983) 728:339:348.

Kimmel, D.B., et al., "The Effect of Recombinant Human (1–84) or Synthetic Human (1–34) Parathyroid Hormone on the Skeleton of Adult Osteopenic Ovariectomized Rats," Endocrinology, (1993) 132(4):1577–84.

Ksander, G.A., et al., "Exogenous Transforming Growth Factor–Beta 2 Enhances Connective Tissue Formation and Wound Strength in Guinea Pig Dermal Wounds Healing by Secondary Intent," Ann. Surg., (1990) 211(3):288–94.

Laval–Jeantet, A.–M., et al., "Dual–Energy X–Ray Absorptiometry of the Calcaneus: Comparison with Vertebral Dual–Energy X–Ray Absorptiometry and Quantitative Computed Tomography," Calcif. Tissue Intl., (1995) 56:14–8.

Leserman, L.D., et al., "Targeting to Cells of Fluorescent Liposomes Covalently Coupled with Monoclonal Antibody or Protein A," Nature, (1980) 288:602–604.

Lugovkin, B. P.; Zh Obshch Khim (1972) 42:966–69 (No English Translation Included).

Mayer, L.D., et al., "Vesicles of Variable Sizes Produced by a Rapid Extrusion Procedure," Biochimica et Biophysica Acta, (1986) 858:161–8.

McDonald, W. S., et al., "An Unusual Bicyclic Oxidation Product of Dithizone," Chemical Communications, (1969) 392–3.

Morimoto, T., et al., "Decarboxylation Reactions. VI. Reactions of α–Arylmethyleneamino–Sustituted Derivatives of Pyridine, Quinoline, and Isoquinoline with Trichloroacetic Anhydride," Chem. Pharm. Bull., (1977) 25(7):1607–9.

Mundy, G.R., "Cytokines and Growth Factors in the Regulation of Bone Remodeling," J. Bone and Mineral Research, (1993) 8(Supplement 2):S505–S510.

Mundy, G.R., "Regulation of Bone Formation by Bone Morphogenetic Proteins–and Other Growth Factors," Clinical Orthopaedics and Related Research, (1996) 324:24–8.

Olson, F., et al., "Preparation of Liposomes of Defined Size Distribution by Extrusion through Polycarbonate Membranes," Biochimica et Biophysica Acta, (1979) 557:9–23.

Renault, J., et al., "Chimie Organique," C. R. Acad. SC. Paris, Serie C (1975) 280:1041–43.

Salem, M.A.I., et al., "Synthesis of Some New 2–[2–(Chlorobenzoyl) Vinyl]–4H–3, 1–Quinazolin–4–one Derivatives," Egypt J. Chem., (1984) 27(6):779–87.

Sampath, T.K., et al., "Isolation of Osteogenin, an Extracellular Matrix–Associated, Bone–Inductive Protein, by Heparin Affinity Chromatography, "4Proc. Natl. Acad. Sci. USA, (1987)84:7109–13.

Schwarz, W., et al., "Potentielle Antiöstrogene Vom Typ des 1,2–Diphenyl–1–but–1–ens," Arch. Pharm., (1991) 324(4):223–9.

Stein, G.S., et al., "Bone Cell Differentiation: A Functionally Coupled Relationship Between Expression of Cell–Growth–and Tissue–Specific Genes," Current Opinion in Cell Biology (1990) 2:1018–27.

Szoka, F., et al., "Procedure for Preparation of Liposomes with Large Internal Aqueous Space and High Capture by Reverse–Phase Evaporation," Proc. Natl. Acad. Sci. USA, (1978) 75(9):4194–8.

Tencer, A.F., et al., "The Effect of Local Controlled Release of Sodium Fluoride on the Stimulation of Bone Growth," J. Biomed. Mat. Res., (1989) 23: 571–89.

Urist, M.R., "Bone: Formation by Autoinduction," Science, (1965) 150:893–9.

Watts, C.K.W., et al., Studies on the Ligand Specificity and Potential Identify of Microsomal Antiestrogen–Binding Sites, Mol. Pharmacol., 1987, 31:541–51.

Wozney, J.M., "The Bone Morphogenetic Protein Family and Osteogenesis," Molecular Reproduction and Development (1992) 32:160–7.

Wozney, J.M., et al., "Novel Regulators of Bone Formation: Molecular Clones and Activities," Science (1988) 242:1528–1534.

Zamboni, R., et al., "Development of a Novel Series of Styrylquinoline Compounds as High–Affinity Leukotriene $D_4$ Receptor Antagonists: Synthetic and Structure–Activity Studies Leading to the Discovery of (±)–3–[[[3–[2–(7–Chloro–2–quinolinyl)–(E)–ethenyl]phenyl] [[3–(dimethylamino)–3–oxopropyl]thio]methyl]thio]propionic Acid," J. Med. Chem., (1992) 35:3832–44.

| Ar¹–linker – Ar² 1.5–15A | | (I) |
|---|---|---|
| Ar¹ | Ar² | |
| contains 5-membered heterocycle | substituted or unsubsituted benzene | II-A |
| contains 5-membered heterocycle | substituted or unsubstituted naphthalene | II-B |
| contains 5-membered heterocycle | contains 6-membered heterocycle | II-C |
| contains 5-membered heterocycle | contains 5-membered heterocycle | II-D |
| contains 6-membered heterocycle | substituted or unsubstituted benzene | II-E |
| contains 6-membered heterocycle | substituted or unsubstituted naphthalene | II-F |
| contains 6-membered heterocycle | contains 6-membered heterocycle | II-G |
| substituted or unsubstituted naphthalene | substituted or unsubstituted benzene | II-H |
| substituted or unsubstituted naphthalene | substituted or unsubstituted naphthalene | II-I |
| substituted or unsubstituted benzene | substituted or unsubstituted benzene | II-J |

FIG. 1

| NNC# | MOL.WEIGHT | CONCENTRATION | | %RESPONSE | |
|---|---|---|---|---|---|
| 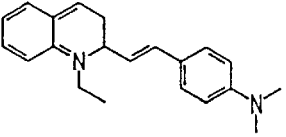 | | | | | |
| 50-0194 | 430.33 | | | | |
| 50-0194 | | 100.00 | uM | -19.190 | |
| | | 31.25 | uM | 32.450 | |
| | | 9.77 | uM | -14.240 | |
| | | 3.05 | uM | -11.330 | |
| | | 953.67 | nM | -12.790 | |
| | | 298.02 | nM | -13.450 | |
| | | 93.13 | nM | -12.290 | |
| | | 29.10 | nM | -9.440 | |
| | | 9.09 | nM | -6.450 | |
| | | 2.84 | nM | -8.130 | |
| | | 888.18 | pM | -3.320 | |
| 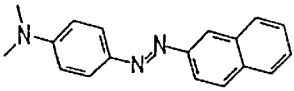 | | | | | |
| 50-0195 | 275.36 | | | | |
| 50-0195 | | 100.00 | uM | -4.630 | |
| | | 31.25 | uM | 16.790 | |
| | | 9.77 | uM | 62.830 | |
| | | 3.05 | uM | 102.720 | |
| | | 953.67 | nM | 60.860 | |
| | | 298.02 | nM | 32.450 | |
| | | 93.13 | nM | 19.340 | |
| | | 29.10 | nM | 17.220 | |
| | | 9.09 | nM | 5.640 | |
| | | 2.84 | nM | 4.840 | |
| | | 888.18 | pM | 5.640 | |
| 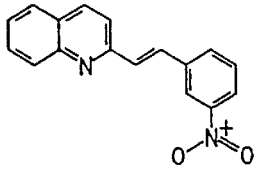 | | | | | |
| 50-0196 | 276.30 | | | | |
| 50-0196 | | 100.00 | uM | -16.210 | |
| | | 31.25 | uM | -8.560 | |
| | | 9.77 | uM | 11.620 | |
| | | 3.05 | uM | 27.790 | |
| | | 953.67 | nM | 18.390 | |
| | | 298.02 | nM | 6.230 | |
| | | 93.13 | nM | 12.420 | |
| | | 29.10 | nM | 12.630 | |
| | | 9.09 | nM | 6.590 | |
| | | 2.84 | nM | 7.970 | |
| | | 888.18 | pM | 5.060 | |
FIG. 3

| NNC# | MOL.WEIGHT | CONCENTRATION | | %RESPONSE |
|---|---|---|---|---|
| 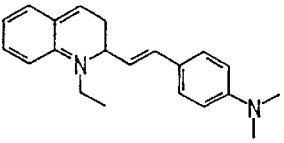 50-0194 | 430.33 | | | |
| 50-0194 | | 100.00 | uM | -19.190 |
| | | 31.25 | uM | 32.450 |
| | | 9.77 | uM | -14.240 |
| | | 3.05 | uM | -11.330 |
| | | 953.67 | nM | -12.790 |
| | | 298.02 | nM | -13.450 |
| | | 93.13 | nM | -12.290 |
| | | 29.10 | nM | -9.440 |
| | | 9.09 | nM | -6.450 |
| | | 2.84 | nM | -8.130 |
| | | 888.18 | pM | -3.320 |
| 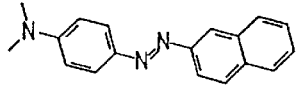 50-0195 | 275.36 | | | |
| 50-0195 | | 100.00 | uM | -4.630 |
| | | 31.25 | uM | 16.790 |
| | | 9.77 | uM | 62.830 |
| | | 3.05 | uM | 102.720 |
| | | 953.67 | nM | 60.860 |
| | | 298.02 | nM | 32.450 |
| | | 93.13 | nM | 19.340 |
| | | 29.10 | nM | 17.220 |
| | | 9.09 | nM | 5.640 |
| | | 2.84 | nM | 4.840 |
| | | 888.18 | pM | 5.640 |
| 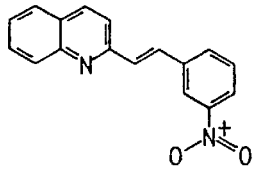 50-0196 | 276.30 | | | |
| 50-0196 | | 100.00 | uM | -16.210 |
| | | 31.25 | uM | -8.560 |
| | | 9.77 | uM | 11.620 |
| | | 3.05 | uM | 27.790 |
| | | 953.67 | nM | 18.390 |
| | | 298.02 | nM | 6.230 |
| | | 93.13 | nM | 12.420 |
| | | 29.10 | nM | 12.630 |
| | | 9.09 | nM | 6.590 |
| | | 2.84 | nM | 7.970 |
| | | 888.18 | pM | 5.060 |
FIG. 3A

| | | | | | |
|---|---|---|---|---|---|
|  50-0197 | 274.37 | | | | |
| 50-0197 | | 100.00 | uM | -18.250 | |
| | | 31.25 | uM | -14.980 | |
| | | 9.77 | uM | 4.040 | |
| | | 3.05 | uM | 93.790 | |
| | | 953.67 | nM | 205.530 | |
| | | 298.02 | nM | 242.920 | |
| | | 93.13 | nM | 195.890 | |
| | | 29.10 | nM | 115.320 | |
| | | 9.09 | nM | 85.630 | |
| | | 2.84 | nM | 54.380 | |
| | | 888.18 | pM | 33.180 | |
|  59-0008 | 254.32 | | | | |
| 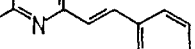 59-0019 | 59-0019 | | | | |
| 59-0019 | | 100.00 | uM | -22.240 | |
| | | 31.25 | uM | -22.670 | |
| | | 9.77 | uM | -17.470 | |
| | | 3.05 | uM | 74.490 | |
| | | 953.67 | nM | 198.080 | |
| | | 298.02 | nM | 258.340 | |
| | | 93.13 | nM | 225.350 | |
| | | 29.10 | nM | 75.220 | |
| | | 9.09 | nM | 24.030 | |
| | | 2.84 | nM | 34.480 | |
| | | 888.18 | pM | -3.740 | |
| 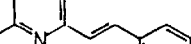 59-0020 | 266.73 | | | | |
| 59-0020 | | 100.00 | uM | -16.510 | |
| | | 31.25 | uM | -16.040 | |
| | | 9.77 | uM | -0.270 | |
| | | 3.05 | uM | 96.490 | |
| | | 953.67 | nM | 153.320 | |
| | | 298.02 | nM | 110.240 | |
| | | 93.13 | nM | 60.030 | |
FIG. 3B

| | | 29.10 | nM | 37.870 | |
|---|---|---|---|---|---|
| | | 9.09 | nM | 24.820 | |
| | | 2.84 | nM | 20.500 | |
| | | 888.18 | pM | 13.310 | |

FIG. 3C

| | | | | | |
|---|---|---|---|---|---|
| 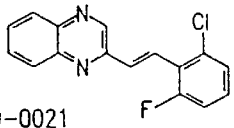 59-0021 | 284.72 | | | | |
| 59-0021 | | 100.00 | uM | −16.310 | |
| | | 31.25 | uM | −12.850 | |
| | | 9.77 | uM | 84.130 | |
| | | 3.05 | uM | 89.940 | |
| | | 953.67 | nM | 65.750 | |
| | | 298.02 | nM | 33.940 | |
| | | 93.13 | nM | 22.560 | |
| | | 29.10 | nM | 25.020 | |
| | | 9.09 | nM | 13.910 | |
| | | 2.84 | nM | 33.270 | |
| | | 888.18 | pM | 15.500 | |
| 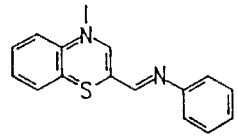 59-0022 | 266.37 | | | | |
| 59-0022 | | 100.00 | uM | 7.250 | |
| | | 31.25 | uM | −2.070 | |
| | | 9.77 | uM | −0.270 | |
| | | 3.05 | uM | 4.390 | |
| | | 953.67 | nM | 3.060 | |
| | | 298.02 | nM | −1.800 | |
| | | 93.13 | nM | −0.200 | |
| | | 29.10 | nM | −3.270 | |
| | | 9.09 | nM | 1.130 | |
| | | 2.84 | nM | 2.590 | |
| | | 888.18 | pM | 2.460 | |
| 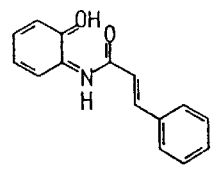 59-0023 | 239.28 | | | | |
| 59-0023 | | 100.00 | uM | −12.720 | |
| | | 31.25 | uM | 33.140 | |
| | | 9.77 | uM | 56.500 | |
| | | 3.05 | uM | 29.550 | |
| | | 953.67 | nM | 25.360 | |
| | | 298.02 | nM | 15.700 | |
| | | 93.13 | nM | 7.380 | |
| | | 29.10 | nM | 9.710 | |
| | | 9.09 | nM | 1.000 | |
| | | 2.84 | nM | 4.520 | |
| | | 888.18 | pM | −0.010 | |
FIG. 3D

| | | | | | |
|---|---|---|---|---|---|
| 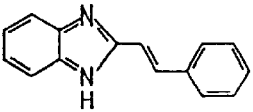 59-0024 | 220.28 | | | | |
| 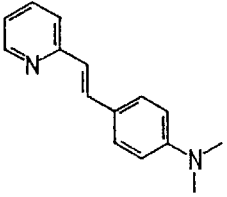 59-0025 | 224.31 | | | | |
| 59-0025 | | 100.00 | uM | -25.590 | |
| | | 31.25 | uM | 14.150 | |
| | | 9.77 | uM | 50.690 | |
| | | 3.05 | uM | 57.880 | |
| | | 953.67 | nM | 38.900 | |
| | | 298.02 | nM | 28.530 | |
| | | 93.13 | nM | 19.660 | |
| | | 29.10 | nM | 17.490 | |
| | | 9.09 | nM | -0.600 | |
| | | 2.84 | nM | -4.190 | |
| | | 888.18 | pM | 4.670 | |
| 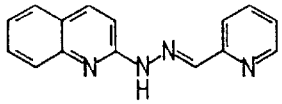 59-0026 | 248.29 | | | | |
| 59-0026 | | 100.00 | uM | -29.830 | |
| | | 31.25 | uM | -9.440 | |
| | | 9.77 | uM | -10.470 | |
| | | 3.05 | uM | 46.220 | |
| | | 953.67 | nM | 107.760 | |
| | | 298.02 | nM | 86.720 | |
| | | 93.13 | nM | 36.850 | |
| | | 29.10 | nM | 26.720 | |
| | | 9.09 | nM | 8.520 | |
| | | 2.84 | nM | -1.240 | |
| | | 888.18 | pM | 4.020 | |
FIG. 3E

| | | | | |
|---|---|---|---|---|
|  59-0027 | 250.30 | | | |
| 59-0027 | | 100.00 | uM | 89.810 |
| | | 31.25 | uM | 54.670 |
| | | 9.77 | uM | 44.940 |
| | | 3.05 | uM | 23.780 |
| | | 953.67 | nM | 8.380 |
| | | 298.02 | nM | 6.330 |
| | | 93.13 | nM | 7.360 |
| | | 29.10 | nM | 3.380 |
| | | 9.09 | nM | -1.620 |
| | | 2.84 | nM | -3.670 |
| | | 888.18 | pM | -0.720 |
| 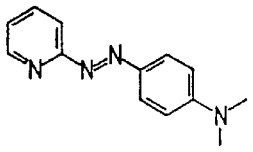 59-0028 | 226.28 | | | |
| 59-0028 | | 100.00 | uM | -26.750 |
| | | 31.25 | uM | -16.740 |
| | | 9.77 | uM | 29.550 |
| | | 3.05 | uM | 100.580 |
| | | 953.67 | nM | 54.940 |
| | | 298.02 | nM | 31.340 |
| | | 93.13 | nM | 7.500 |
| | | 29.10 | nM | 7.500 |
| | | 9.09 | nM | 7.880 |
| | | 2.84 | nM | 3.140 |
| | | 888.18 | pM | 4.670 |
FIG. 3F

| | | | | |
|---|---|---|---|---|
| 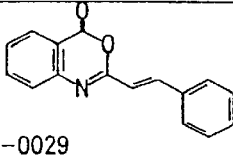 | | | | |
| 59-0029 | 249.27 | | | |
| 59-0029 | | 100.00 | uM | -15.160 |
| | | 31.25 | uM | 41.940 |
| | | 9.77 | uM | 36.630 |
| | | 3.05 | uM | 7.120 |
| | | 953.67 | nM | 21.880 |
| | | 298.02 | nM | 15.540 |
| | | 93.13 | nM | 1.810 |
| | | 29.10 | nM | 1.370 |
| | | 9.09 | nM | 12.140 |
| | | 2.84 | nM | -4.230 |
| | | 888.18 | pM | 9.040 |
| 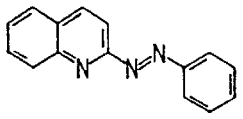 | | | | |
| 59-0030A | 233.28 | | | |
| 59-0030A | | 100.00 | uM | -27.970 |
| | | 31.25 | uM | -22.830 |
| | | 9.77 | uM | -5.420 |
| | | 3.05 | uM | 57.280 |
| | | 953.67 | nM | 72.620 |
| | | 298.02 | nM | 53.000 |
| | | 93.13 | nM | 29.990 |
| | | 29.10 | nM | 14.630 |
| | | 9.09 | nM | 3.870 |
| | | 2.84 | nM | 6.970 |
| | | 888.18 | pM | 1.810 |
|  | | | | |
| 59-0031 | 231.30 | | | |
| 59-0031 | | 100.00 | uM | -25.790 |
| | | 31.25 | uM | -17.810 |
| | | 9.77 | uM | 20.840 |
| | | 3.05 | uM | 87.380 |
| | | 953.67 | nM | 49.320 |
| | | 298.02 | nM | 43.110 |
| | | 93.13 | nM | 29.530 |
| | | 29.10 | nM | 1.810 |
| | | 9.09 | nM | 1.220 |
| | | 2.84 | nM | -0.550 |
| | | 888.18 | pM | 4.160 |
FIG. 3G

| | | | | |
|---|---|---|---|---|
| 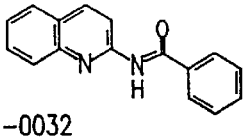 59-0032 | 248.29 | | | |
| 59-0032 | | 100.00 | uM | -7.780 |
| | | 31.25 | uM | 40.750 |
| | | 9.77 | uM | 42.820 |
| | | 3.05 | uM | 25.700 |
| | | 953.67 | nM | 31.170 |
| | | 298.02 | nM | 34.410 |
| | | 93.13 | nM | 3.570 |
| | | 29.10 | nM | 4.320 |
| | | 9.09 | nM | -10.000 |
| | | 2.84 | nM | 5.650 |
| | | 888.18 | pM | 11.990 |
| 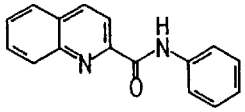 59-0033 | 248.29 | | | |
| 59-0033 | | 100.00 | uM | -28.180 |
| | | 31.25 | uM | -11.590 |
| | | 9.77 | uM | 55.300 |
| | | 3.05 | uM | 49.710 |
| | | 953.67 | nM | 47.410 |
| | | 298.02 | nM | 0.250 |
| | | 93.13 | nM | 7.980 |
| | | 29.10 | nM | -8.940 |
| | | 9.09 | nM | -7.630 |
| | | 2.84 | nM | -0.400 |
| | | 888.18 | pM | -5.980 |
| 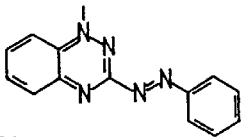 59-0034 | 268.34 | | | |
| 59-0034 | | 100.00 | uM | -28.51 |
| | | 31.25 | uM | 24 |
| | | 9.77 | uM | 73.58 |
| | | 3.05 | uM | 37.91 |
| | | 953.67 | nM | 20.09 |
| | | 298.02 | nM | 16.87 |
| | | 93.13 | nM | 15.23 |
| | | 29.10 | nM | 28.83 |
| | | 9.09 | nM | 9.08 |
| | | 2.84 | nM | 23.02 |
| | | 888.18 | pM | -0.32 |
FIG. 3H

| | | | | |
|---|---|---|---|---|
| 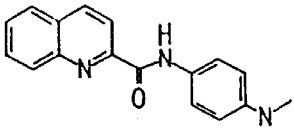 59-0035 | 291.36 | | | |
| 59-0035 | | 100.00 | uM | −14.92 |
| | | 31.25 | uM | 29.17 |
| | | 9.77 | uM | 15.87 |
| | | 3.05 | uM | 18.8 |
| | | 953.67 | nM | 3.88 |
| | | 298.02 | nM | 6.15 |
| | | 93.13 | nM | 3.22 |
| | | 29.10 | nM | −10.03 |
| | | 9.09 | nM | 15.58 |
| | | 2.84 | nM | −3.56 |
| | | 888.18 | pM | −7.13 |
| 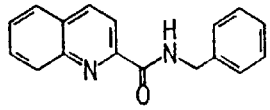 59-0036 | 262.31 | | | |
| 59-0036 | | 100.00 | uM | −0.98 |
| | | 31.25 | uM | −3.25 |
| | | 9.77 | uM | −4.54 |
| | | 3.05 | uM | −1.95 |
| | | 953.67 | nM | 0.32 |
| | | 298.02 | nM | −6.49 |
| | | 93.13 | nM | −17.19 |
| | | 29.10 | nM | −0.66 |
| | | 9.09 | nM | −5.52 |
| | | 2.84 | nM | −9.4 |
| | | 888.18 | pM | −16.53 |
| 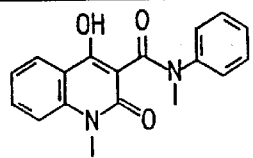 59-0037 | 308.00 | | | |
| 59-0037 | | 100.00 | uM | −10.69 |
| | | 31.25 | uM | −11.99 |
| | | 9.77 | uM | −10.03 |
| | | 3.05 | uM | −19.11 |
| | | 953.67 | nM | −9.4 |
| | | 298.02 | nM | 2.27 |
| | | 93.13 | nM | −2.9 |
| | | 29.10 | nM | −10.69 |
| | | 9.09 | nM | 2.59 |
| | | 2.84 | nM | 0.66 |
| | | 888.18 | pM | −2.59 |
FIG. 31

| | | | | | | |
|---|---|---|---|---|---|---|
| 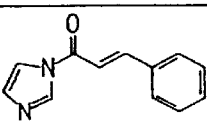 | | | | | | |
| 59-0038 | 291.36 | | | | | |
| 59-0038 | | 100.00 | uM | -23.430 | | |
| | | 31.25 | uM | -8.390 | | |
| | | 9.77 | uM | -0.100 | | |
| | | 3.05 | uM | -2.860 | | |
| | | 953.67 | nM | -2.240 | | |
| | | 298.02 | nM | 3.900 | | |
| | | 93.13 | nM | 6.350 | | |
| | | 29.10 | nM | 1.150 | | |
| | | 9.09 | nM | 6.960 | | |
| | | 2.84 | nM | -4.390 | | |
| | | 888.18 | pM | -0.380 | | |
| 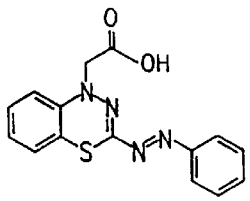 | | | | | | |
| 59-0039 | 312.35 | | | | | |
| 59-0039 | | 100.00 | uM | 14.170 | | |
| | | 31.25 | uM | 7.620 | | |
| | | 9.77 | uM | 1.940 | | |
| | | 3.05 | uM | -3.140 | | |
| | | 953.67 | nM | -7.770 | | |
| | | 298.02 | nM | -5.980 | | |
| | | 93.13 | nM | -8.820 | | |
| | | 29.10 | nM | -2.390 | | |
| | | 9.09 | nM | -16.580 | | |
| | | 2.84 | nM | -4.480 | | |
| | | 888.18 | pM | -0.450 | | |
| 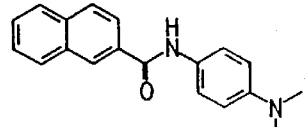 | | | | | | |
| 59-0040 | 290.37 | | | | | |
| 59-0040 | | 100.00 | uM | -20.400 | | |
| | | 31.25 | uM | -17.310 | | |
| | | 9.77 | uM | -8.110 | | |
| | | 3.05 | uM | 32.180 | | |
| | | 953.67 | nM | 36.180 | | |
| | | 298.02 | nM | 17.440 | | |
| | | 93.13 | nM | 2.040 | | |
| | | 29.10 | nM | 10.350 | | |
| | | 9.09 | nM | 6.070 | | |
| | | 2.84 | nM | 6.960 | | |
| | | 888.18 | pM | 13.440 | | |
FIG. 3J

| | | | | |
|---|---|---|---|---|
| 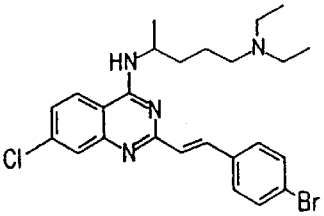 59-0041 | 501.90 | | | |
| 59-0041 | | 100.00 | uM | −18.37 |
| | | 31.25 | uM | −17.33 |
| | | 9.77 | uM | −5.11 |
| | | 3.05 | uM | 3.31 |
| | | 953.67 | nM | −0.77 |
| | | 298.02 | nM | −1.56 |
| | | 93.13 | nM | 3.55 |
| | | 29.10 | nM | −11.24 |
| | | 9.09 | nM | 0.25 |
| | | 2.84 | nM | −0.27 |
| | | 888.18 | pM | 2.02 |
| 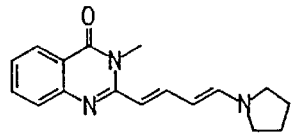 59-0042 | 281.36 | | | |
| 59-0042 | | 100.00 | uM | 163.51 |
| | | 31.25 | uM | −7.67 |
| | | 9.77 | uM | 9.41 |
| | | 3.05 | uM | 0.75 |
| | | 953.67 | nM | 6.11 |
| | | 298.02 | nM | 3.82 |
| | | 93.13 | nM | 2.54 |
| | | 29.10 | nM | 4.07 |
| | | 9.09 | nM | −9.73 |
| | | 2.84 | nM | −0.02 |
| | | 888.18 | pM | 18.37 |
| 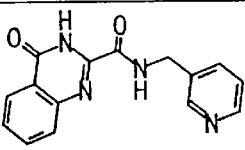 59-0043 | 280.29 | | | |
| 59-0043 | | 100.00 | uM | 20.66 |
| | | 31.25 | uM | 7.4 |
| | | 9.77 | uM | −1.29 |
| | | 3.05 | uM | −2.31 |
| | | 953.67 | nM | 1.54 |
| | | 298.02 | nM | −0.79 |
| | | 93.13 | nM | 1.52 |
| | | 29.10 | nM | 2.79 |
| | | 9.09 | nM | −0.27 |
| | | 2.84 | nM | 8.92 |
| | | 888.18 | pM | −4.34 |
FIG. 3K

| Structure | ID | MW | Conc | Unit | Val1 | Val2 |
|---|---|---|---|---|---|---|
| 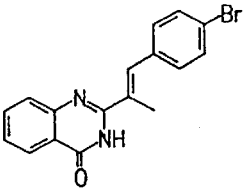 | 59-0044 | 341.21 | | | | |
| | 59-0044 | | 100.00 | uM | 7.38 | |
| | | | 31.25 | uM | 11.72 | |
| | | | 9.77 | uM | 12.49 | |
| | | | 3.05 | uM | -0.52 | |
| | | | 953.67 | nM | 0.5 | |
| | | | 298.02 | nM | 6.11 | |
| | | | 93.13 | nM | -1.54 | |
| | | | 29.10 | nM | 19.14 | |
| | | | 9.09 | nM | 7.13 | |
| | | | 2.84 | nM | -2.06 | |
| | | | 888.18 | pM | 5.84 | |
| 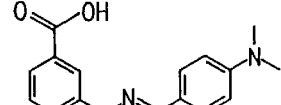 | 59-0045 | 283.33 | | | | |
| | 59-0045 | | 100.00 | uM | 52.37 | 64.460 |
| | | | 31.25 | uM | 148.43 | 192.960 |
| | | | 9.77 | uM | 204.47 | 422.540 |
| | | | 3.05 | uM | 280.3 | 437.020 |
| | | | 953.67 | nM | 254.82 | 410.890 |
| | | | 298.02 | nM | 218.21 | 266.090 |
| | | | 93.13 | nM | 196.98 | 183.730 |
| | | | 29.10 | nM | 96.06 | 80.440 |
| | | | 9.09 | nM | 67.35 | 55.530 |
| | | | 2.84 | nM | 52.99 | 44.160 |
| 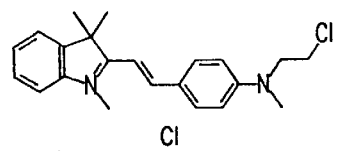 | 59-0046 | 389.37 | | | | |
| | 59-0046 | | 100.00 | uM | 79.33 | |
| | | | 31.25 | uM | 2.24 | |
| | | | 9.77 | uM | -1.67 | |
| | | | 3.05 | uM | -6.18 | |
| | | | 953.67 | nM | 0.001 | |
| | | | 298.02 | nM | -3.63 | |
| | | | 93.13 | nM | -0.84 | |
| | | | 29.10 | nM | -8.42 | |
| | | | 9.09 | nM | 3.92 | |
| | | | 2.84 | nM | 0.3 | |
| | | | 888.18 | pM | 5.61 | |
FIG. 3L

| | | | | | |
|---|---|---|---|---|---|
| 59-0047 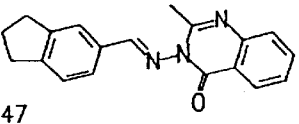 | 303.37 | | | | |
| 59-0047 | | 100.00 | uM | -6.73 | |
| | | 31.25 | uM | 10.38 | |
| | | 9.77 | uM | -6.16 | |
| | | 3.05 | uM | -1.39 | |
| | | 953.67 | nM | -10.11 | |
| | | 298.02 | nM | -4.49 | |
| | | 93.13 | nM | -7.28 | |
| | | 29.10 | nM | -12.34 | |
| | | 9.09 | nM | -3.08 | |
| | | 2.84 | nM | -2.26 | |
| | | 888.18 | pM | -5.34 | |
| 59-0048 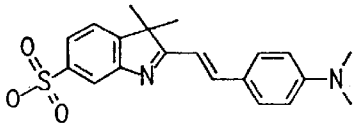 | 384.50 | | | | |
| 59-0048 | | 100.00 | uM | -6.73 | |
| | | 31.25 | uM | 0.27 | |
| | | 9.77 | uM | -5.61 | |
| | | 3.05 | uM | -2.26 | |
| | | 953.67 | nM | -12.89 | |
| | | 298.02 | nM | -1.69 | |
| | | 93.13 | nM | -4.77 | |
| | | 29.10 | nM | -8.14 | |
| | | 9.09 | nM | -3.92 | |
| | | 2.84 | nM | -11.2 | |
| | | 888.18 | pM | -4.77 | |
| 59-0049 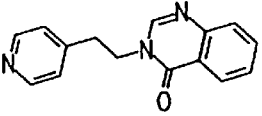 | 251.29 | | | | |
| 59-0049 | | 100.00 | uM | 4.49 | |
| | | 31.25 | uM | 0 | |
| | | 9.77 | uM | -4.77 | |
| | | 3.05 | uM | 1.96 | |
| | | 953.67 | nM | 8.69 | |
| | | 298.02 | nM | -5.04 | |
| | | 93.13 | nM | -2.24 | |
| | | 29.10 | nM | 1.69 | |
| | | 9.09 | nM | -4.49 | |
| | | 2.84 | nM | 2.24 | |
| | | 888.18 | pM | -0.3 | |
FIG. 3M

| | | | | |
|---|---|---|---|---|
| 59-0050 | 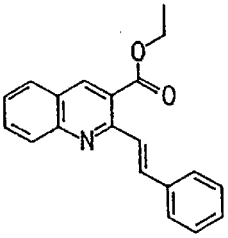 | 303.36 | | |
| 59-0050 | | | 100.00 uM | 45.79 |
| | | | 31.25 uM | 10.02 |
| | | | 9.77 uM | 11.29 |
| | | | 3.05 uM | -4.68 |
| | | | 953.67 nM | -6.92 |
| | | | 298.02 nM | -5.65 |
| | | | 93.13 nM | 1.69 |
| | | | 29.10 nM | -7.57 |
| | | | 9.09 nM | -12.05 |
| | | | 2.84 nM | -13.63 |
| | | | 888.18 pM | 5.2 |
| 59-0051 | 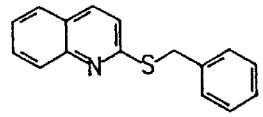 | 251.35 | | |
| 59-0051 | | | 100.00 uM | 32.36 |
| | | | 31.25 uM | -18.42 |
| | | | 9.77 uM | -0.55 |
| | | | 3.05 uM | -13.94 |
| | | | 953.67 nM | -12.02 |
| | | | 298.02 nM | -14.59 |
| | | | 93.13 nM | -7.55 |
| | | | 29.10 nM | -11.4 |
| | | | 9.09 nM | -14.91 |
| | | | 2.84 nM | -10.74 |
| | | | 888.18 pM | -20.03 |
FIG. 3N

| | | | | | |
|---|---|---|---|---|---|
| 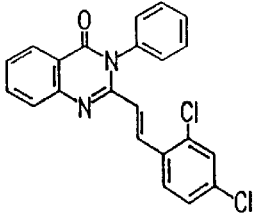 | | | | | |
| 59-0052 | 393.28 | | | | |
| 59-0052 | | 100.00 | uM | -21.62 | |
| | | 31.25 | uM | -13.32 | |
| | | 9.77 | uM | -21.31 | |
| | | 3.05 | uM | -11.08 | |
| | | 953.67 | nM | -20.66 | |
| | | 298.02 | nM | -17.14 | |
| | | 93.13 | nM | -16.49 | |
| | | 29.10 | nM | -11.4 | |
| | | 9.09 | nM | -10.74 | |
| | | 2.84 | nM | -11.08 | |
| | | 888.18 | pM | -14.59 | |
| 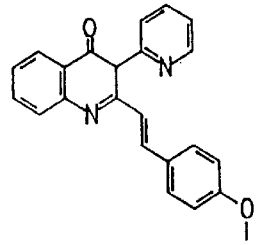 | | | | | |
| 59-0053 | 354.41 | | | | |
| 59-0053 | | 100.00 | uM | -17.14 | |
| | | 31.25 | uM | -21.31 | |
| | | 9.77 | uM | -9.47 | |
| | | 3.05 | uM | -11.08 | |
| | | 953.67 | nM | -0.83 | |
| | | 298.02 | nM | -11.4 | |
| | | 93.13 | nM | -9.47 | |
| | | 29.10 | nM | -19.72 | |
| | | 9.09 | nM | -18.45 | |
| | | 2.84 | nM | -10.09 | |
| | | 888.18 | pM | -2.76 | |
FIG. 30

| | | | | | |
|---|---|---|---|---|---|
| 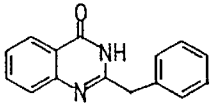 59-0054 | | 236.28 | | | |
| 59-0054 | | | 100.00 | uM | −20.04 |
| | | | 31.25 | uM | −6.95 |
| | | | 9.77 | uM | 8.3 |
| | | | 3.05 | uM | −3.37 |
| | | | 953.67 | nM | −2.4 |
| | | | 298.02 | nM | −0.99 |
| | | | 93.13 | nM | −0.99 |
| | | | 29.10 | nM | −1.94 |
| | | | 9.09 | nM | 5.92 |
| | | | 2.84 | nM | −2.17 |
| | | | 888.18 | pM | −9.31 |
| 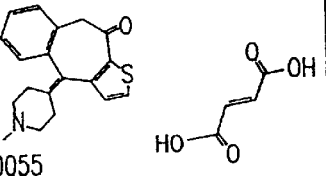 59-0055 | | 425.51 | | | |
| 59-0055 | | | 100.00 | uM | −13.76 |
| | | | 31.25 | uM | −9.51 |
| | | | 9.77 | uM | −2.02 |
| | | | 3.05 | uM | 3.24 |
| | | | 953.67 | nM | −6.27 |
| | | | 298.02 | nM | −4.05 |
| | | | 93.13 | nM | −1.62 |
| | | | 29.10 | nM | −7.49 |
| | | | 9.09 | nM | −7.09 |
| | | | 2.84 | nM | −3.04 |
| 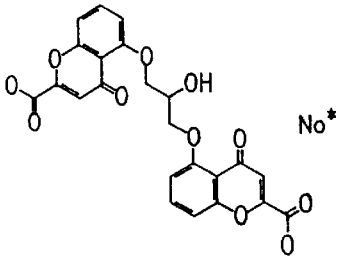 59-0056 | | 512.34 | | | |
| 59-0056 | | | 100.00 | uM | −1.42 |
| | | | 31.25 | uM | −4.87 |
| | | | 9.77 | uM | 0.18 |
| | | | 3.05 | uM | 3.84 |
| | | | 953.67 | nM | −5.07 |
| | | | 298.02 | nM | −7.29 |
| | | | 93.13 | nM | 0.001 |
| | | | 29.10 | nM | −4.25 |
| | | | 9.09 | nM | −1.02 |
| | | | 2.84 | nM | −3.85 |
FIG. 3P

| Structure | | Conc. | Unit | Value | |
|---|---|---|---|---|---|
| 59-0057 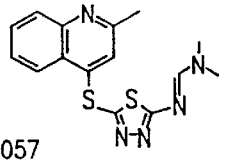 | | | | | |
| 59-0057 | | 100.00 | uM | -24.150 | |
| | | 31.25 | uM | -24.300 | |
| | | 9.77 | uM | -5.980 | |
| | | 3.05 | uM | -11.500 | |
| | | 953.67 | nM | -13.000 | |
| | | 298.02 | nM | -6.280 | |
| | | 93.13 | nM | -12.550 | |
| | | 29.10 | nM | -6.870 | |
| | | 9.09 | nM | -8.520 | |
| | | 2.84 | nM | -16.290 | |
| 59-0058 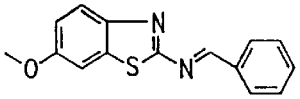 | | | | | |
| 59-0058 | | 100.00 | uM | 4.170 | |
| | | 31.25 | uM | 7.620 | |
| | | 9.77 | uM | -1.790 | |
| | | 3.05 | uM | -7.320 | |
| | | 953.67 | nM | -1.940 | |
| | | 298.02 | nM | -6.870 | |
| | | 93.13 | nM | -1.490 | |
| | | 29.10 | nM | -8.370 | |
| | | 9.09 | nM | -5.080 | |
| | | 2.84 | nM | -12.400 | |
| 59-0059 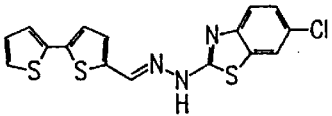 | | | | | |
| 59-0059 | | 100.00 | uM | -18.700 | |
| | | 31.25 | uM | -16.140 | |
| | | 9.77 | uM | -3.090 | |
| | | 3.05 | uM | 0.150 | |
| | | 953.67 | nM | 6.010 | |
| | | 298.02 | nM | -1.910 | |
| | | 93.13 | nM | -1.760 | |
| | | 29.10 | nM | -9.100 | |
| | | 9.09 | nM | -8.220 | |
| | | 2.84 | nM | -5.720 | |
FIG. 3Q

| | | | | | |
|---|---|---|---|---|---|
| 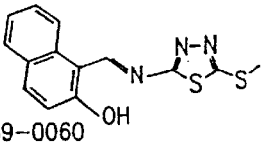 59-0060 | | | | | |
| 59-0060 | | 100.00 | uM | −4.250 | |
| | | 31.25 | uM | −14.520 | |
| | | 9.77 | uM | 1.030 | |
| | | 3.05 | uM | −1.180 | |
| | | 953.67 | nM | −13.200 | |
| | | 298.02 | nM | −0.740 | |
| | | 93.13 | nM | −3.670 | |
| | | 29.10 | nM | −7.340 | |
| | | 9.09 | nM | −1.310 | |
| | | 2.84 | nM | 0.290 | |
| 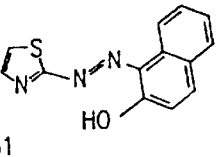 59-0061 | | | | | |
| 59-0061 | | 100.00 | uM | −17.890 | |
| | | 31.25 | uM | −18.770 | |
| | | 9.77 | uM | −17.170 | |
| | | 3.05 | uM | −14.080 | |
| | | 953.67 | nM | −17.020 | |
| | | 298.02 | nM | −7.190 | |
| | | 93.13 | nM | −1.910 | |
| | | 29.10 | nM | −0.440 | |
| | | 9.09 | nM | −6.010 | |
| | | 2.84 | nM | −4.560 | |
| 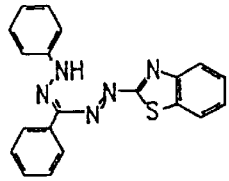 59-0062 | | | | | |
| 59-0062 | | 100.00 | uM | −13.940 | |
| | | 31.25 | uM | −12.910 | |
| | | 9.77 | uM | −4.560 | |
| | | 3.05 | uM | −4.540 | |
| | | 953.67 | nM | −6.900 | |
| | | 298.02 | nM | −4.100 | |
| | | 93.13 | nM | −1.620 | |
| | | 29.10 | nM | 3.230 | |
FIG. 3R

|  |  |  |  |  |
|---|---|---|---|---|
|  |  | 9.09 | nM | 8.070 |
|  |  | 2.84 | nM | 0.440 |
| 59-0063 |  |  |  |  |
| 59-0063 |  | 100.00 | uM | -2.510 |
|  |  | 31.25 | uM | -6.130 |
|  |  | 9.77 | uM | -8.950 |
|  |  | 3.05 | uM | -8.020 |
|  |  | 953.67 | nM | -8.010 |
|  |  | 298.02 | nM | -2.520 |
|  |  | 93.13 | nM | -5.810 |
|  |  | 29.10 | nM | -3.450 |
|  |  | 9.09 | nM | -4.390 |
|  |  | 2.84 | nM | -6.280 |
| 59-0064 |  |  |  |  |
| 59-0064 |  | 100.00 | uM | -23.090 |
|  |  | 31.25 | uM | -21.040 |
|  |  | 9.77 | uM | 78.400 |
|  |  | 3.05 | uM | 155.220 |
|  |  | 953.67 | nM | 113.120 |
|  |  | 298.02 | nM | 30.640 |
|  |  | 93.13 | nM | 15.240 |
|  |  | 29.10 | nM | 22.150 |
|  |  | 9.09 | nM | -0.770 |
|  |  | 2.84 | nM | 4.410 |
| 59-0065 |  |  |  |  |
| 59-0065 |  | 100.00 | uM | -2.030 |
|  |  | 31.05 | uM | -2.980 |
|  |  | 9.77 | uM | -15.240 |
|  |  | 3.05 | uM | -15.400 |
|  |  | 953.67 | nM | -15.240 |
|  |  | 298.02 | nM | -10.520 |
|  |  | 93.13 | nM | -13.830 |
|  |  | 29.10 | nM | -5.810 |
|  |  | 9.09 | nM | -3.620 |
|  |  | 2.84 | nM | -7.070 |

FIG. 3S

| | | | | | |
|---|---|---|---|---|---|
| 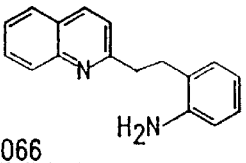 59-0066 | | | | | |
| 59-0066 | | 100.00 | uM | 10.060 | |
| | | 31.25 | uM | 2.680 | |
| | | 9.77 | uM | 10.850 | |
| | | 3.05 | uM | 14.610 | |
| | | 953.67 | nM | 0.950 | |
| | | 298.02 | nM | 3.780 | |
| | | 93.13 | nM | 1.730 | |
| | | 29.10 | nM | -2.820 | |
| | | 9.09 | nM | -2.820 | |
| | | 2.84 | nM | -3.920 | |
| 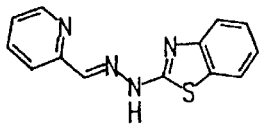 59-0067 | | | | | |
| 59-0067 | | 100.00 | uM | -24.040 | |
| | | 31.25 | uM | -24.890 | |
| | | 9.77 | uM | -1.450 | |
| | | 3.05 | uM | 60.900 | |
| | | 953.67 | nM | 133.860 | |
| | | 298.02 | nM | 75.330 | |
| | | 93.13 | nM | 28.760 | |
| | | 29.10 | nM | 20.070 | |
| | | 9.09 | nM | 4.980 | |
| | | 2.84 | nM | 4.450 | |
| 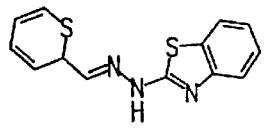 59-0068 | | | | | |
| 59-0068 | | 100.00 | uM | -22.130 | |
| | | 31.25 | uM | -7.880 | |
| | | 9.77 | uM | 93.900 | |
| | | 3.05 | uM | 81.060 | |
| | | 953.67 | nM | 22.330 | |
| | | 298.02 | nM | 17.300 | |
| | | 93.13 | nM | 8.460 | |
| | | 29.10 | nM | -3.530 | |
| | | 9.09 | nM | -4.230 | |
| | | 2.84 | nM | -6.140 | |
FIG. 3T

| | | | | | |
|---|---|---|---|---|---|
| 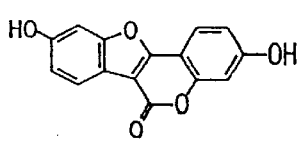 59-0069 | | | | | |
| 59-0069 | | 100.00 | uM | 5.490 | |
| | | 31.25 | uM | 9.670 | |
| | | 9.77 | uM | 16.090 | |
| | | 3.05 | uM | -7.180 | |
| | | 953.67 | nM | -2.840 | |
| | | 298.02 | nM | -3.710 | |
| | | 93.13 | nM | -11.180 | |
| | | 29.10 | nM | -5.790 | |
| | | 9.09 | nM | -7.180 | |
| | | 2.84 | nM | -4.750 | |
| 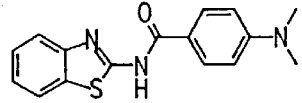 59-0070 | | | | | |
| 59-0070 | | 100.00 | uM | -25.930 | |
| | | 31.25 | uM | -23.000 | |
| | | 9.77 | uM | 36.060 | |
| | | 3.05 | uM | 214.280 | |
| | | 953.67 | nM | 158.530 | |
| | | 298.02 | nM | 72.890 | |
| | | 93.13 | nM | 20.940 | |
| | | 29.10 | nM | 7.760 | |
| | | 9.09 | nM | 7.590 | |
| | | 2.84 | nM | -8.400 | |
| 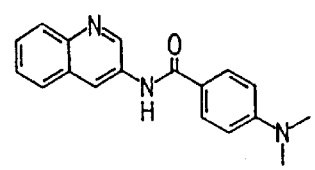 59-0071 | | | | | |
| 59-0071 | | 100.00 | uM | -18.650 | |
| | | 31.25 | uM | -15.540 | |
| | | 9.77 | uM | 17.060 | |
| | | 3.05 | uM | 176.090 | |
| | | 953.67 | nM | 76.070 | |
| | | 298.02 | nM | 31.260 | |
| | | 93.13 | nM | 16.410 | |
| | | 29.10 | nM | 4.870 | |
| | | 9.09 | nM | -7.330 | |
| | | 2.84 | nM | -4.660 | |
FIG. 3U

| | | | | | |
|---|---|---|---|---|---|
| 59-0072 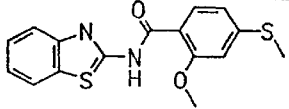 | | | | | |
| 59-0072 | | 100.00 | uM | -19.750 | |
| | | 31.25 | uM | -18.650 | |
| | | 9.77 | uM | -18.430 | |
| | | 3.05 | uM | -15.770 | |
| | | 953.67 | nM | 9.970 | |
| | | 298.02 | nM | 74.740 | |
| | | 93.13 | nM | 175.430 | |
| | | 29.10 | nM | 213.580 | |
| | | 9.09 | nM | 164.320 | |
| | | 2.84 | nM | 119.100 | |
| | | 888.18 | pM | 60.770 | |
| 59-0073 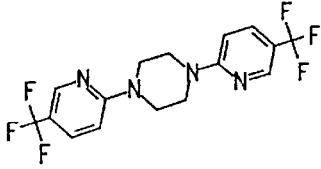 | | | | | |
| 59-0073 | | 100.00 | uM | -3.010 | |
| | | 31.25 | uM | -4.830 | |
| | | 9.77 | uM | -9.660 | |
| | | 3.05 | uM | -4.680 | |
| | | 953.67 | nM | -6.500 | |
| | | 298.02 | nM | -2.510 | |
| | | 93.13 | nM | 7.140 | |
| | | 29.10 | nM | 0.97 | |
| | | 9.09 | nM | -5.5 | |
| | | 2.84 | nM | 5.3 | |
| 59-0074 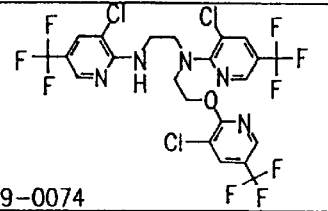 | | | | | |
| 59-0074 | | 100.00 | uM | -2.85 | |
| | | 31.25 | uM | 2.14 | |
| | | 9.77 | uM | -4.85 | |
| | | 3.05 | uM | -3.5 | |
| | | 953.67 | nM | -4.85 | |
| | | 298.02 | nM | 9.95 | |
| | | 93.13 | nM | 4.47 | |
| | | 29.10 | nM | -8 | |
| | | 9.09 | nM | -4.17 | |
| | | 2.84 | nM | 6.97 | |
FIG. 3V

| Structure | | Conc | Unit | Value | |
|---|---|---|---|---|---|
| 59-0075 (structure) | | | | | |
| 59-0075 | | 100.00 | uM | −0.68 | |
| | | 31.25 | uM | −10.16 | |
| | | 9.77 | uM | −5.35 | |
| | | 3.05 | uM | −6.5 | |
| | | 953.67 | nM | −0.85 | |
| | | 298.02 | nM | 5.97 | |
| | | 93.13 | nM | 0.97 | |
| | | 29.10 | nM | −2.35 | |
| | | 9.09 | nM | 0.32 | |
| | | 2.84 | nM | 10.47 | |
| 59-0076 (structure) | | | | | |
| 59-0076 | | 100.00 | uM | −19.12 | |
| | | 31.25 | uM | 9.29 | |
| | | 9.77 | uM | 10.63 | |
| | | 3.05 | uM | 22.43 | |
| | | 953.67 | nM | 19.93 | |
| | | 298.02 | nM | 3.47 | |
| | | 93.13 | nM | 19.93 | |
| | | 29.10 | nM | 10.63 | |
| | | 9.09 | nM | 14.28 | |
| | | 2.84 | nM | 11.3 | |
| 59-0077 (structure) | | | | | |
| 59-0077 | | 100.00 | uM | −20.96 | |
| | | 31.25 | uM | −16.23 | |
| | | 9.77 | uM | −10.58 | |
| | | 3.05 | uM | −11.96 | |
| | | 953.67 | nM | −19.44 | |
| | | 298.02 | nM | −17.3 | |
| | | 93.13 | nM | −13.79 | |
| | | 29.10 | nM | −15.62 | |
| | | 9.09 | nM | −14.09 | |
| | | 2.84 | nM | −14.4 | |

FIG. 3W

| | | | | | |
|---|---|---|---|---|---|
| 59-0078 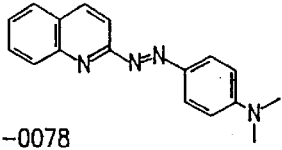 | | | | | |
| 59-0078 | | 100.00 | uM | -26.540 | |
| | | 31.25 | uM | -22.560 | |
| | | 9.77 | uM | 71.530 | |
| | | 3.05 | uM | 207.960 | |
| | | 953.67 | nM | 379.230 | |
| | | 298.02 | nM | 241.460 | |
| | | 93.13 | nM | 136.100 | |
| | | 29.10 | nM | 84.020 | |
| | | 9.09 | nM | 50.350 | |
| | | 2.84 | nM | 56.600 | |
| | | 888.18 | pM | 92.520 | |
| 59-0079 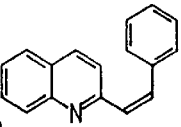 | | | | | |
| 59-0079 | | 100.00 | uM | -34.980 | |
| | | 31.25 | uM | -21.390 | |
| | | 9.77 | uM | 37.200 | |
| | | 3.05 | uM | 122.580 | |
| | | 953.67 | nM | 69.010 | |
| | | 298.02 | nM | 64.000 | |
| | | 93.13 | nM | 46.490 | |
| | | 29.10 | nM | 30.310 | |
| | | 9.09 | nM | 33.490 | |
| | | 2.84 | nM | 29.760 | |
| 59-0080 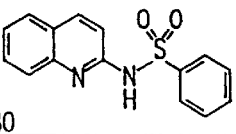 | | | | | |
| 59-0080 | | 100.00 | uM | 5.390 | |
| | | 31.25 | uM | 5.560 | |
| | | 9.77 | uM | 6.440 | |
| | | 3.05 | uM | 2.440 | |
| | | 953.67 | nM | -5.030 | |
| | | 298.02 | nM | 7.660 | |
| | | 93.13 | nM | -3.630 | |
| | | 29.10 | nM | 3.650 | |
| | | 9.09 | nM | 1.050 | |
| | | 2.84 | nM | 6.940 | |
| 59-0081 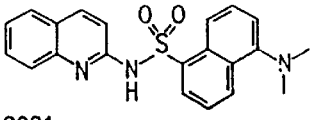 | | | | | |
FIG. 3X

| | | | | |
|---|---|---|---|---|
| 59-0081 | | 100.00 | uM | 62.840 |
| | | 31.25 | uM | 11.300 |
| | | 9.77 | uM | -8.670 |
| | | 3.05 | uM | 2.440 |
| | | 953.67 | nM | -5.200 |
| | | 298.02 | nM | -2.080 |
| | | 93.13 | nM | 1.220 |
| | | 29.10 | nM | -2.250 |
| | | 9.09 | nM | 1.050 |
| | | 2.84 | nM | -3.300 |
| 59-0082 | (structure) | | | |
| 59-0082 | | 100.00 | uM | 111.79 |
| | | 31.25 | uM | 62.68 |
| | | 9.77 | uM | 32.36 |
| | | 3.05 | uM | 9.11 |
| | | 953.67 | nM | -10.62 |
| | | 298.02 | nM | -1.86 |
| | | 93.13 | nM | -6.89 |
| | | 29.10 | nM | -3.91 |
| | | 9.09 | nM | 2.22 |
| | | 2.84 | nM | 16.36 |
| 59-0083 | (structure) | | | |
| 59-0083 | | 100.00 | uM | 48.93 |
| | | 31.25 | uM | 40.91 |
| | | 9.77 | uM | 25.85 |
| | | 3.05 | uM | 17.85 |
| | | 953.67 | nM | 8.55 |
| | | 298.02 | nM | 3.9 |
| | | 93.13 | nM | 2.05 |
| | | 29.10 | nM | 7.99 |
| | | 9.09 | nM | -3.91 |
| | | 2.84 | nM | 3.35 |
| 59-0084 | (structure) | | | |
| 59-0084 | | 100.00 | uM | 37.670 |
| | | 31.25 | uM | 26.050 |
| | | 9.77 | uM | 9.210 |
| | | 3.05 | uM | 10.070 |

FIG. 3Y

| | | | | |
|---|---|---|---|---|
| | | 953.67 | nM | 21.700 |
| | | 298.02 | nM | 5.900 |
| | | 93.13 | nM | 4.870 |
| | | 29.10 | nM | -10.920 |
| | | 9.09 | nM | 10.080 |
| | | 2.84 | nM | -2.080 |
| 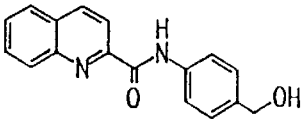 59-0085 | | | | |
| 59-0085 | | 100.00 | uM | 17.070 |
| | | 31.25 | uM | 41.890 |
| | | 9.77 | uM | 18.500 |
| | | 3.05 | uM | 20.340 |
| | | 953.67 | nM | 22.490 |
| | | 298.02 | nM | 8.090 |
| | | 93.13 | nM | 11.790 |
| | | 29.10 | nM | 1.240 |
| | | 9.09 | nM | -0.760 |
| | | 2.84 | nM | 5.940 |
|  59-0086 | | | | |
| 59-0086 | | 100.00 | uM | 30.750 |
| | | 31.25 | uM | 31.190 |
| | | 9.77 | uM | 14.790 |
| | | 3.05 | uM | 13.500 |
| | | 953.67 | nM | 14.080 |
| | | 298.02 | nM | 3.940 |
| | | 93.13 | nM | 9.370 |
| | | 29.10 | nM | -2.610 |
| | | 9.09 | nM | -5.040 |
| | | 2.84 | nM | 1.530 |
|  59-0087 | | | | |
| 59-0087 | | 100.00 | uM | 10.660 |
| | | 31.25 | uM | 11.080 |
| | | 9.77 | uM | 3.100 |
| | | 3.05 | uM | -1.320 |
| | | 953.67 | nM | 17.070 |
| | | 298.02 | nM | 7.950 |
| | | 93.13 | nM | -4.460 |
| | | 29.10 | nM | 4.510 |
| | | 9.09 | nM | -0.470 |
| | | 2.84 | nM | 9.660 |
FIG. 3Z

| | | | | | |
|---|---|---|---|---|---|
| 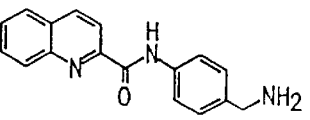 59-0088 | | | | | |
| 59-0088 | | 100.00 | uM | | |
| | | 31.25 | uM | | |
| | | 9.77 | uM | | |
| | | 3.05 | uM | | |
| | | 953.67 | nM | | |
| | | 298.02 | nM | | |
| | | 93.13 | nM | | |
| | | 29.10 | nM | | |
| | | 9.09 | nM | | |
| | | 2.84 | nM | | |
| 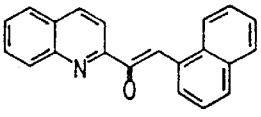 59-0089 | | | | | |
| 59-0089 | | 100.00 | uM | 60.09 | |
| | | 31.25 | uM | 116.25 | |
| | | 9.77 | uM | 65.85 | |
| | | 3.05 | uM | 36.1 | |
| | | 953.67 | nM | 37.96 | |
| | | 298.02 | nM | 18.42 | |
| | | 93.13 | nM | 6.33 | |
| | | 29.10 | nM | 13.58 | |
| | | 9.09 | nM | 0.75 | |
| | | 2.84 | nM | -5.77 | |
| 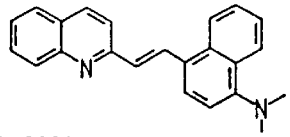 59-0090 | | | | | |
| 59-0090 | | 100.00 | uM | 32.77 | |
| | | 31.25 | uM | 24.63 | |
| | | 9.77 | uM | 19.5 | |
| | | 3.05 | uM | 41.31 | |
| | | 953.67 | nM | 9.8 | |
| | | 298.02 | nM | -1.76 | |
| | | 93.13 | nM | 3.53 | |
| | | 29.10 | nM | 2.95 | |
| | | 9.09 | nM | 2.95 | |
| | | 2.84 | nM | 7.8 | |
| 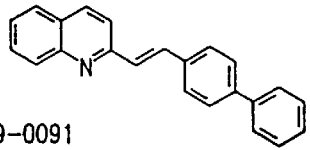 59-0091 | | | | | |
| 59-0091 | | 100.00 | uM | 0.26 | |
| | | 31.25 | uM | 13.54 | |
FIG. 3AA

| | | | | |
|---|---|---|---|---|
| | | 9.77 | uM | 95.94 |
| | | 3.05 | uM | 87.71 |
| | | 953.67 | nM | 44.17 |
| | | 298.02 | nM | 38.26 |
| | | 93.13 | nM | 23.87 |
| | | 29.10 | nM | 21.65 |
| | | 9.09 | nM | 10.95 |
| | | 2.84 | nM | 20.92 |
| 59-0092 (quinoline-CH=CH-naphthalene) | | | | |
| 59-0092 | | 100.00 | uM | -11.56 |
| | | 31.25 | uM | 17.84 |
| | | 9.77 | uM | 50.19 |
| | | 3.05 | uM | 25.84 |
| | | 953.67 | nM | 14.4 |
| | | 298.02 | nM | 6.77 |
| | | 93.13 | nM | 8.62 |
| | | 29.10 | nM | 2.22 |
| | | 9.09 | nM | 8.38 |
| | | 2.84 | nM | 1 |
| 59-0093 (quinoline-CH=CH-pyridine) | | | | |
| 59-0093 | | 100.00 | uM | -11.67 |
| | | 31.25 | uM | 15.02 |
| | | 9.77 | uM | 35.44 |
| | | 3.05 | uM | 29.89 |
| | | 953.67 | nM | 22.88 |
| | | 298.02 | nM | 19.56 |
| | | 93.13 | nM | 5.18 |
| | | 29.10 | nM | 7.39 |
| | | 9.09 | nM | 4.56 |
| | | 2.84 | nM | 5.9 |
| 59-0094 (quinoline-CH=CH-quinoline) | | | | |
| 59-0094 | | 100.00 | uM | -17.69 |
| | | 31.25 | uM | 45.15 |
| | | 9.77 | uM | 24.97 |
| | | 3.05 | uM | 19.81 |
| | | 953.67 | nM | 9.35 |
| | | 298.02 | nM | 1.36 |
| | | 93.13 | nM | 9.24 |
| | | 29.10 | nM | -0.48 |
| | | 9.09 | nM | 6.16 |
| | | 2.84 | nM | 1.61 |

FIG. 3BB

| Compound | | Conc | | Value |
|---|---|---|---|---|
| 59-0095 (structure) | | | | |
| 59-0095 | | 100.00 uM | | 44.7 |
| | | 31.25 uM | | 47.61 |
| | | 9.77 uM | | 12.78 |
| | | 3.05 uM | | 21.49 |
| | | 953.67 nM | | 15.01 |
| | | 298.02 nM | | 10.22 |
| | | 93.13 nM | | 13.98 |
| | | 29.10 nM | | 20.31 |
| | | 9.09 nM | | 10.9 |
| | | 2.84 nM | | 9.21 |
| 59-0096 (structure) | | | | |
| 59-0096 | | 100.00 uM | | 413.05 |
| | | 31.25 uM | | 287.23 |
| | | 9.77 uM | | 137.38 |
| | | 3.05 uM | | 78.5 |
| | | 953.67 nM | | 49.13 |
| | | 298.02 nM | | 50.68 |
| | | 93.13 nM | | 47.95 |
| | | 29.10 nM | | 26.28 |
| | | 9.09 nM | | 18.75 |
| | | 2.84 nM | | 22.17 |
| 59-0097 (structure) | | | | |
| 59-0097 | | 100.00 uM | | 77.47 |
| | | 31.25 uM | | 201.9 |
| | | 9.77 uM | | 160.93 |
| | | 3.05 uM | | 61.44 |
| | | 953.67 nM | | 47.78 |
| | | 298.02 nM | | 51.54 |
| | | 93.13 nM | | 34.64 |
| | | 29.10 nM | | 43.18 |
| | | 9.09 nM | | 39.91 |
| | | 2.84 nM | | 27.13 |

FIG. 3CC

| Structure | | Conc | Units | | |
|---|---|---|---|---|---|
| 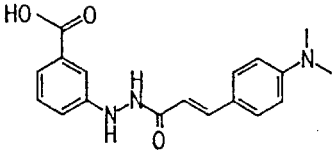 59-0098 | | | | | |
| 59-0098 | | 100.00 | uM | | -1.38 |
| | | 31.25 | uM | | 186.89 |
| | | 9.77 | uM | | 221.7 |
| | | 3.05 | uM | | 164.69 |
| | | 953.67 | nM | | 96.94 |
| | | 298.02 | nM | | 68.25 |
| | | 93.13 | nM | | 57 |
| | | 29.10 | nM | | 51.88 |
| | | 9.09 | nM | | 41.29 |
| | | 2.84 | nM | | 33.43 |
| 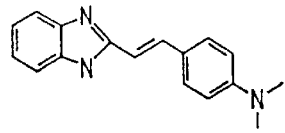 59-0099 | | | | | |
| 59-0099 | | 100.00 | uM | 13.040 | |
| | | 31.25 | uM | 56.880 | |
| | | 9.77 | uM | 119.340 | |
| | | 3.05 | uM | 237.420 | |
| | | 953.67 | nM | 285.440 | |
| | | 298.02 | nM | 164.610 | |
| | | 93.13 | nM | 123.300 | |
| | | 29.10 | nM | 69.240 | |
| | | 9.09 | nM | 44.500 | |
| | | 2.84 | nM | 47.390 | |
| 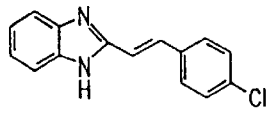 59-0100 | | | | | |
| 59-0100 | | 100.00 | uM | -10.020 | |
| | | 31.25 | uM | -10.730 | |
| | | 9.77 | uM | 30.340 | |
| | | 3.05 | uM | 114.410 | |
| | | 953.67 | nM | 77.540 | |
| | | 298.02 | nM | 40.290 | |
| | | 93.13 | nM | 35.730 | |
| | | 29.10 | nM | 28.290 | |
| | | 9.09 | nM | 17.480 | |
| | | 2.84 | nM | 11.470 | |
| 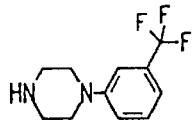 59-0101 | | | | | |
| 59-0101 | | 100.00 | uM | 26.370 | |
FIG. 3DD

| | | | | |
|---|---|---|---|---|
| | | 31.25 uM | 12.440 | |
| | | 9.77 uM | −0.780 | |
| | | 3.05 uM | 10.280 | |
| | | 953.67 nM | 2.110 | |
| | | 298.02 nM | 7.860 | |
| | | 93.13 nM | 1.140 | |
| | | 29.10 nM | 2.820 | |
| | | 9.09 nM | 4.150 | |
| | | 2.84 nM | 5.590 | |
|  59-0102 | 284.34 | | | |
| 59-0102 | | 100.00 uM | −24.350 | |
| | | 31.25 uM | −11.140 | |
| | | 9.77 uM | 63.540 | |
| | | 3.05 uM | 121.320 | |
| | | 953.67 nM | 79.530 | |
| | | 298.02 nM | 72.460 | |
| | | 93.13 nM | 66.290 | |
| | | 29.10 nM | 45.690 | |
| | | 9.09 nM | 27.260 | |
| | | 2.84 nM | 42.330 | |
| | | 888.18 nM | 33.430 | |
| 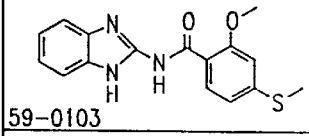 59-0103 | 313.38 | | | |
| | | 100.00 uM | −29.69 | |
| | | 31.25 uM | −29.53 | |
| | | 9.77 uM | −28.22 | |
| | | 3.05 uM | −27.72 | |
| | | 953.67 nM | −5.58 | |
| | | 298.02 nM | 54.15 | |
| | | 93.13 nM | 170.95 | |
| | | 29.10 nM | 222.87 | |
| | | 9.09 nM | 210.39 | |
| | | 2.84 nM | 203.4 | |
| | | 0.80 nM | 114.55 | |
| 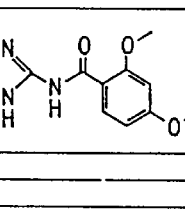 59-0104 | 297.31 | | | |
| | | 100.00 uM | −29.84 | |
| | | 31.25 uM | −26.72 | |
| | | 9.77 uM | −29.2 | |
| | | 3.05 uM | −27.05 | |
| | | 953.67 nM | 24.37 | |
| | | 298.02 nM | 196.42 | |
| | | 93.13 nM | 213.89 | |
FIG. 3EE

| | | 29.10 | nM | 220.04 |
| | | 9.09 | nM | 245.42 |
| | | 2.84 | nM | 182.45 |
| | | 0.80 | nM | 119.55 |
| 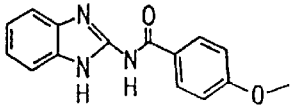 59-0105 | 267.29 | | | |
| | | 100.00 | uM | -25.72 |
| | | 31.25 | uM | -15.89 |
| | | 9.77 | uM | 31.7 |
| | | 3.05 | uM | 54.17 |
| | | 953.67 | nM | 53.67 |
| | | 298.02 | nM | 41.35 |
| | | 93.13 | nM | 44.5 |
| | | 29.10 | nM | 39.02 |
| | | 9.09 | nM | 25.38 |
| | | 2.84 | nM | 31.7 |
| | | 0.80 | nM | 18.05 |
| 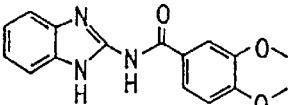 59-0106 | 297.31 | | | |
| | | 100.00 | uM | -14.05 |
| | | 31.25 | uM | 223.52 |
| | | 9.77 | uM | 202.58 |
| | | 3.05 | uM | 107.73 |
| | | 953.67 | nM | 71.3 |
| | | 298.02 | nM | 44.84 |
| | | 93.13 | nM | 26.54 |
| | | 29.10 | nM | 23.05 |
| | | 9.09 | nM | 27.87 |
| | | 2.84 | nM | 12.23 |
| | | 0.80 | nM | 11.4 |
| 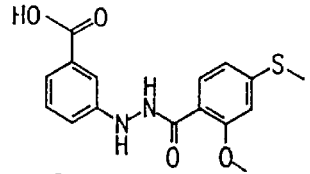 59-0107 | 332.38 | | | |
| | | 100.00 | uM | 48.55 |
| | | 31.25 | uM | 22.87 |
| | | 9.77 | uM | 7.19 |
| | | 3.05 | uM | 0.65 |
| | | 953.67 | nM | 11.12 |
| | | 298.02 | nM | -3.92 |
| | | 93.13 | nM | 1.09 |
| | | 29.10 | nM | -15.69 |
FIG. 3FF

| | | 9.09 | nM | −11.32 | |
| --- | --- | --- | --- | --- | --- |
| | | 2.84 | nM | −2.62 | |
| | | 0.80 | nM | −16.11 | |
| 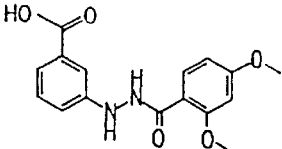 59-0108 | 316.31 | | | | |
| | | 100.00 | uM | 227.73 | |
| | | 31.25 | uM | 96.02 | |
| | | 9.77 | uM | 58.57 | |
| | | 3.05 | uM | 37.23 | |
| | | 953.67 | nM | 18.94 | |
| | | 298.02 | nM | 25.68 | |
| | | 93.13 | nM | −4.8 | |
| | | 29.10 | nM | 2.62 | |
| | | 9.09 | nM | −4.8 | |
| | | 2.84 | nM | 3.92 | |
| | | 0.80 | nM | 4.14 | |
| 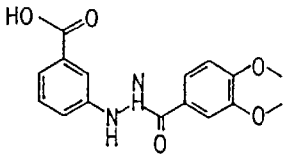 59-0109 | 316.31 | | | | |
| | | 100.00 | uM | 43.12 | |
| | | 31.25 | uM | 27.64 | |
| | | 9.77 | uM | 5.89 | |
| | | 3.05 | uM | 6.32 | |
| | | 953.67 | nM | 13.51 | |
| | | 298.02 | nM | 7.85 | |
| | | 93.13 | nM | 3.71 | |
| | | 29.10 | nM | −3.27 | |
| | | 9.09 | nM | 5.01 | |
| | | 2.84 | nM | −4.58 | |
| | | 0.80 | nM | 6.98 | |
| 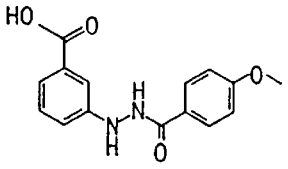 59-0110 | 286.29 | | | | |
| | | 100.00 | uM | 65.11 | |
| | | 31.25 | uM | 67.05 | |
| | | 9.77 | uM | 35.27 | |
| | | 3.05 | uM | 25.26 | |
| | | 953.67 | nM | 27.01 | |
| | | 298.02 | nM | 15.24 | |
FIG. 3GG

| | | | | |
|---|---|---|---|---|
| | | 93.13 | nM | 10.68 |
| | | 29.10 | nM | 5.89 |
| | | 9.09 | nM | 5.45 |
| | | 2.84 | nM | 10.24 |
| | | 0.80 | nM | 4.14 |
| 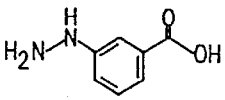 59-0111 | 152.15 | | | |
| | | 100.00 | uM | 23.360 |
| | | 31.25 | uM | 22.330 |
| | | 9.77 | uM | 12.260 |
| | | 3.05 | uM | 5.390 |
| | | 953.67 | nM | 2.190 |
| | | 298.02 | nM | 1.230 |
| | | 93.13 | nM | 2.430 |
| | | 29.10 | nM | 6.350 |
| | | 9.09 | nM | 4.350 |
| | | 2.84 | nM | 4.350 |
| | | 0.80 | nM | 3.230 |
| 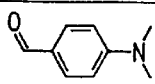 59-0112 | 149.19 | | | |
| | | 100.00 | uM | 2.670 |
| | | 31.25 | uM | 4.670 |
| | | 9.77 | uM | 2.750 |
| | | 3.05 | uM | 3.790 |
| | | 953.67 | nM | 4.270 |
| | | 298.02 | nM | 1.150 |
| | | 93.13 | nM | 9.630 |
| | | 29.10 | nM | 0.920 |
| | | 9.09 | nM | 0.510 |
| | | 2.84 | nM | 12.900 |
| | | 0.80 | nM | 2.990 |
| 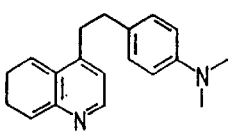 59-0113 | 274.37 | | | |
| | | 100.00 | uM | 22.010 |
| | | 31.25 | uM | 25.940 |
| | | 9.77 | uM | 7.500 |
| | | 3.05 | uM | 3.070 |
| | | 953.67 | nM | -0.760 |
| | | 298.02 | nM | -4.690 |
| | | 93.13 | nM | -4.790 |
| | | 29.10 | nM | 5.090 |
| | | 9.09 | nM | 0.150 |
| | | 2.84 | nM | -0.250 |
| | | 0.80 | nM | 0.150 |
FIG. 3HH

| Compound | MW | Conc | | Value |
|---|---|---|---|---|
| 59-0114 | 475.54 | | | |
| | | 100.00 | uM | 52.030 |
| | | 31.25 | uM | 36.120 |
| | | 9.77 | uM | 25.840 |
| | | 3.05 | uM | 16.670 |
| | | 953.67 | nM | 12.540 |
| | | 298.02 | nM | 9.420 |
| | | 93.13 | nM | −1.060 |
| | | 29.10 | nM | 2.160 |
| | | 9.09 | nM | −6.000 |
| | | 2.84 | nM | 2.470 |
| | | 0.80 | nM | −1.460 |
| 59-0115 | 318.87 | | | |
| | | 100.00 | uM | 73.700 |
| | | 31.25 | uM | 2.770 |
| | | 9.77 | uM | −10.430 |
| | | 3.05 | uM | −12.340 |
| | | 953.67 | nM | −13.750 |
| | | 298.02 | nM | −13.960 |
| | | 93.13 | nM | −11.940 |
| | | 29.10 | nM | −9.830 |
| | | 9.09 | nM | −8.820 |
| | | 2.84 | nM | −0.950 |
| | | 0.80 | nM | −0.050 |
| 59-0116 | 269.30 | | | |
| | | 100.00 | uM | 31.380 |
| | | 31.25 | uM | 109.060 |
| | | 9.77 | uM | 231.070 |
| | | 3.05 | uM | 240.670 |
| | | 953.67 | nM | 132.020 |
| | | 298.02 | nM | 75.820 |
| | | 93.13 | nM | 53.250 |
| | | 29.10 | nM | 47.500 |
| | | 9.09 | nM | 39.440 |
| | | 2.84 | nM | 42.170 |
| | | 0.80 | nM | 31.180 |
| 59-0117 | 268.38 | | | |
| | | 100.00 | uM | −68.520 |

FIG. 3II

| | | | | |
|---|---|---|---|---|
| | | 31.25 | uM | -7.450 |
| | | 9.77 | uM | 111.630 |
| | | 3.05 | uM | 64.340 |
| | | 953.67 | nM | 4.740 |
| | | 298.02 | nM | -19.270 |
| | | 93.13 | nM | -26.660 |
| | | 29.10 | nM | -28.880 |
| | | 9.09 | nM | -42.180 |
| | | 2.84 | nM | -41.300 |
| | | 0.80 | nM | -39.220 |
| 59-0118 | 313.36 | | | |
| | | 100.00 | uM | -67.170 |
| | | 31.25 | uM | -56.580 |
| | | 9.77 | uM | -58.060 |
| | | 3.05 | uM | -55.720 |
| | | 953.67 | nM | -48.200 |
| | | 298.02 | nM | -50.300 |
| | | 93.13 | nM | -33.310 |
| | | 29.10 | nM | -47.340 |
| | | 9.09 | nM | -49.310 |
| | | 2.84 | nM | -56.200 |
| | | 0.80 | nM | -57.310 |
| 59-0119 | 314.34 | | | |
| | | 100.00 | uM | 167.500 |
| | | 31.25 | uM | -29.240 |
| | | 9.77 | uM | -57.800 |
| | | 3.05 | uM | -52.030 |
| | | 953.67 | nM | -54.240 |
| | | 298.02 | nM | -53.870 |
| | | 93.13 | nM | -38.110 |
| | | 29.10 | nM | -55.100 |
| | | 9.09 | nM | -52.270 |
| | | 2.84 | nM | -53.500 |
| | | 0.80 | nM | -43.650 |
| 59-0120 | 504.49 | | | |
| | | 100.00 | uM | -82.790 |
| | | 31.25 | uM | -80.470 |
| | | 9.77 | uM | -66.800 |
| | | 3.05 | uM | -50.790 |
| | | 953.67 | nM | -54.240 |
| | | 298.02 | nM | -45.250 |
| | | 93.13 | nM | -50.660 |

FIG. 3JJ

| | | | | |
|---|---|---|---|---|
| | | 29.10 | nM | -50.300 |
| | | 9.09 | nM | -50.300 |
| | | 2.84 | nM | -50.300 |
| | | 0.80 | nM | -43.280 |
| 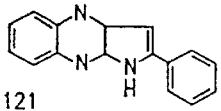 59-0121 | 245.29 | | | |
| | | 100.00 | uM | -79.690 |
| | | 31.25 | uM | -75.590 |
| | | 9.77 | uM | 25.650 |
| | | 3.05 | uM | 94.850 |
| | | 953.67 | nM | 43.910 |
| | | 298.02 | nM | -1.800 |
| | | 93.13 | nM | -4.150 |
| | | 29.10 | nM | -22.050 |
| | | 9.09 | nM | -31.110 |
| | | 2.84 | nM | -26.760 |
| | | 0.80 | nM | -28.270 |
| 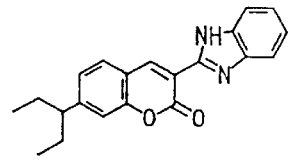 59-0122 | 333.39 | | | |
| | | 100.00 | uM | -19.050 |
| | | 31.25 | uM | -12.080 |
| | | 9.77 | uM | -7.610 |
| | | 3.05 | uM | 25.210 |
| | | 953.67 | nM | 83.580 |
| | | 298.02 | nM | 87.220 |
| | | 93.13 | nM | 63.890 |
| | | 29.10 | nM | 42.680 |
| | | 9.09 | nM | 45.320 |
| | | 2.84 | nM | 37.780 |
| | | 0.80 | nM | 27.030 |
| 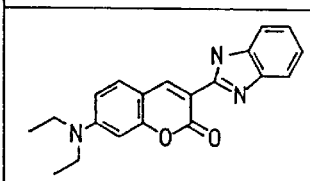 59-0123 | 347.42 | | | |
| | | 100.00 | uM | 34.430 |
| | | 31.25 | uM | 34.710 |
| | | 9.77 | uM | 38.620 |
| | | 3.05 | uM | 55.100 |
| | | 953.67 | nM | 51.900 |
| | | 298.02 | nM | 41.410 |
| | | 93.13 | nM | 29.970 |
| | | 29.10 | uM | 13.760 |
| | | 9.09 | nM | 17.120 |
| | | 2.84 | nM | 13.480 |
| | | 0.80 | nM | 1.190 |
FIG. 3KK

| Structure | | Conc. | | Value | |
|---|---|---|---|---|---|
| 59-0124 | 350.44 | | | | |
| | | 100.00 | uM | 56.640 | |
| | | 31.25 | uM | 81.500 | |
| | | 9.77 | uM | 145.880 | |
| | | 3.05 | uM | 135.830 | |
| | | 953.67 | nM | 268.990 | |
| | | 298.02 | nM | 224.290 | |
| | | 93.13 | nM | 134.850 | |
| | | 29.10 | nM | 91.690 | |
| | | 9.09 | nM | 80.390 | |
| | | 2.84 | nM | 63.060 | |
| | | 0.80 | nM | 51.460 | |
| 59-0125 | 372.45 | | | | |
| | | 100.00 | uM | -6.780 | |
| | | 31.25 | uM | 67.530 | |
| | | 9.77 | uM | 54.120 | |
| | | 3.05 | uM | 28.700 | |
| | | 953.67 | nM | 21.580 | |
| | | 298.02 | nM | 22.280 | |
| | | 93.13 | nM | 22.700 | |
| | | 29.10 | nM | 1.630 | |
| | | 9.09 | nM | 15.700 | |
| | | 2.84 | nM | 9.840 | |
| | | 0.80 | nM | 8.460 | |

FIG. 3LL

| | | | | |
|---|---|---|---|---|
| 59-0126 | 260.30 | | | |
| | | 100.00 | uM | -17.390 |
| | | 31.25 | uM | -13.100 |
| | | 9.77 | uM | 9.270 |
| | | 3.05 | uM | 40.530 |
| | | 953.67 | nM | 21.390 |
| | | 298.02 | nM | 25.660 |
| | | 93.13 | nM | 9.430 |
| | | 29.10 | nM | 6.360 |
| | | 9.09 | nM | 6.510 |
| | | 2.84 | nM | 0.080 |
| | | 0.80 | nM | 3.750 |
| 59-0127 | 329.41 | | | |
| | | 100.00 | uM | -20.610 |
| | | 31.25 | uM | -21.820 |
| | | 9.77 | uM | -6.060 |
| | | 3.05 | uM | -3.900 |
| | | 953.67 | nM | -8.820 |
| | | 298.02 | nM | -6.200 |
| | | 93.13 | nM | 11.880 |
| | | 29.10 | nM | 1.610 |
| | | 9.09 | nM | 3.600 |
| | | 2.84 | nM | -2.070 |
| | | 0.80 | nM | 4.220 |
| 59-0128 | 436.34 | | | |
| | | 100.00 | uM | |
| | | 31.25 | uM | |
| | | 9.77 | uM | |
| | | 3.05 | uM | |
| | | 953.67 | nM | |
| | | 298.02 | nM | |
| | | 93.13 | nM | |
| | | 29.10 | nM | |

FIG. 3MM

| | | | | | |
|---|---|---|---|---|---|
| | | 9.09 | nM | | |
| | | 2.84 | nM | | |
| | | 0.80 | nM | | |
| 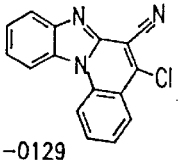 59-0129 | 277.71 | | | | |
| | | 100.00 | uM | −20.46 | |
| | | 31.25 | uM | −21.21 | |
| | | 9.77 | uM | 44.36 | |
| | | 3.05 | uM | 4.38 | |
| | | 953.67 | nM | 5.9 | |
| | | 298.02 | nM | 3.6 | |
| | | 93.13 | nM | 2.07 | |
| | | 29.10 | nM | 4.22 | |
| | | 9.09 | nM | −0.68 | |
| | | 2.84 | nM | 12.48 | |
| | | 0.80 | nM | −0.53 | |
| 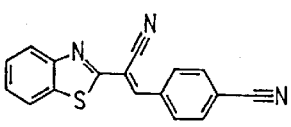 59-0130 | 287.34 | | | | |
| | | 100.00 | uM | 4.38 | |
| | | 31.25 | uM | 8.35 | |
| | | 9.77 | uM | 5.91 | |
| | | 3.05 | uM | 4.98 | |
| | | 953.67 | nM | 0.39 | |
| | | 298.02 | nM | 8.66 | |
| | | 93.13 | nM | 2.85 | |
| | | 29.10 | nM | 3.6 | |
| | | 9.09 | nM | 4.36 | |
| | | 2.84 | nM | 8.96 | |
| | | 0.80 | nM | 24.75 | |
| 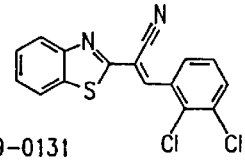 59-0131 | 331.22 | | | | |
| | | 100.00 | uM | 8.75 | |
| | | 31.25 | uM | 0.12 | |
| | | 9.77 | uM | −10.38 | |
| | | 3.05 | uM | −6.39 | |
| | | 953.67 | nM | −2.81 | |
| | | 298.02 | nM | 1.61 | |
| | | 93.13 | nM | −1.98 | |
| | | 29.10 | nM | −2.59 | |
| | | 9.09 | nM | 0.14 | |
| | | 2.84 | nM | −5.77 | |
FIG. 3NN

| | | 0.80 | nM | −0.5 | |
|---|---|---|---|---|---|
| 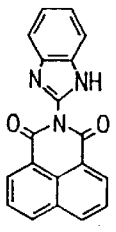 59-0132 | 313.32 | | | | |
| | | 100.00 | uM | −17.1 | |
| | | 31.25 | uM | −14.81 | |
| | | 9.77 | uM | −14.37 | |
| | | 3.05 | uM | −12.92 | |
| | | 953.67 | nM | −13.54 | |
| | | 298.02 | nM | −10.38 | |
| | | 93.13 | nM | −3.65 | |
| | | 29.10 | nM | −7.66 | |
| | | 9.09 | nM | −6.18 | |
| | | 2.84 | nM | −9.97 | |
| | | 0.80 | nM | −2.81 | |
| 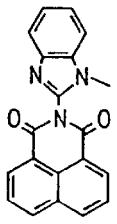 59-0133 | 327.34 | | | | |
| | | 100.00 | uM | −16.04 | |
| | | 31.25 | uM | −16.91 | |
| | | 9.77 | uM | −17.31 | |
| | | 3.05 | uM | −16.7 | |
| | | 953.67 | nM | −9.34 | |
| | | 298.02 | nM | −12.69 | |
| | | 93.13 | nM | −11.23 | |
| | | 29.10 | nM | −17.74 | |
| | | 9.09 | nM | 6.02 | |
| | | 2.84 | nM | −4.71 | |
| | | 0.80 | nM | 0.55 | |
FIG. 300

| Structure | ID | MW | Conc | Unit | Value | |
|---|---|---|---|---|---|---|
| 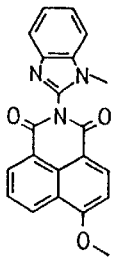 | 59-0134 | 357.37 | | | | |
| | | | 100.00 | uM | | |
| | | | 31.25 | uM | | |
| | | | 9.77 | uM | | |
| | | | 3.05 | uM | | |
| | | | 953.67 | nM | | |
| | | | 298.02 | nM | | |
| | | | 93.13 | nM | | |
| | | | 29.10 | nM | | |
| | | | 9.09 | nM | | |
| | | | 2.84 | nM | | |
| | | | 0.80 | nM | | |
| 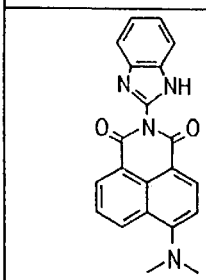 | 59-0135 | 356.39 | | | | |
| | | | 100.00 | uM | −21.3 | |
| | | | 31.25 | uM | −14.16 | |
| | | | 9.77 | uM | −1.98 | |
| | | | 3.05 | uM | 0.97 | |
| | | | 953.67 | nM | 11.68 | |
| | | | 298.02 | nM | −1.13 | |
| | | | 93.13 | nM | −1.55 | |
| | | | 29.10 | nM | −2.81 | |
| | | | 9.09 | nM | 12.11 | |
| | | | 2.84 | nM | −5.75 | |
| | | | 0.80 | nM | 4.54 | |
| 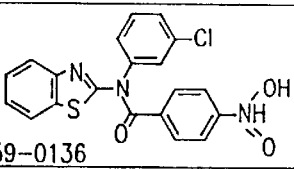 | 59-0136 | 411.87 | | | | |
| | | | 100.00 | uM | | |
| | | | 31.25 | uM | | |
| | | | 9.77 | uM | | |
| | | | 3.05 | uM | | |
| | | | 953.67 | nM | | |
FIG. 3PP

| | | | | | |
|---|---|---|---|---|---|
| | | 298.02 | nM | | |
| | | 93.13 | nM | | |
| | | 29.10 | nM | | |
| | | 9.09 | nM | | |
| | | 2.84 | nM | | |
| | | 0.80 | nM | | |
| 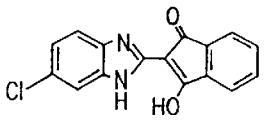 59-0137 | 296.71 | | | | |
| | | 100.00 | uM | | |
| | | 31.25 | uM | | |
| | | 9.77 | uM | | |
| | | 3.05 | uM | | |
| | | 953.67 | nM | | |
| | | 298.02 | nM | | |
| | | 93.13 | nM | | |
| | | 29.10 | nM | | |
| | | 9.09 | nM | | |
| | | 2.84 | nM | | |
| | | 0.80 | nM | | |
| 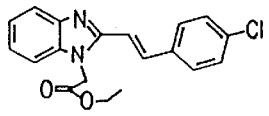 59-0138 | 340.81 | | | | |
| | | 100.00 | uM | -6.91 | |
| | | 31.25 | uM | -12.68 | |
| | | 9.77 | uM | 4.59 | |
| | | 3.05 | uM | 32.61 | |
| | | 953.67 | nM | 19.07 | |
| | | 298.02 | nM | 8.18 | |
| | | 93.13 | nM | 2.26 | |
| | | 29.10 | nM | 12.22 | |
| | | 9.09 | nM | 56.42 | |
| | | 2.84 | nM | 7.24 | |
| | | 0.80 | nM | 1.63 | |
| 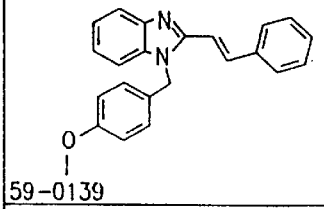 59-0139 | 340.43 | | | | |
| | | 100.00 | uM | 45.53 | |
| | | 31.25 | uM | 44.59 | |
| | | 9.77 | uM | 53.62 | |
| | | 3.05 | uM | 30.42 | |
| | | 953.67 | nM | 28.25 | |
| | | 298.02 | uM | 20.31 | |
| | | 93.13 | nM | 18.6 | |
FIG. 3QQ

|  |  | 29.10 | nM | 14.4 |
|  |  | 9.09 | nM | 13.93 |
|  |  | 2.84 | nM | 18.61 |
|  |  | 0.80 | nM | 10.05 |
| 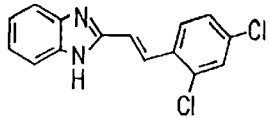 59-0140 | 289.17 |  |  |  |
|  |  | 100.00 | uM |  |
|  |  | 31.25 | uM |  |
|  |  | 9.77 | uM |  |
|  |  | 3.05 | uM |  |
|  |  | 953.67 | nM |  |
|  |  | 298.02 | nM |  |
|  |  | 93.13 | nM |  |
|  |  | 29.10 | nM |  |
|  |  | 9.09 | nM |  |
|  |  | 2.84 | nM |  |
|  |  | 0.80 | nM |  |
| 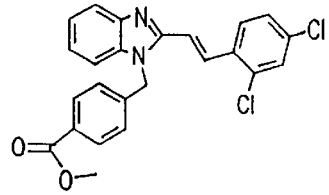 59-0141 | 437.33 |  |  |  |
|  |  | 100.00 | uM | −6.76 |
|  |  | 31.25 | uM | 5.69 |
|  |  | 9.77 | uM | 19.85 |
|  |  | 3.05 | uM | 43.96 |
|  |  | 953.67 | nM | 44.73 |
|  |  | 298.02 | nM | 37.12 |
|  |  | 93.13 | nM | 24.36 |
|  |  | 29.10 | nM | 18.6 |
|  |  | 9.09 | nM | 26.7 |
|  |  | 2.84 | nM | 15.96 |
|  |  | 0.80 | nM | 7.87 |
| 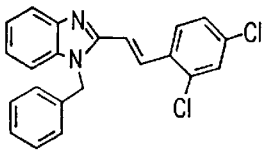 59-0142 | 379.29 |  |  |  |
|  |  | 100.00 | uM | 9.43 |
|  |  | 31.25 | uM | 33.72 |
|  |  | 9.77 | uM | 47.33 |
|  |  | 3.05 | uM | 40.19 |
|  |  | 953.67 | nM | 36.53 |
|  |  | 298.02 | uM | 29.94 |
|  |  | 93.13 | nM | 22.11 |
FIG. 3RR

| | | 29.10 | nM | 20.9 | |
|---|---|---|---|---|---|
| | | 9.09 | nM | 19.14 | |
| | | 2.84 | nM | 10.38 | |
| | | 0.80 | nM | 17.12 | |
| 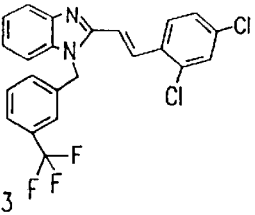 59-0143 | 447.29 | | | | |
| | | 100.00 | uM | 0.4 | |
| | | 31.25 | uM | 34.39 | |
| | | 9.77 | uM | 42.21 | |
| | | 3.05 | uM | 50.57 | |
| | | 953.67 | nM | 36.94 | |
| | | 298.02 | nM | 27.23 | |
| | | 93.13 | nM | 16.99 | |
| | | 29.10 | nM | 19.27 | |
| | | 9.09 | nM | 14.42 | |
| | | 2.84 | nM | 11.33 | |
| | | 0.80 | nM | 23.72 | |
| 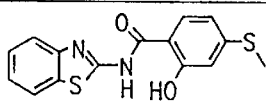 59-0144 | 316.40 | | | | |
| | | 100.00 | uM | −14.59 | |
| | | 31.25 | uM | −4.44 | |
| | | 9.77 | uM | 47.1 | |
| | | 3.05 | uM | 53.89 | |
| | | 953.67 | nM | 43.11 | |
| | | 298.02 | nM | 29.2 | |
| | | 93.13 | nM | 18.5 | |
| | | 29.10 | nM | 12.9 | |
| | | 9.09 | nM | 5.54 | |
| | | 2.84 | nM | 3.71 | |
| | | 0.80 | nM | 5.87 | |
| 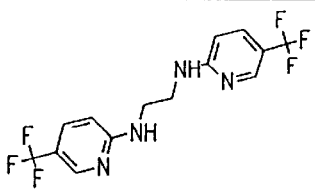 59-0145 | 350.27 | | | | |
| | | 100.00 | uM | 435.91 | |
| | | 31.25 | uM | 422.15 | |
| | | 9.77 | uM | 446.93 | |
| | | 3.05 | uM | 434.17 | |
| | | 953.67 | nM | 238.34 | |
| | | 298.02 | uM | 45.99 | |
| | | 93.13 | nM | 9.22 | |
| | | 29.10 | uM | 7.71 | |
| | | 9.09 | nM | 0.11 | |
FIG. 3SS

| | | 2.84 | nM | 6.27 | |
| | | 0.80 | nM | 3.55 | |
| 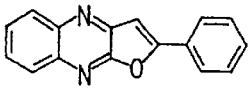 59-0146 | 246.27 | | | | |
| | | 100.00 | uM | −63.05 | |
| | | 31.25 | uM | 4.42 | |
| | | 9.77 | uM | −13.73 | |
| | | 3.05 | uM | −16.45 | |
| | | 953.67 | nM | −35.47 | |
| | | 298.02 | nM | −51.25 | |
| | | 93.13 | nM | −50.13 | |
| | | 29.10 | nM | −42.92 | |
| | | 9.09 | nM | −45.64 | |
| | | 2.84 | nM | −56.58 | |
| | | 0.80 | nM | −39.68 | |
| 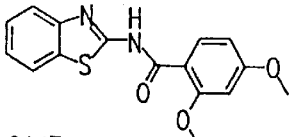 59-0147 | 314.36 | | | | |
| | | 100.00 | uM | −85 | |
| | | 31.25 | uM | −85 | |
| | | 9.77 | uM | −80.29 | |
| | | 3.05 | uM | −41.67 | |
| | | 953.67 | nM | 78.69 | |
| | | 298.02 | nM | 269.13 | |
| | | 93.13 | nM | 323.59 | |
| | | 29.10 | nM | 339.88 | |
| | | 9.09 | nM | 270.48 | |
| | | 2.84 | nM | 245.58 | |
| | | 0.80 | nM | 180.33 | |
| 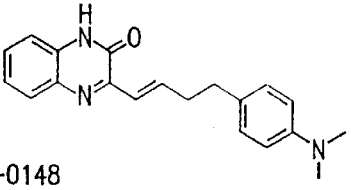 59-0148 | 291.35 | | | | |
| | | 100.00 | uM | −68.38 | |
| | | 31.25 | uM | −36.33 | |
| | | 9.77 | uM | −2.3 | |
| | | 3.05 | uM | 12.12 | |
| | | 953.67 | nM | −2.42 | |
| | | 298.02 | nM | −16.21 | |
| | | 93.13 | nM | −30.87 | |
| | | 29.10 | nM | −35.58 | |
| | | 9.09 | nM | −39.07 | |
| | | 2.84 | nM | −41.18 | |
| | | 0.80 | nM | −45.53 | |
FIG. 3TT

| | | | | |
|---|---|---|---|---|
| 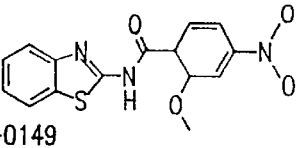 59-0149 | 329.33 | | | |
| | | 100.00 | uM | -16.9 |
| | | 31.25 | uM | -1.8 |
| | | 9.77 | uM | -0.53 |
| | | 3.05 | uM | 15.29 |
| | | 953.67 | nM | 78.78 |
| | | 298.02 | nM | 163.5 |
| | | 93.13 | nM | 223.57 |
| | | 29.10 | nM | 173.93 |
| | | 9.09 | nM | 122.3 |
| | | 2.84 | nM | 98.02 |
| | | 0.80 | nM | 69.06 |
| 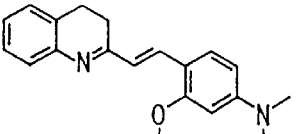 59-0150 | 304.39 | | | |
| | | 100.00 | uM | 63.32 |
| | | 31.25 | uM | 193.32 |
| | | 9.77 | uM | 419.26 |
| | | 3.05 | uM | 497.21 |
| | | 953.67 | nM | 295.19 |
| | | 298.02 | nM | 193.35 |
| | | 93.13 | nM | 99.46 |
| | | 29.10 | nM | 69.96 |
| | | 9.09 | nM | 59 |
| | | 2.84 | nM | 52.16 |
| | | 0.80 | nM | 48.75 |
| 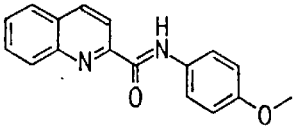 59-0151 | 278.311 | | | |
| 59-0151 | | 100.00 | uM | -6.660 |
| | | 31.25 | uM | 16.240 |
| | | 9.77 | uM | 18.300 |
| | | 3.05 | uM | 11.690 |
| | | 953.67 | nM | 8.500 |
| | | 298.02 | nM | 9.070 |
| | | 93.13 | nM | 6.110 |
| | | 29.10 | nM | 5.880 |
| | | 9.09 | nM | 7.700 |
| | | 2.84 | nM | 2.000 |
| | | 0.80 | nM | 1.210 |
FIG. 3UU

| | | | | | |
|---|---|---|---|---|---|
| 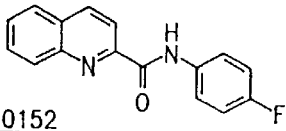 59-0152 | 266.275 | | | | |
| 59-0152 | | 100.00 | uM | -6.890 | |
| | | 31.25 | uM | 12.490 | |
| | | 9.77 | uM | 21.950 | |
| | | 3.05 | uM | 12.820 | |
| | | 953.67 | nM | 7.350 | |
| | | 298.02 | nM | 4.290 | |
| | | 93.13 | nM | 9.750 | |
| | | 29.10 | nM | 4.860 | |
| | | 9.09 | nM | 1.320 | |
| | | 2.84 | nM | 4.280 | |
| | | 0.80 | nM | 4.160 | |
| 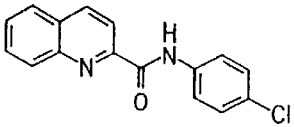 59-0153 | 282.73 | | | | |
| 59-0153 | | 100.00 | uM | -4.150 | |
| | | 31.25 | uM | -0.390 | |
| | | 9.77 | uM | 11.120 | |
| | | 3.05 | uM | 14.540 | |
| | | 953.67 | nM | 9.520 | |
| | | 298.02 | nM | 11.570 | |
| | | 93.13 | nM | -0.160 | |
| | | 29.10 | nM | 1.550 | |
| | | 9.09 | nM | -0.960 | |
| | | 2.84 | nM | 4.730 | |
| | | 0.80 | nM | 5.650 | |
| 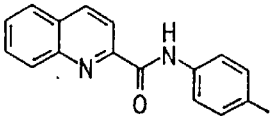 59-0154 | 262.312 | | | | |
| 59-0154 | | 100.00 | uM | 0.290 | |
| | | 31.25 | uM | 24.670 | |
| | | 9.77 | uM | 15.680 | |
| | | 3.05 | uM | 14.540 | |
| | | 953.67 | nM | 13.170 | |
| | | 298.02 | nM | 5.540 | |
| | | 93.13 | nM | 2.690 | |
| | | 29.10 | nM | -1.190 | |
| | | 9.09 | nM | 2.460 | |
| | | 2.84 | nM | 4.170 | |
| | | 0.80 | nM | 1.890 | |
FIG. 3VV

| | | | | | | |
|---|---|---|---|---|---|---|
| 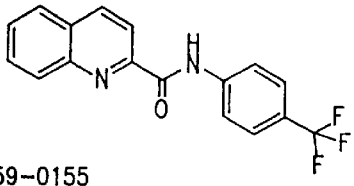 59-0155 | 316.282 | | | | | |
| 59-0155 | | 100.00 | uM | -2.950 | | |
| | | 31.25 | uM | 1.900 | | |
| | | 9.77 | uM | -9.450 | | |
| | | 3.05 | uM | -0.220 | | |
| | | 953.67 | nM | 0.690 | | |
| | | 298.02 | nM | 5.090 | | |
| | | 93.13 | nM | -3.250 | | |
| | | 29.10 | nM | 0.530 | | |
| | | 9.09 | nM | -1.900 | | |
| | | 2.84 | nM | 9.480 | | |
| | | 0.80 | nM | -1.130 | | |
| 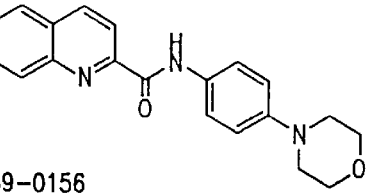 59-0156 | 333.391 | | | | | |
| 59-0156 | | 100.00 | uM | 5.840 | | |
| | | 31.25 | uM | 2.050 | | |
| | | 9.77 | uM | 7.960 | | |
| | | 3.05 | uM | 6.890 | | |
| | | 953.67 | nM | -0.370 | | |
| | | 298.02 | nM | -1.880 | | |
| | | 93.13 | nM | -3.550 | | |
| | | 29.10 | nM | -7.340 | | |
| | | 9.09 | nM | -1.590 | | |
| | | 2.84 | nM | 2.650 | | |
| | | 0.80 | nM | 2.500 | | |
| 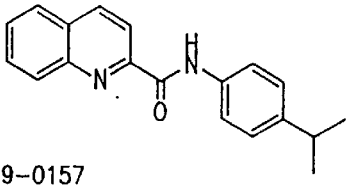 59-0157 | 290.366 | | | | | |
| 59-0157 | | 100.00 | uM | -6.440 | | |
| | | 31.25 | uM | 14.920 | | |
| | | 9.77 | uM | 19.930 | | |
| | | 3.05 | uM | 11.440 | | |
| | | 953.67 | nM | 8.570 | | |
| | | 298.02 | nM | -7.190 | | |
| | | 93.13 | nM | 0.080 | | |
| | | 29.10 | nM | -0.230 | | |
| | | 9.09 | nM | -4.460 | | |
| | | 2.84 | nM | 2.200 | | |
| | | 0.80 | nM | 9.920 | | |
FIG. 3WW

| | | | | | | |
|---|---|---|---|---|---|---|
| 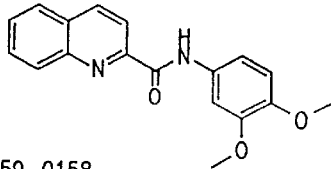 59-0158 | 308.337 | | | | | |
| 59-0158 | | 100.00 | uM | 5.980 | | |
| | | 31.25 | uM | 3.720 | | |
| | | 9.77 | uM | 16.140 | | |
| | | 3.05 | uM | 27.060 | | |
| | | 953.67 | nM | 9.930 | | |
| | | 298.02 | nM | 11.900 | | |
| | | 93.13 | nM | 2.810 | | |
| | | 29.10 | nM | 3.110 | | |
| | | 9.09 | nM | 0.690 | | |
| | | 2.84 | nM | 1.900 | | |
| | | 0.80 | nM | 7.970 | | |
| 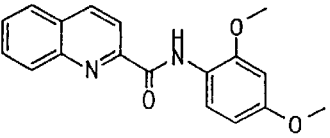 59-0159 | 308.337 | | | | | |
| 59-0159 | | 100.00 | uM | 2.790 | | |
| | | 31.25 | uM | 13.530 | | |
| | | 9.77 | uM | 4.700 | | |
| | | 3.05 | uM | 10.910 | | |
| | | 953.67 | nM | 2.800 | | |
| | | 298.02 | nM | 9.710 | | |
| | | 93.13 | nM | 4.830 | | |
| | | 29.10 | nM | 0.650 | | |
| | | 9.09 | nM | 5.900 | | |
| | | 2.84 | nM | 6.610 | | |
| | | 0.80 | nM | 6.250 | | |
| 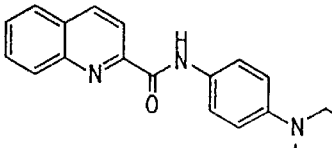 59-0160 | 319.408 | | | | | |
| 59-0160 | | 100.00 | uM | -5.060 | | |
| | | 31.25 | uM | -3.390 | | |
| | | 9.77 | uM | 5.300 | | |
| | | 3.05 | uM | 15.910 | | |
| | | 953.67 | nM | 6.610 | | |
| | | 298.02 | nM | 11.380 | | |
| | | 93.13 | nM | 4.460 | | |
| | | 29.10 | nM | 3.520 | | |
| | | 9.09 | nM | 4.700 | | |
| | | 2.84 | nM | -0.650 | | |
| | | 0.80 | nM | 7.560 | | |
FIG. 3XX

| | | | | | | | |
|---|---|---|---|---|---|---|---|
|  59-0196 | 323.201 | | | | | | |
| 59-0196 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
|  59-0197 | 323.201 | | | | | | |
| 59-0197 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 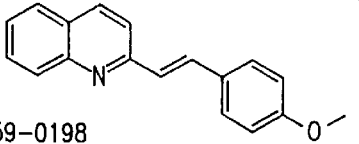 59-0198 | 261.324 | | | | | | |
| 59-0198 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 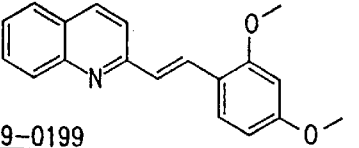 59-0199 | 291.35 | | | | | | |
| 59-0199 | | 100.00 | uM | | | | |
| | | 31.25 | uM | | | | |
FIG. 3YY

| | | | | | | | |
|---|---|---|---|---|---|---|---|
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 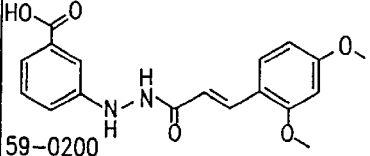 59-0200 | 342.351 | | | | | | |
| 59-0200 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 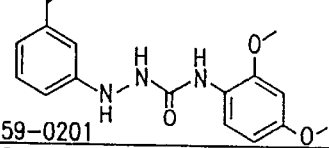 59-0201 | 331.328 | | | | | | |
| 59-0201 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 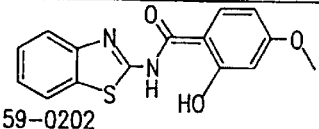 59-0202 | 300.336 | | | | | | |
| 59-0202 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
FIG. 3ZZ

| | | 9.09 | nM | | | | |
|---|---|---|---|---|---|---|---|
| | | 2.84 | nM | | | | |
| | | 0.80 | nM | | | | |
| 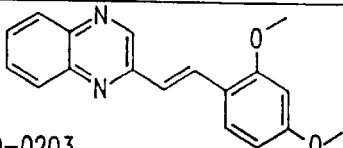 59-0203 | 292.338 | | | | | | |
| 59-0203 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 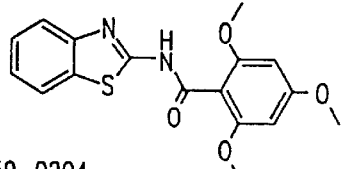 59-0204 | 344.389 | | | | | | |
| 59-0204 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 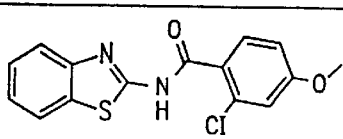 59-0205 | 318.782 | | | | | | |
| 59-0205 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
FIG. 3AAA

| | | | |
|---|---|---|---|
| 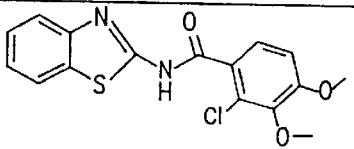 59-0206 | 348.808 | | |
| 59-0206 | | 100.00 | uM |
| | | 31.25 | uM |
| | | 9.77 | uM |
| | | 3.05 | uM |
| | | 953.67 | nM |
| | | 298.02 | nM |
| | | 93.13 | nM |
| | | 29.10 | nM |
| | | 9.09 | nM |
| | | 2.84 | nM |
| | | 0.80 | nM |
| 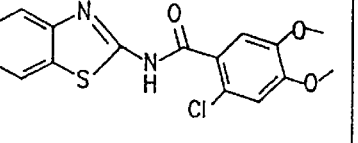 59-0207 | 348.808 | | |
| 59-0207 | | 100.00 | uM |
| | | 31.25 | uM |
| | | 9.77 | uM |
| | | 3.05 | uM |
| | | 953.67 | nM |
| | | 298.02 | nM |
| | | 93.13 | nM |
| | | 29.10 | nM |
| | | 9.09 | nM |
| | | 2.84 | nM |
| | | 0.80 | nM |
| 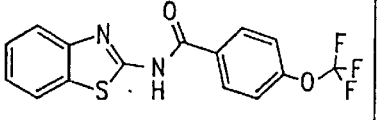 59-0208 | 338.307 | | |
| 59-0208 | | 100.00 | uM |
| | | 31.25 | uM |
| | | 9.77 | uM |
| | | 3.05 | uM |
| | | 953.67 | nM |
| | | 298.02 | nM |
| | | 93.13 | nM |
| | | 29.10 | nM |
| | | 9.09 | nM |
| | | 2.84 | nM |
| | | 0.80 | nM |
FIG. 3BBB

| | | | |
|---|---|---|---|
| 59-0209 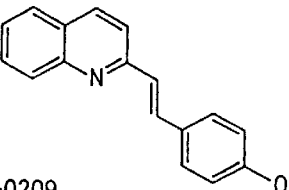 | 247.297 | | |
| 59-0209 | | 100.00 | uM |
| | | 31.25 | uM |
| | | 9.77 | uM |
| | | 3.05 | uM |
| | | 953.67 | nM |
| | | 298.02 | nM |
| | | 93.13 | nM |
| | | 29.10 | nM |
| | | 9.09 | nM |
| | | 2.84 | nM |
| | | 0.80 | nM |
| 59-0210 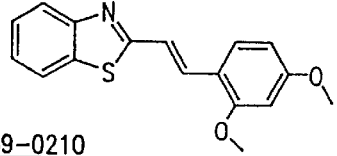 | 297.376 | | |
| 59-0210 | | 100.00 | uM |
| | | 31.25 | uM |
| | | 9.77 | uM |
| | | 3.05 | uM |
| | | 953.67 | nM |
| | | 298.02 | nM |
| | | 93.13 | nM |
| | | 29.10 | nM |
| | | 9.09 | nM |
| | | 2.84 | nM |
| | | 0.80 | nM |
| 59-8000 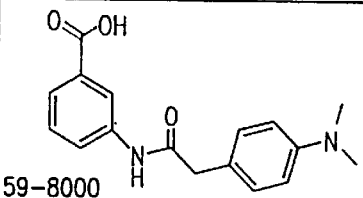 | 298.342 | | |
| 59-8000 | | 100.00 | uM |
| | | 31.25 | uM |
| | | 9.77 | uM |
| | | 3.05 | uM |
| | | 953.67 | nM |
| | | 298.02 | nM |
| | | 93.13 | nM |
| | | 29.10 | nM |
| | | 9.09 | nM |
| | | 2.84 | nM |
| | | 0.80 | nM |
FIG. 3CCC

| | | | | | | | |
|---|---|---|---|---|---|---|---|
| 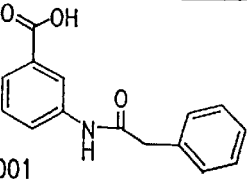 59-8001 | 255.273 | | | | | | |
| 59-8001 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 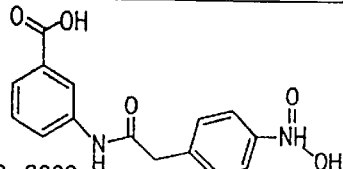 59-8002 | 302.286 | | | | | | |
| 59-8002 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 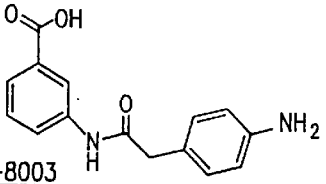 59-8003 | 270.288 | | | | | | |
| 59-8003 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
FIG. 3DDD

| Structure | MW | Conc | | | | | |
|---|---|---|---|---|---|---|---|
| 59-8004 | 331.371 | | | | | | |
| 59-8004 | | 100.00 uM | | | | | |
| | | 31.25 uM | | | | | |
| | | 9.77 uM | | | | | |
| | | 3.05 uM | | | | | |
| | | 953.67 nM | | | | | |
| | | 298.02 nM | | | | | |
| | | 93.13 nM | | | | | |
| | | 29.10 nM | | | | | |
| | | 9.09 nM | | | | | |
| | | 2.84 nM | | | | | |
| | | 0.80 nM | | | | | |
| 59-8005 | 299.326 | | | | | | |
| 59-8005 | | 100.00 uM | | | | | |
| | | 31.25 uM | | | | | |
| | | 9.77 uM | | | | | |
| | | 3.05 uM | | | | | |
| | | 953.67 nM | | | | | |
| | | 298.02 nM | | | | | |
| | | 93.13 nM | | | | | |
| | | 29.10 nM | | | | | |
| | | 9.09 nM | | | | | |
| | | 2.84 nM | | | | | |
| | | 0.80 nM | | | | | |
| 59-8006 | 327.38 | | | | | | |
| 59-8006 | | 100.00 uM | | | | | |
| | | 31.25 uM | | | | | |
| | | 9.77 uM | | | | | |
| | | 3.05 uM | | | | | |
| | | 953.67 nM | | | | | |
| | | 298.02 nM | | | | | |
| | | 93.13 nM | | | | | |
| | | 29.10 nM | | | | | |
| | | 9.09 nM | | | | | |
| | | 2.84 nM | | | | | |
| | | 0.80 nM | | | | | |

FIG. 3EEE

| | | | | | | | |
|---|---|---|---|---|---|---|---|
| 59-8007 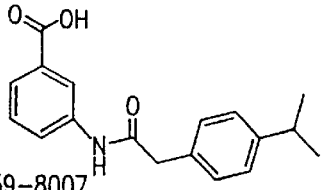 | 297.354 | | | | | | |
| 59-8007 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 59-8008 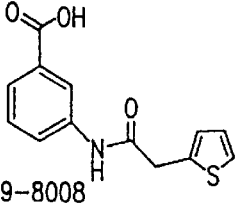 | 261.299 | | | | | | |
| 59-8008 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 59-8009 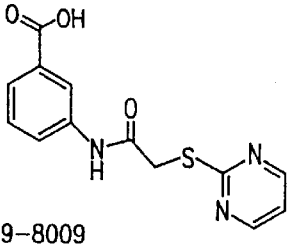 | 289.313 | | | | | | |
| 59-8009 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
FIG. 3FFF

| | | | | | | |
|---|---|---|---|---|---|---|
| | | 2.84 | nM | | | |
| | | 0.80 | nM | | | |
| 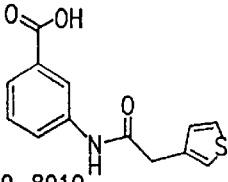 59-8010 | 261.299 | | | | | |
| 59-8010 | | 100.00 | uM | | | |
| | | 31.25 | uM | | | |
| | | 9.77 | uM | | | |
| | | 3.05 | uM | | | |
| | | 953.67 | nM | | | |
| | | 298.02 | nM | | | |
| | | 93.13 | nM | | | |
| | | 29.10 | nM | | | |
| | | 9.09 | nM | | | |
| | | 2.84 | nM | | | |
| | | 0.80 | nM | | | |
| 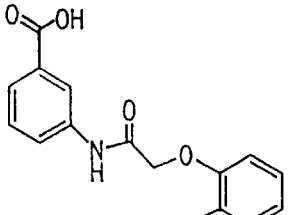 59-8011 | 285.299 | | | | | |
| 59-8011 | | 100.00 | uM | | | |
| | | 31.25 | uM | | | |
| | | 9.77 | uM | | | |
| | | 3.05 | uM | | | |
| | | 953.67 | nM | | | |
| | | 298.02 | nM | | | |
| | | 93.13 | nM | | | |
| | | 29.10 | nM | | | |
| | | 9.09 | nM | | | |
| | | 2.84 | nM | | | |
| | | 0.80 | nM | | | |
| 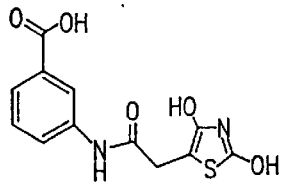 59-8012 | 294.285 | | | | | |
| 59-8012 | | 100.00 | uM | | | |
| | | 31.25 | uM | | | |
| | | 9.77 | uM | | | |
| | | 3.05 | uM | | | |
| | | 953.67 | nM | | | |
| | | 298.02 | nM | | | |
FIG. 3GGG

| | | | | | | |
|---|---|---|---|---|---|---|
| | | 93.13 nM | | | | |
| | | 29.10 nM | | | | |
| | | 9.09 nM | | | | |
| | | 2.84 nM | | | | |
| | | 0.80 nM | | | | |
| 59-8013 (structure) | 301.364 | | | | | |
| 59-8013 | | 100.00 uM | | | | |
| | | 31.25 uM | | | | |
| | | 9.77 uM | | | | |
| | | 3.05 uM | | | | |
| | | 953.67 nM | | | | |
| | | 298.02 nM | | | | |
| | | 93.13 nM | | | | |
| | | 29.10 nM | | | | |
| | | 9.09 nM | | | | |
| | | 2.84 nM | | | | |
| | | 0.80 nM | | | | |
| 59-8014 (structure) | 377.396 | | | | | |
| 59-8014 | | 100.00 uM | | | | |
| | | 31.25 uM | | | | |
| | | 9.77 uM | | | | |
| | | 3.05 uM | | | | |
| | | 953.67 nM | | | | |
| | | 298.02 nM | | | | |
| | | 93.13 nM | | | | |
| | | 29.10 nM | | | | |
| | | 9.09 nM | | | | |
| | | 2.84 nM | | | | |
| | | 0.80 nM | | | | |
| 59-8015 (structure) | 285.299 | | | | | |
| 59-8015 | | 100.00 uM | | | | |
| | | 31.25 uM | | | | |
| | | 9.77 uM | | | | |
| | | 3.05 uM | | | | |

FIG. 3HHH

| | | | | | | |
|---|---|---|---|---|---|---|
| | | 953.67 | nM | | | |
| | | 298.02 | nM | | | |
| | | 93.13 | nM | | | |
| | | 29.10 | nM | | | |
| | | 9.09 | nM | | | |
| | | 2.84 | nM | | | |
| | | 0.80 | nM | | | |
| 59-8016 (structure) | 285.299 | | | | | |
| 59-8016 | | 100.00 | uM | | | |
| | | 31.25 | uM | | | |
| | | 9.77 | uM | | | |
| | | 3.05 | uM | | | |
| | | 953.67 | nM | | | |
| | | 298.02 | nM | | | |
| | | 93.13 | nM | | | |
| | | 29.10 | nM | | | |
| | | 9.09 | nM | | | |
| | | 2.84 | nM | | | |
| | | 0.80 | nM | | | |

FIG. 3III

| CHEMISTRY | CONCENTRATION | | ABA-S |
|---|---|---|---|
| 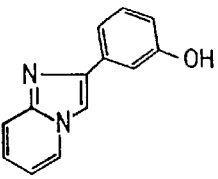 51-2229 | | | |
| 51-2229 | 100.00 | uM | 125.320 |
| | 10.00 | | 28.260 |
| 210.236 | 2.00 | | 20.140 |
| | 0.40 | | -9.740 |
| | 0.08 | | -9.710 |
| 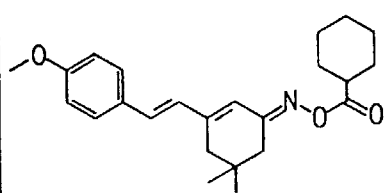 92-3052 | | | |
| 92-3052 | 131.056 | uM | -9.28 |
| | 13.106 | | 113.80 |
| 381.516 | 2.621 | | 12.61 |
| | 0.524 | | 20.25 |
| | 0.105 | | 24.45 |
| 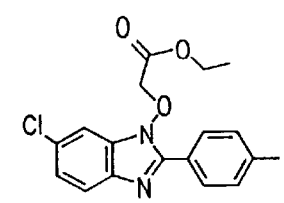 92-3390 | | | |
| 92-3390 | 145.012 | uM | -8.05 |
| | 14.501 | | 31.57 |
| 344.798 | 2.900 | | 139.68 |
| | 0.580 | | 49.82 |
| | 0.116 | | 21.01 |
| 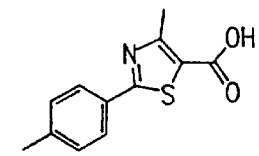 92-3552 | | | |
| 92-3552 | 214.326 | uM | 108.15 |
FIG. 4A

| | | | | |
|---|---|---|---|---|
| | | | 21.433 | | 69.74 |
| | | 233.289 | 4.287 | | 31.59 |
| | | | 0.857 | | 39.70 |
| | | | 0.171 | | 18.29 |
| 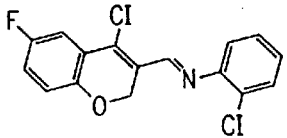 92-6353 | | | | | |
| 92-6353 | | | 155.199 | uM | |
| | | | 31.040 | | 204.14 |
| | | 322.166 | 15.520 | | 154.94 |
| | | | 3.104 | | 28.09 |
| | | | 1.552 | | |
| | | | 0.310 | | 3.53 |
| 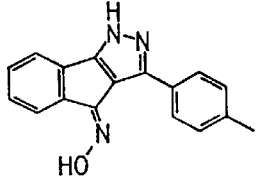 92-8007 | | | | | |
| 92-8007 | | | 181.613 | uM | |
| | | | 36.323 | | −16.65 |
| | | 275.311 | 18.161 | | 58.65 |
| | | | 3.632 | | 142.33 |
| | | | 1.816 | | 45.65 |
| | | | 0.363 | | 4.47 |
| 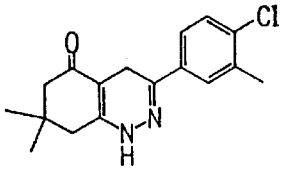 92-8215 | | | | | |
| 92-8215 | | | 165.123 | uM | |
| | | | 33.025 | | 32.90 |
| | | 302.805 | 16.512 | | 151.06 |
| | | | 3.302 | | 132.29 |
| | | | 1.651 | | 59.90 |
| | | | 0.330 | | 23.34 |
FIG. 4B

| | | | | |
|---|---|---|---|---|
| 92-8258 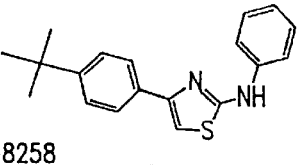 | | | | |
| 92-8258 | | 162.102 | uM | −16.65 |
| | | 32.420 | | 157.44 |
| | 308.447 | 16.210 | | 101.04 |
| | | 3.242 | | 39.02 |
| | | 1.621 | | |
| | | 0.324 | | 12.78 |
| 92-8362 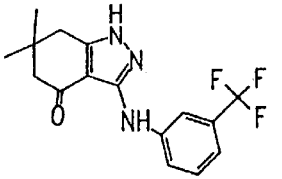 | | | | |
| 92-8362 | | 154.647 | uM | 136.79 |
| | | 30.929 | | 137.00 |
| | 323.318 | 15.465 | | 65.02 |
| | | 3.093 | | 17.34 |
| | | 1.546 | | |
| | | 0.309 | | 0.41 |
| 92-8372 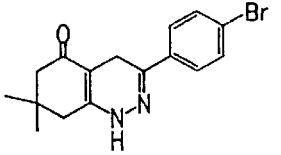 | | | | |
| 92-8372 | | 150.045 | uM | 63.76 |
| | | 30.009 | | 134.71 |
| | 333.234 | 15.004 | | 92.06 |
| | | 3.001 | | 31.35 |
| | | 1.500 | | |
| | | 0.300 | | 13.20 |
| 92-9183 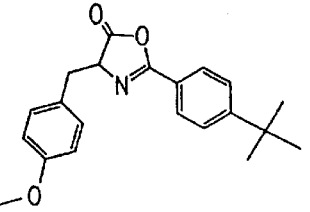 | | | | |
FIG. 4C

| ID | MW | Value | Unit | Value2 |
|---|---|---|---|---|
| 92-9183 | | 137.568 | uM | -22.80 |
| | | 13.757 | | 16.61 |
| | 363.457 | 2.751 | | 101.96 |
| | | 1.376 | | |
| | | 0.550 | | 58.17 |
| | | 0.110 | | 38.47 |
93-0215
| ID | MW | Value | Unit | Value2 |
|---|---|---|---|---|
| 93-0215 | | 182.957 | uM | 115.230 |
| | | 18.296 | | 88.110 |
| | 273.288 | 3.659 | | 20.870 |
| | | 0.732 | | -28.680 |
| | | 0.146 | | 5.250 |
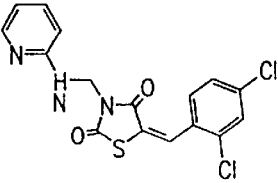
93-0399
| ID | MW | Value | Unit | Value2 |
|---|---|---|---|---|
| 93-0399 | | 131.491 | uM | 128.130 |
| | | 13.149 | | 38.560 |
| | 380.253 | 2.630 | | 41.240 |
| | | 0.526 | | -4.910 |
| | | 0.105 | | 3.910 |
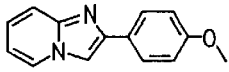
93-0587
| ID | MW | Value | Unit | Value2 |
|---|---|---|---|---|
| 93-0587 | | 222.953 | uM | 178.130 |
| | | 22.295 | | 60.410 |
| | 224.263 | 4.459 | | -0.180 |
| | | 0.892 | | -3.470 |
| | | 0.178 | | -8.460 |
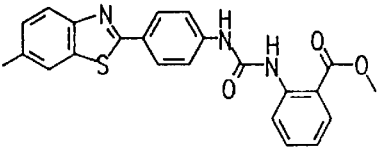
93-1327
| ID | MW | Value | Unit | Value2 |
|---|---|---|---|---|
| 93-1327 | | 119.764 | uM | -42.000 |
| | | 11.976 | | 119.130 |
| | 417.487 | 2.395 | | 67.930 |
| | | 0.479 | | 8.520 |
FIG. 4D

| | | 0.096 | | 14.870 |
|---|---|---|---|---|
| 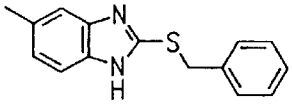 93-1340 | | | | |
| 93-1340 | | 196.576 | uM | -31.290 |
| | | 19.658 | | 127.340 |
| | 254.355 | 3.932 | | 35.710 |
| | | 0.786 | | 37.630 |
| | | 0.157 | | 7.280 |
| 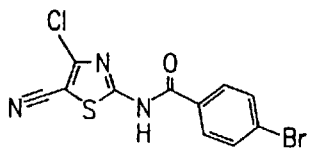 93-1474 | | | | |
| 93-1474 | | 145.940 | uM | -45.110 |
| | | 14.594 | | 110.290 |
| | 342.607 | 2.919 | | 35.080 |
| | | 0.584 | | 109.040 |
| | | 0.117 | | 40.130 |
| 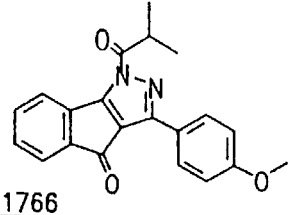 93-1766 | | | | |
| 93-1766 | | 144.348 | uM | |
| | | 14.435 | | |
| | 346.366 | 2.887 | | |
| | | 0.577 | | |
| | | 0.115 | | |
| 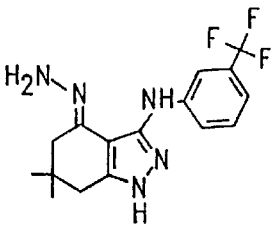 93-1866 | | | | |
| 93-1866 | | 148.214 | uM | 75.940 |
| | | 14.821 | | 173.150 |
FIG. 4E

| | | | |
|---|---|---|---|
| 850-7377 | | | |
| 850-7377 | | 131.062 | uM |
| | | 13.106 | |
| | 381.498 | 2.621 | |
| | | 0.524 | |
| | | 0.105 | |
| 850-7413 | | | |
| 850-7413 | | 111.964 | uM |
| | | 11.196 | |
| | 446.572 | 2.239 | |
| | | 0.448 | |
| | | 0.090 | |
| 850-7449 | | | |
| 850-7449 | | 69.938 | uM |
| | | 6.994 | |
| | 714.923 | 1.399 | |
| | | 0.280 | |
| | | 0.056 | |

| |
|---|
| −50.32 |
| 68.27 |
| 116.61 |
| 61.26 |
| 25.86 |
| −40.44 |
| −2.55 |
| 157.01 |
| 78.73 |
| 23.91 |
| −42.42 |
| 73.79 |
| 112.16 |
| 75.24 |
| 26.36 |

FIG. 4F

| | | | |
|---|---|---|---|
| 93-7485 | | | |
| 93-7485 | 143.099 | uM | -42.91 |
| | 14.310 | | 28.36 |
| 349.409 | 2.862 | | 153.04 |
| | 0.572 | | 74.27 |
| | 0.114 | | 50.28 |
| 93-7991 | | | |
| 93-7991 | 127.367 | uM | -16.87 |
| | 12.737 | | 8.95 |
| 392.585 | 2.547 | | 105.51 |
| | 0.509 | | 47.53 |
| | 0.102 | | 54.26 |
| 850-8170 | | | |
| 850-8170 | 101.513 | uM | -33.79 |
| | 10.151 | | 158.65 |
| 492.55 | 2.030 | | 126.27 |
| | 0.406 | | 43.05 |
| | 0.061 | | 50.00 |

FIG. 4G

| | | | |
|---|---|---|---|
| 850-8205 | | | |
| 850-8205 | | 104.478 | uM | -39.52 |
| | | 10.448 | | 51.18 |
| | 478.57 | 2.090 | | 163.82 |
| | | 0.418 | | 106.06 |
| | | 0.084 | | 73.68 |
| CHIRAL 850-8241 | | | |
| 850-8241 | | 82.279 | uM | -2.07 |
| | | 8.226 | | 181.77 |
| | 607.685 | 1.646 | | 118.23 |
| | | 0.329 | | 66.73 |
| | | 0.066 | | 36.14 |
| 850-8278 | | | |
| 850-8278 | | 139.101 | uM | -40.09 |
| | | 13.910 | | 39.00 |
| | 359.451 | 2.782 | | 182.38 |
| | | 0.556 | | 122.84 |
| | | 0.111 | | 78.90 |
| 850-8367 | | | |

FIG. 4H

| | | | | |
|---|---|---|---|---|
| 850-8387 | | 122.392 | uM | -17.06 |
| | | 12.239 | | 130.31 |
| | 408.523 | 2.448 | | 129.75 |
| | | 0.490 | | 62.69 |
| | | 0.098 | | 40.74 |
| 850-8459 (structure) | | | | |
| 850-8459 | | 87.921 | uM | -21.13 |
| | | 8.792 | | 11.30 |
| | 568.692 | 1.758 | | 131.92 |
| | | 0.352 | | 71.13 |
| | | 0.070 | | 58.55 |
| 850-8613 (structure) | | | | |
| 850-8613 | | 151.319 | uM | -26.05 |
| | | 15.132 | | 85.55 |
| | 330.428 | 3.026 | | 381.37 |
| | | 0.605 | | 255.32 |
| | | 0.121 | | 122.93 |
| 850-8637 (structure) | | | | |
| 850-8637 | | 85.518 | uM | -25.17 |
| | | 8.552 | | 33.35 |
| | 584.673 | 1.710 | | 122.49 |
| | | 0.342 | | 57.19 |
| | | 0.068 | | 37.42 |

FIG. 4I

| | | 0.088 | | 23.540 |
|---|---|---|---|---|
| 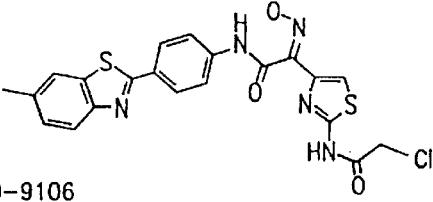 850-9106 | | | | |
| 850-9106 | | 100.000 | uM | -15.710 |
| | | 10.000 | | 99.820 |
| | 499.999 | 2.000 | | 111.960 |
| | | 0.400 | | 74.500 |
| | | 0.080 | | 23.150 |
| 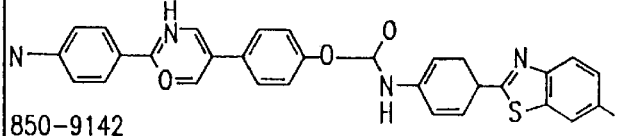 850-9142 | | | | |
| 850-9142 | | 85.596 | uM | -14.980 |
| | | 8.560 | | 165.770 |
| | 584.138 | 1.712 | | 66.650 |
| | | 0.342 | | 27.780 |
| | | 0.068 | | 0.670 |
| 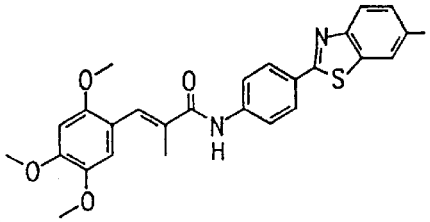 850-9179 | | | | |
| 850-9179 | | 105.357 | uM | -24.630 |
| | | 10.536 | | 105.200 |
| | 474.579 | 2.107 | | 89.280 |
| | | 0.421 | | 46.110 |
| | | 0.064 | | 19.160 |
| 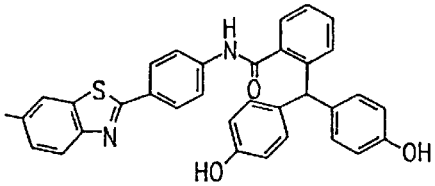 850-9212 | | | | |
| 850-9212 | | 92.139 | uM | -26.580 |
| | | 9.214 | | 40.900 |
| | 542.657 | 1.843 | | 111.690 |
| | | 0.369 | | 76.950 |
| | | 0.074 | | 30.840 |
FIG. 4K

| | | | |
|---|---|---|---|
| 850-9287 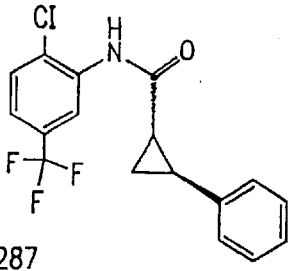 | | | |
| 850-9287 | 147.170 | uM | -15.82 |
| | 14.717 | | 15.82 |
| 339.744 | 2.943 | | 130.71 |
| | 0.589 | | 91.11 |
| | 0.118 | | 69.05 |
| 850-9356 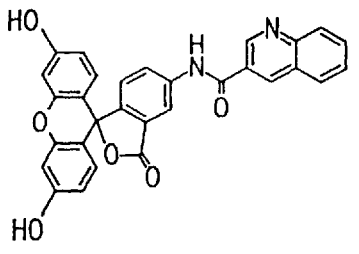 | | | |
| 850-9356 | 99.506 | uM | -24.650 |
| | 9.951 | | 83.140 |
| 502.482 | 1.990 | | 168.810 |
| | 0.396 | | 45.470 |
| | 0.080 | | 9.740 |
| 850-9467 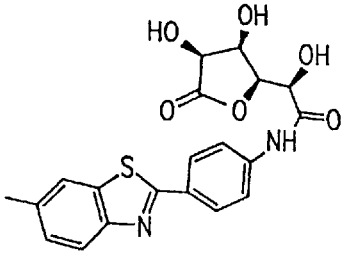 | | | |
| 850-9467 | 120.646 | uM | -19.800 |
| | 12.065 | | 112.990 |
| 414.436 | 2.413 | | 122.730 |
| | 0.483 | | 43.520 |
| | 0.097 | | 33.140 |
FIG. 4L

| | | | |
|---|---|---|---|
| 895-0594 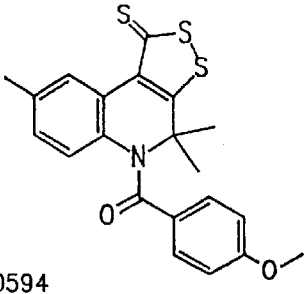 | | | |
| 895-0594 | 120.896 | uM | -21.63 |
| | 12.090 | | 25.89 |
| 413.58 | 2.418 | | 122.10 |
| | 0.484 | | 75.32 |
| | 0.097 | | 39.42 |
| 895-0857 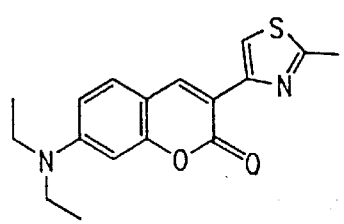 | | | |
| 895-0857 | 159.026 | uM | -30.46 |
| | 15.903 | | 146.74 |
| 314.407 | 3.181 | | 74.54 |
| | 0.636 | | 25.82 |
| | 0.127 | | 3.66 |
| 895-0964 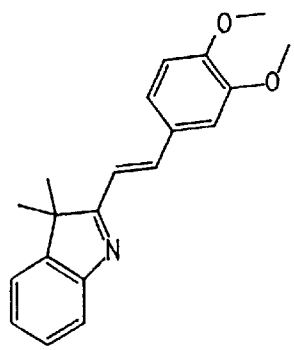 | | | |
| 895-0964 | 162.655 | uM | -31.06 |
| | 16.265 | | 325.06 |
| 307.393 | 3.253 | | 87.51 |
| | 0.651 | | 40.39 |
| | 0.130 | | 16.03 |
FIG. 4N

| | | | |
|---|---|---|---|
| 895-1161 | | | |
| 895-1161 | 152.625 | uM | -5.51 |
| | 15.263 | | 109.31 |
| 327.602 | 3.053 | | 56.06 |
| | 0.611 | | 29.49 |
| | 0.122 | | 24.71 |
| 895-1420 | | | |
| 895-1420 | 220.965 | uM | -19.47 |
| | 22.097 | | 110.90 |
| 226.279 | 4.419 | | 49.94 |
| | 0.884 | | 33.65 |
| | 0.177 | | 20.06 |
| 895-1679 | | | |
| 895-1679 | 180.910 | uM | -30.36 |
| | 18.091 | | 111.72 |
| 276.383 | 3.618 | | 102.83 |
| | 0.724 | | 18.01 |
| | 0.145 | | 0.44 |
| 895-1691 | | | |
| 895-1691 | 182.992 | uM | -16.29 |
| | 18.292 | | 50.84 |
| 273.34 | 3.658 | | 105.70 |

FIG. 40

| | | | |
|---|---|---|---|
| | | 0.732 | 60.23 |
| | | 0.146 | 23.42 |
| 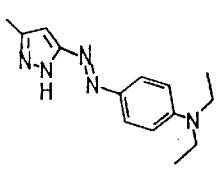 895-1754 | | | |
| 895-1754 | | 194.295 uM | -31.44 |
| | | 19.430 | 132.78 |
| | 257.341 | 3.886 | 75.39 |
| | | 0.777 | 39.30 |
| | | 0.155 | 16.19 |
| 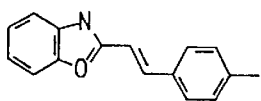 895-1888 | | | |
| 895-1888 | | 212.504 uM | -33.65 |
| | | 21.250 | 29.75 |
| | 235.286 | 4.250 | 148.84 |
| | | 0.850 | 73.77 |
| | | 0.170 | 28.14 |
| 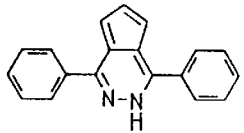 895-2474 | | | |
| 895-2474 | | 184.952 uM | -20.74 |
| | | 18.495 | 128.69 |
| | 270.335 | 3.699 | 66.37 |
| | | 0.740 | 43.27 |
| | | 0.148 | 19.44 |
| 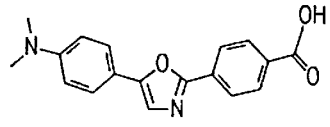 895-2475 | | | |
| 895-2475 | | 162.159 uM | 265.41 |
| | | 16.216 | 287.86 |
| | 308.337 | 3.243 | 227.34 |
| | | 0.649 | 65.40 |
| | | 0.130 | 28.96 |
FIG. 4P

| Structure | ID | Value | Unit | | Value |
|---|---|---|---|---|---|
| [5-phenyloxazol-2-yl phenyl N-OH oxime] | 895-2544 | | | | |
| | 895-2544 | 189.186 | uM | | 17.53 |
| | | 18.919 | | | 136.50 |
| | 264.284 | 3.784 | | | 59.15 |
| | | 0.757 | | | 24.75 |
| | | 0.151 | | | 11.86 |
| [acetyl diphenyl cyclopenta pyridazine] | 895-3113 | | | | |
| | 895-3113 | 160.067 | uM | | -22.22 |
| | | 16.007 | | | 224.52 |
| | 312.372 | 3.201 | | | 68.46 |
| | | 0.640 | | | 43.36 |
| | | 0.128 | | | 30.56 |
| [dimethylindoline vinyl dimethylaniline] | 895-3306 | | | | |
| | 895-3306 | 172.170 | uM | | -23.24 |
| | | 17.217 | | | 38.63 |
| | 290.41 | 3.443 | | | 333.10 |
| | | 0.689 | | | 164.63 |
| | | 0.136 | | | 64.33 |
| [indolin-2-one hydrazone o-tolyl] | 895-3810 | | | | |
| | 895-3810 | 196.973 | uM | | 89.79 |
| | | 19.897 | | | 106.75 |
| | 251.289 | 3.979 | | | 73.78 |
| | | 0.796 | | | 33.45 |
| | | 0.159 | | | 16.86 |

FIG. 4Q

| | | | | |
|---|---|---|---|---|
| 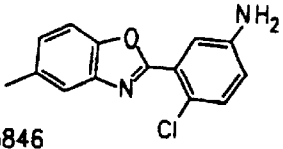 | | | | |
| 895-3846 | | | | |
| 895-3846 | | 193.267 | uM | -21.41 |
| | | 19.327 | | 13.40 |
| | 258.708 | 3.865 | | 114.46 |
| | | 0.773 | | 52.12 |
| | | 0.155 | | 38.29 |
| 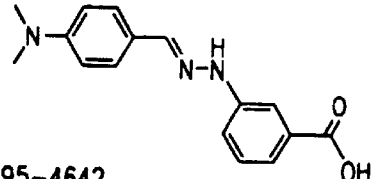 | | | | |
| 895-4642 | | | | |
| 895-4642 | | 176.473 | uM | 6.97 |
| | | 17.647 | | 383.99 |
| | 283.331 | 3.529 | | 447.51 |
| | | 0.706 | | 304.86 |
| | | 0.141 | | 100.45 |
| 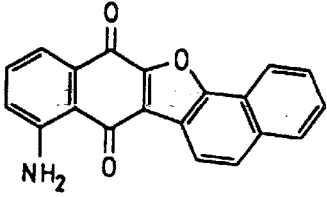 | | | | |
| 895-4843 | | | | |
| 895-4843 | | 159.581 | uM | -17.18 |
| | | 15.958 | | 24.54 |
| | 313.312 | 3.192 | | 100.12 |
| | | 0.638 | | 60.37 |
| | | 0.128 | | 27.85 |
| 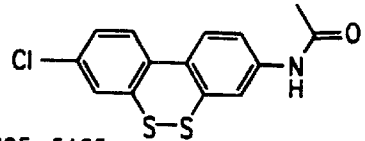 | | | | |
| 895-5185 | | | | |
| 895-5185 | | 162.433 | uM | -6.47 |
| | | 16.243 | | 213.42 |
| | 307.821 | 3.249 | | 107.83 |
| | | 0.650 | | 46.75 |
| | | 0.130 | | 18.27 |
FIG. 4R

| | | | |
|---|---|---|---|
| <br>895-5960 | | | |
| 895-5960 | | 103.348 | uM | -10.03 |
| | | 10.335 | | 156.04 |
| | 483.796 | 2.067 | | 62.07 |
| | | 0.413 | | 34.47 |
| | | 0.083 | | 7.24 |
| <br>895-6353 | | | |
| 895-6353 | | 167.555 | uM | -10.45 |
| | | 16.755 | | 21.59 |
| | 298.408 | 3.351 | | 101.77 |
| | | 0.670 | | 54.91 |
| | | 0.134 | | 24.15 |
| <br>895-6643 | | | |
| 895-6643 | | 145.862 | uM | 100.09 |
| | | 14.586 | | 74.25 |
| | 342.786 | 2.917 | | 16.86 |
| | | 0.583 | | -0.89 |
| | | 0.117 | | -7.94 |
| <br>895-7828 | | | |
| 895-7828 | | 184.973 | uM | -32.44 |
| | | 18.497 | | -29.24 |
| | 270.31 | 3.699 | | 85.15 |
| | | 0.740 | | 125.64 |
| | | 0.148 | | -30.80 |
FIG. 4S

| Structure | | | | |
|---|---|---|---|---|
| 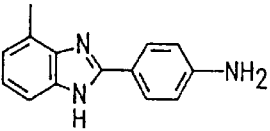 895-7985 | | | | |
| 895-7985 | | | 223.935 uM | 122.070 |
| | | | 22.394 | 3.900 |
| | | 223.279 | 4.479 | -7.790 |
| | | | 0.896 | 5.520 |
| | | | 0.179 | -2.270 |
| 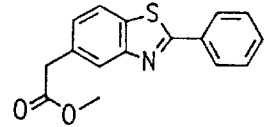 895-7997 | | | | |
| 895-7997 | | | 176.461 uM | |
| | | | 17.646 | |
| | | 283.349 | 3.529 | |
| | | | 0.706 | |
| | | | 0.141 | |
| 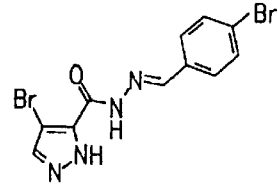 895-8053 | | | | |
| 895-8053 | | | 134.398 uM | |
| | | | 13.440 | |
| | | 372.03 | 2.666 | |
| | | | 0.538 | |
| | | | 0.108 | |
| 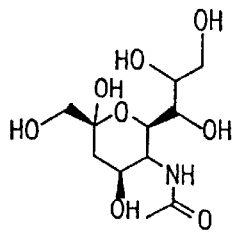 895-8137 | | | | |
| 895-8137 | | | 169.326 uM | |
FIG. 4T

| | | | |
|---|---|---|---|
| | | 16.933 | |
| | 295.288 | 3.387 | |
| | | 0.677 | |
| | | 0.135 | |
| 895-8185 [structure] | | | |
| 895-8185 | | 219.057 | uM |
| | | 21.906 | |
| | 228.251 | 4.361 | |
| | | 0.876 | |
| | | 0.175 | |
| 895-8286 [structure] | | | |
| 895-8286 | | 142.765 | uM |
| | | 14.277 | |
| | 350.225 | 2.855 | |
| | | 0.571 | |
| | | 0.114 | |
| 895-8383 [structure] | | | |
| 895-8383 | | 191.774 | uM |
| | | 19.177 | |
| | 260.724 | 3.835 | |
| | | 0.767 | |
| | | 0.153 | |

| |
|---|
| |
| |
| |
| |
| 142.210 |
| 40.390 |
| 17.850 |
| −10.890 |
| 6.580 |
| |
| −44.020 |
| 76.480 |
| 135.940 |
| 77.030 |
| 37.630 |

FIG. 4U

| | | | |
|---|---|---|---|
| 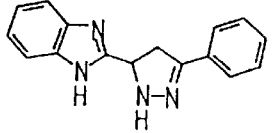 896-0122 | | | |
| 896-0122 | | 190.610 | uM | -14.15 |
| | | 19.061 | | 151.42 |
| | 262.316 | 3.812 | | 56.90 |
| | | 0.762 | | 19.20 |
| | | 0.152 | | 11.42 |
| 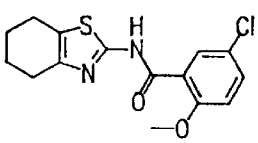 896-0246 | | | |
| 896-0246 | | 154.888 | uM | -17.57 |
| | | 15.489 | | 34.35 |
| | 322.814 | 3.096 | | 102.03 |
| | | 0.620 | | 46.52 |
| | | 0.124 | | 20.52 |
| 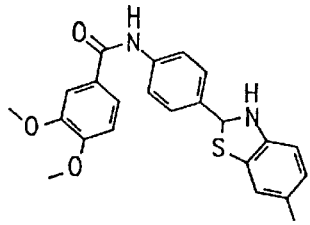 896-0255 | | | |
| 896-0255 | | 123.000 | uM | -17.14 |
| | | 12.300 | | 67.75 |
| | 406.504 | 2.480 | | 168.78 |
| | | 0.492 | | 61.27 |
| | | 0.098 | | 49.97 |
| 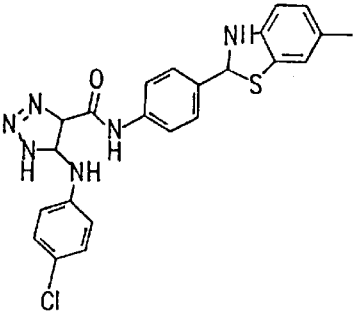 896-0345 | | | |
| 896-0345 | | 107.532 | uM | -18.86 |
| | | 10.753 | | 77.80 |
FIG. 4W

| | 464.979 | 2.151 | | 188.94 |
|---|---|---|---|---|
| | | 0.430 | | 106.12 |
| | | 0.086 | | 37.18 |
| 896-0390 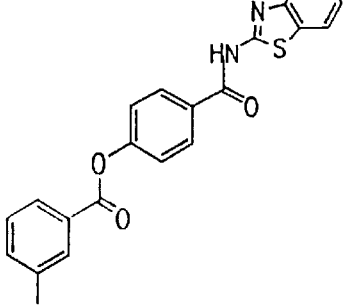 | | | | |
| 896-0390 | | 128.718 | uM | -16.90 |
| | | 12.872 | | 87.23 |
| | 388.445 | 2.574 | | 210.25 |
| | | 0.515 | | 73.35 |
| | | 0.103 | | 28.25 |
| 896-0535 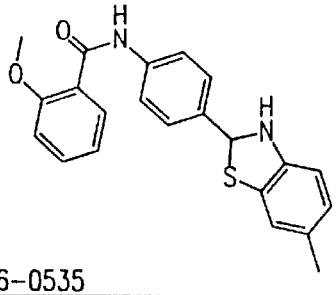 | | | | |
| 896-0535 | | 132.810 | uM | -10.41 |
| | | 13.281 | | 73.84 |
| | 376.478 | 2.656 | | 199.80 |
| | | 0.531 | | 102.12 |
| | | 0.106 | | 35.72 |
| 896-0554 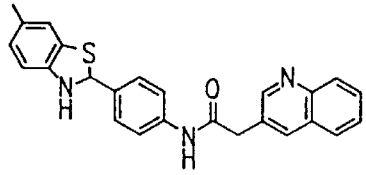 | | | | |
| 896-0554 | | 121.499 | uM | -16.32 |
| | | 12.150 | | 105.48 |
| | 411.527 | 2.430 | | 115.43 |
| | | 0.486 | | 53.88 |
| | | 0.097 | | 27.03 |
FIG. 4X

| Structure | | | |
|---|---|---|---|
| 896-0686 | | | |
| 896-0686 | | 191.774 | uM | -19.80 |
| | | 19.177 | | 176.04 |
| | 260.724 | 3.835 | | 115.02 |
| | | 0.767 | | 97.67 |
| | | 0.153 | | 25.27 |
| 896-0692 | | | |
| 896-0692 | | 131.269 | uM | 22.78 |
| | | 13.127 | | 149.23 |
| | 380.897 | 2.625 | | 78.33 |
| | | 0.525 | | 51.06 |
| | | 0.105 | | 46.12 |
| 896-0719 | | | |
| 896-0719 | | 91.950 | uM | -6.49 |
| | | 9.195 | | 187.43 |
| | 543.774 | 1.839 | | 127.43 |
| | | 0.366 | | 50.04 |
| | | 0.074 | | 36.16 |
| 896-0773 | | | |
| 896-0773 | | 147.228 | uM | -13.94 |
| | | 14.723 | | 175.33 |
| | 339.609 | 2.945 | | 221.91 |
| | | 0.589 | | 52.48 |
| | | 0.118 | | 32.99 |

FIG. 4Y

| Compound | | | | |
|---|---|---|---|---|
| 896-0819 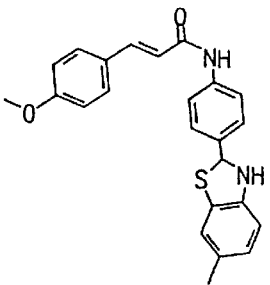 | | | | |
| 896-0819 | | 124.219 | uM | -16.20 |
| | | 12.422 | | 70.03 |
| | 402.516 | 2.484 | | 165.79 |
| | | 0.497 | | 82.61 |
| | | 0.099 | | 49.06 |
| 896-0853 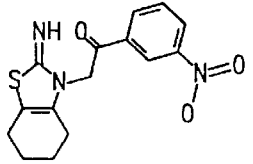 | | | | |
| 896-0853 | | 157.546 | uM | -27.06 |
| | | 15.755 | | 75.38 |
| | 317.367 | 3.151 | | 208.69 |
| | | 0.630 | | 33.08 |
| | | 0.126 | | 32.63 |
| 896-0921 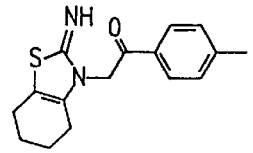 | | | | |
| 896-0921 | | 174.583 | uM | -19.59 |
| | | 17.458 | | 44.07 |
| | 266.397 | 3.492 | | 103.23 |
| | | 0.698 | | 54.02 |
| | | 0.140 | | 23.86 |
FIG. 4Z

| | | | | |
|---|---|---|---|---|
| 896-0936 [structure] | | | | |
| 896-0936 | | 184.314 | uM | -16.20 |
| | | 18.431 | | 153.61 |
| | 271.276 | 3.686 | | 184.53 |
| | | 0.737 | | 79.16 |
| | | 0.147 | | 32.61 |
| 896-0959 [structure] | | | | |
| 896-0959 | | 103.796 | uM | -1.73 |
| | | 10.380 | | 102.48 |
| | 461.703 | 2.076 | | 61.61 |
| | | 0.415 | | 63.56 |
| | | 0.083 | | 48.27 |
| 896-1201 [structure] | | | | |
| 896-1201 | | 106.343 | uM | -45.70 |
| | | 10.834 | | 92.57 |
| | 461.496 | 2.167 | | 191.83 |
| | | 0.433 | | 47.22 |
| | | 0.087 | | 58.25 |

FIG. 4AA

59-0199
MAX: 170%
EC50: 100 nM 59-0203
MAX: 275%
EC50: <1 nM 59-0286
MAX: 160%
EC50: 300 nM 59-0285
MAX: 200%
EC50: 30 nM

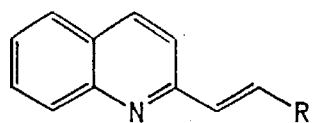
R=
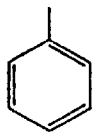
59-0030
MAX: 90%
EC50: 1 uM
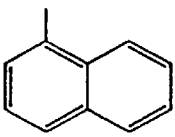
59-0089
MAX: 120%
EC50: 5 uM
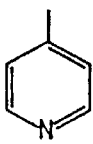
59-0093
MAX: 35%
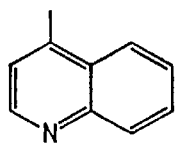
59-0094
MAX: 45%
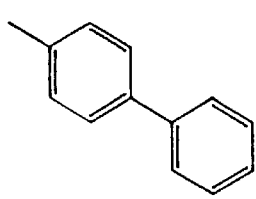
59-0091
MAX: 96%
EC50: 1 uM
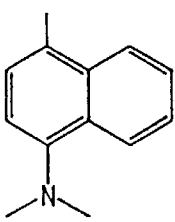
59-0090
MAX: 41%
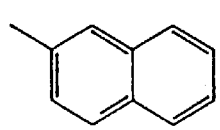
59-0092
MAX: 50%
EC50: 10 uM
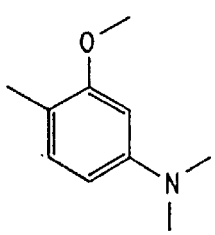
59-0150
MAX: 500%
EC50: 1 nM
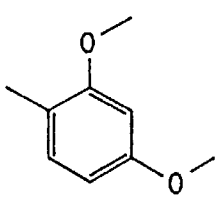
59-0199
MAX: 170%
EC50: 100 nM
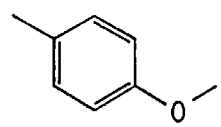
59-0198
MAX: 135%
EC50: 100 nM
FIG. 6C

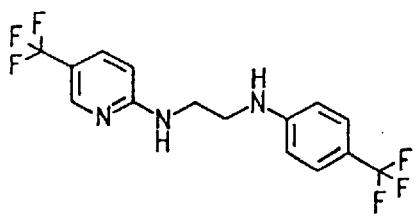
59-0145
MAX: 300%
EC50: 0.5 μM
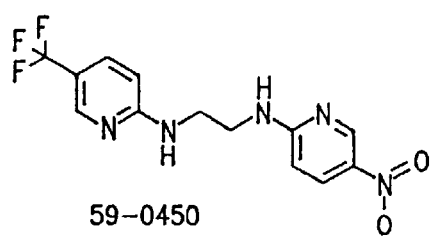
59-0450
MAX: 270%
EC50: 5 μM
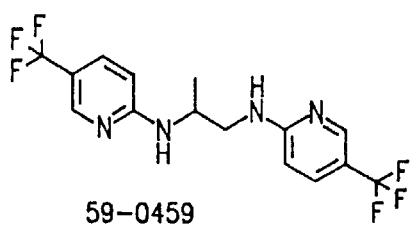
59-0459
MAX: 180%
EC50: 5 μM
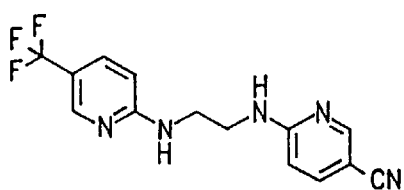
59-0483
MAX: 260%
EC50: 3 μM
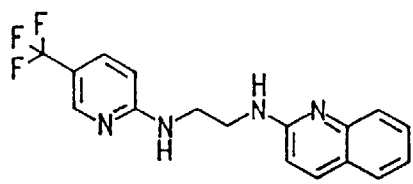
59-0480
MAX: 180%
EC50: 5 μM
FIG. 7

59-0045
EC50=5 nM

| COMPOUND | COMPOUND CLASS | LC50 | MAX RESPONSE OF 59-0008 | ZGI SCORE IN Ex Vivo ASSAY | OS SCORE IN Ex Vivo ASSAY |
|---|---|---|---|---|---|
| 59-0364 | P | 0 | 0 | 1 | |
| 59-0076 | P | 0 | 0 | 1 | |
| 59-0451 | P | 0 | 0 | 1 | |
| 59-0472 | P | 0 | 0 | 1 | |
| 59-0073 | P | 0 | 0 | | 1+ |
| 59-0095 | H | ?? | 0.5x (30 uM) | | 1 |
| 59-0471 | P | ?? | 0.5x (100 uM) | 1 | |
| 59-0030 | Q | ?? | .7x (1uM) | 1 | 1,1+ |
| 59-0470 | P | 50 uM | 1.2x (100 uM) | 1 | |
| 59-0450 | P | 5 uM | 2.7x (30 uM) | | |
| 59-0459 | P | 5 uM | 2x (10 uM) | 1 | |
| 59-0064 | Q | 3 uM | 1.5x (? uM) | 1 | |

| | | | | | |
|---|---|---|---|---|---|
| 59-0008 | Q | 1 uM | | | 1 |
| 59-0145 | P | 300nm | 4x9 | 1+,2- | 1+,2- |
| 59-0106 | T | 300 nM | 2x (9 uM) | | 1 |
| 59-0070 | T | 200 nM | 2x (3 uM) | | 1,1+ |
| 59-0097 | H | 100 nM? | 2x (30 uM) | | 1+ |
| 59-0096 | H | 100 nM? | 4x (100 uM) | | 1 |
| 59-0116 | H | 30 nM | 2.5x (3 uM) | | 1+,2- |
| 59-0210 | T | 30 nM | 2x (3 uM) | | 1 |
| 59-0098 | H | 20 nM | 2x (9uM) | 1+,2+ | 1+,2+ |
| 59-0019 | Q | 10 nM | 2.5x (300 nM) | 1+,2- | 1,1+ |
| 59-0078 | Q | 9 nM | 4x (1 uM) | | 1 |
| 59-0045 | H | 5 nM | 4x (1 uM) | 1 | 1 |
| 50-0197 | Q | 3 nM | 2.5x (300 nM) | 1 | 1+,2- |
| 59-0099 | T | 2 nM? | 3x (1 uM) | | 1,1+ |
| 59-0282 | Q | 1 nM | 2x (3 uM) | | 1+,2- |
| 59-0203 | + | + | 2x (3uM) | 1+,2 | 2,3 |
| 59-0072 | T | 300 pM | 2x (uM) | 1-1+ | 1,1+ |
| 59-0150 | Q | <1 nM | 5x (3 uM) | 1-2? | 1 |
| 59-0104 | T | <1 nM | 2x (uM) | 1+,2- | 1 |
| 59-0103 | T | <1 nM | 2x (30 nM) | | 1,1+ |
| 59-0124 | T | <1 nM | 2.5x (1 uM) | | 1+,2- |
| 59-0205 | T | <1 nM | 2x (2 uM) | | 1 |

H=HYDRAZONE/HYDRAZIDE (45)  T=BENZOTHIAZOLE (104)
Q=QUINOLINE/QUINOXALINE (197)
P=BIS-PYRIDINES (145)

FIG. 9

| MOLSTRUCTURE | MOL>NNC | MOL_WEIGHT_NUM1 |
|---|---|---|
| 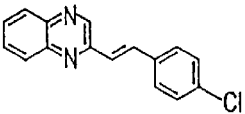 | 59-0020 | 266.732 |
| 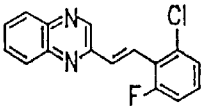 | 59-0021 | 284.723 |
| 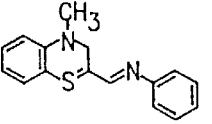 | 59-0022 | 266.367 |
| 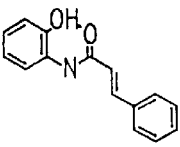 | 59-0023 | 239.276 |
| 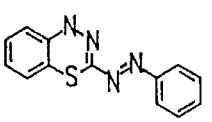 | 59-0008 | 254.315 |
| 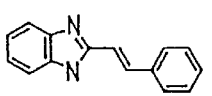 | 59-0024 | 220.276 |
| 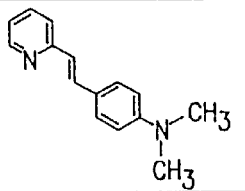 | 59-0025 | 224.308 |
| 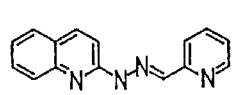 | 59-0026 | 248.29 |
| 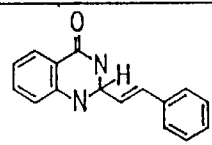 | 59-0027 | 250.303 |
| 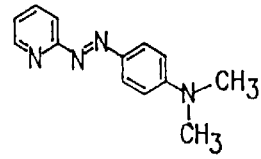 | 59-0028 | 226.283 |
| 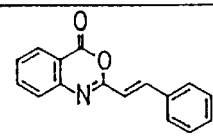 | 59-0029 | 249.272 |
FIG. 13A

| Structure | ID | Value | |
|---|---|---|---|
| 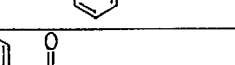 | 59-0031 | 231.3 | |
| 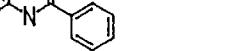 | 59-0030 | 233.275 | |
| 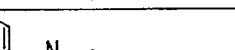 | 59-0032 | 248.287 | |
| 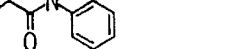 | 59-0033 | 248.287 | |
| 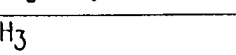 | 59-0034 | 268.343 | |
| 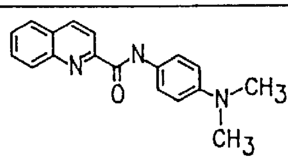 | 59-0035 | 291.356 | |
| 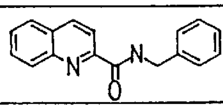 | 59-0036 | 262.314 | |
| 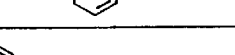 | 59-0037 | 308 | |
| 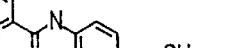 | 59-0038 | 241.295 | |
| 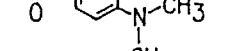 | 59-0039 | 312.352 | |
| 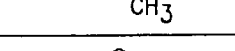 | 59-0040 | 290.368 | |
| 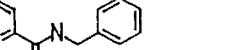 | 59-0041 | 501.902 | |
FIG. 13B

| Structure | ID | MW | |
|---|---|---|---|
| 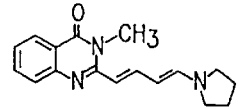 | 59-0042 | 281.36 | |
| 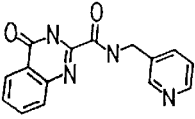 | 59-0043 | 280.288 | |
| 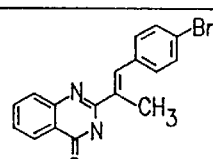 | 59-0044 | 341.21 | |
| 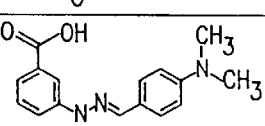 | 59-0045 | 283.333 | |
| 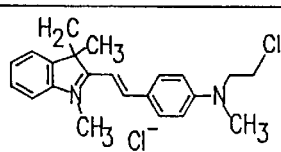 | 59-0046 | 389.372 | |
| 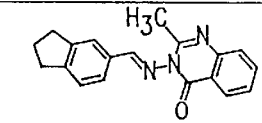 | 59-0047 | 303.367 | |
| 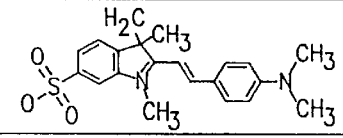 | 59-0048 | 384.501 | |
| 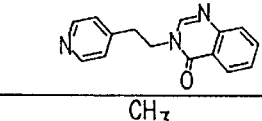 | 59-0049 | 251.29 | |
| 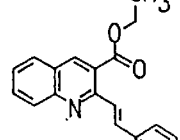 | 59-0050 | 303.364 | |
| 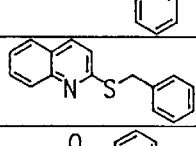 | 59-0051 | 251.353 | |
| 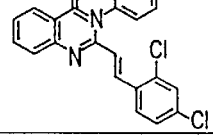 | 59-0052 | 393.276 | |
| 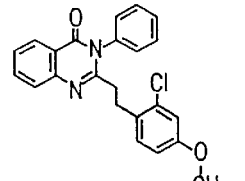 | 59-0053 | 354.412 | |
FIG. 13C

| Structure | ID | MW | |
|---|---|---|---|
| 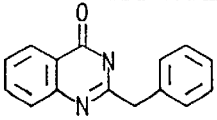 | 59-0054 | 236.276 | |
| 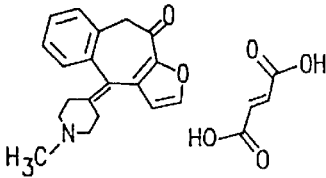 | 59-0055 | 425.508 | |
| 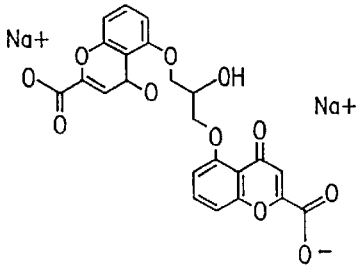 | 59-0056 | 512.341 | |
| 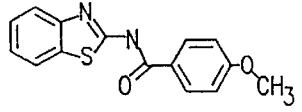 | 59-0102 | 284.339 | |
| 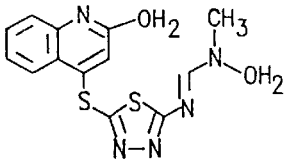 | 59-0057 | 329.448 | |
| 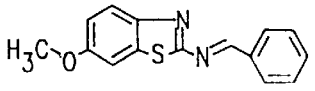 | 59-0058 | 268.34 | |
| 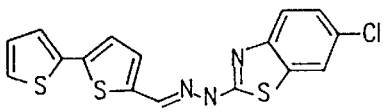 | 59-0059 | 375.923 | |
FIG. 13D-1

| Structure | ID | MW | |
|---|---|---|---|
| 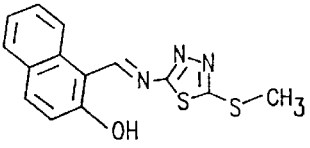 | 59-0060 | 301.391 | |
| 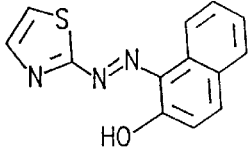 | 59-0061 | 255.3 | |
| 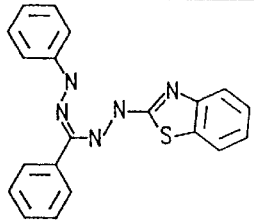 | 59-0062 | 357.44 | |
| 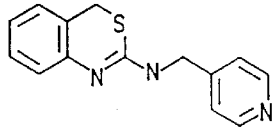 | 59-0063 | 255.344 | |
| 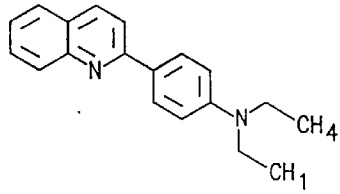 | 59-0064 | 276.385 | |
FIG. 13D-2

| Structure | ID | Value | |
|---|---|---|---|
| 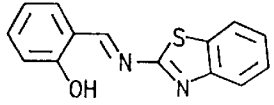 | 59-0065 | 254.313 | |
| 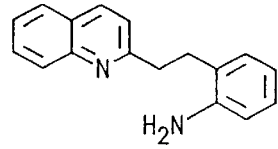 | 59-0066 | 248.33 | |
| 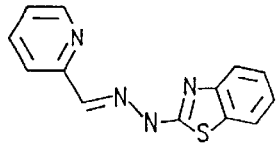 | 59.0067 | 254.315 | |
| 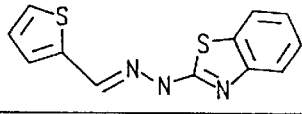 | 59-0068 | 259.354 | |
| 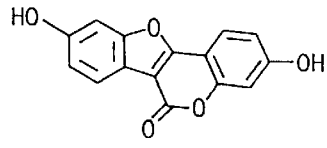 | 59-0069 | 268.223 | |
| 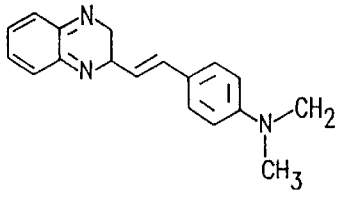 | 59-0019 | 275.353 | |
| 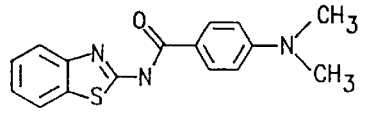 | 59-0070 | 297.38 | |
| 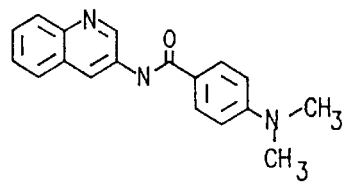 | 59-0071 | 291.352 | |
FIG. 13E-1

| | | |
|---|---|---|
| 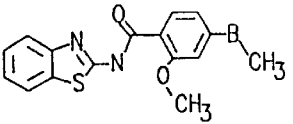 | 59-0072 | 330.431 |
| 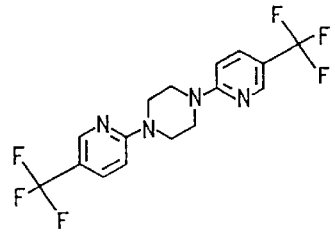 | 59-0073 | 376.303 |
| 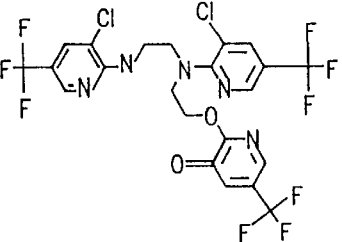 | 59-0074 | 642.735 |
| 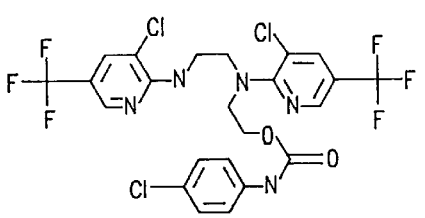 | 59-0075 | 616.775 |
FIG. 13E-2

| Structure | ID | Value | |
|---|---|---|---|
| 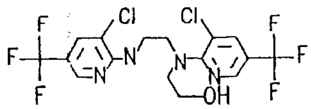 | 59-0076 | 463.208 | |
| 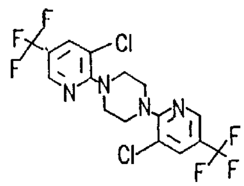 | 59-0077 | 445.193 | |
| 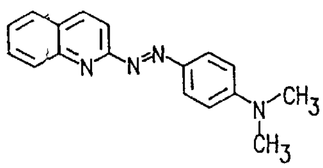 | 59-0078 | 276.341 | |
| 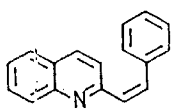 | 59-0079 | 231.297 | |
| 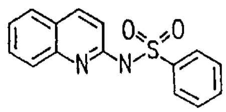 | 59-0080 | 284.338 | |
| 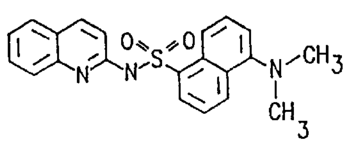 | 59-0081 | 377.466 | |
| 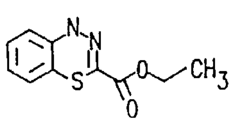 | 59-0082 | 222.267 | |
| 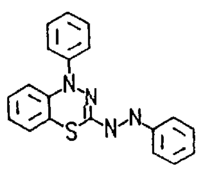 | 59-0083 | 330.414 | |

FIG. 13F-1

| | | |
|---|---|---|
| 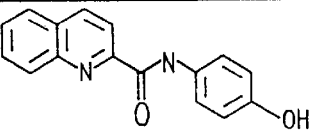 | 59-0084 | 264.283 |
| 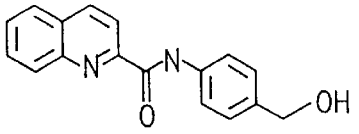 | 59-0085 | 278.31 |
| 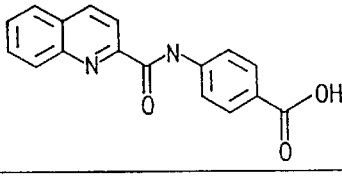 | 59-0086 | 292.293 |
| 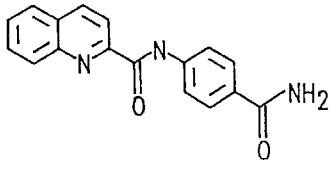 | 59-0087 | 291.309 |
FIG. 13F-2

| Structure | ID | Mass | |
|---|---|---|---|
| 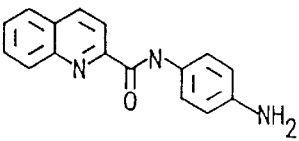 | 59-0088 | 263.299 | |
| 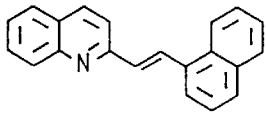 | 59-0089 | 281.357 | |
| 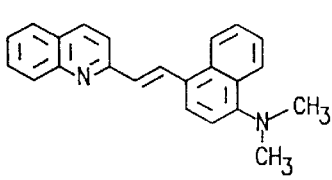 | 29-0090 | 324.425 | |
| 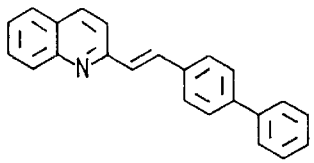 | 59-0091 | 307.394 | |
| 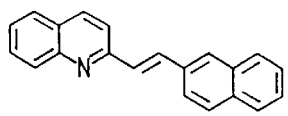 | 59-0092 | 281.357 | |
| 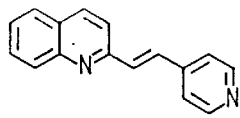 | 59-0093 | 232.285 | |
| 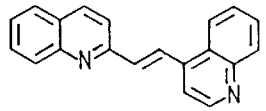 | 59-0094 | 282.345 | |
FIG. 13G-1

| Structure | ID | MW | |
|---|---|---|---|
| [structure] | 59-0095 | 299.328 | |
| [structure] | 59-0096 | 313.355 | |
| [structure] | 59-0097 | 330.41 | |
| [structure] | 59-0098 | 325.366 | |
| [structure] | 59-0099 | 280.393 | |

FIG. 13G-2

| Structure | ID | MW | |
|---|---|---|---|
| 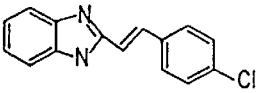 | 59-0100 | 254.719 | |
| 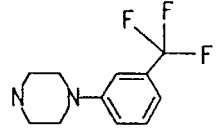 | 59-0101 | 230.232 | |
| 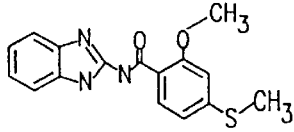 | 59-0103 | 313.379 | |
| 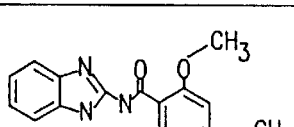 | 59-0104 | 297.312 | |
| 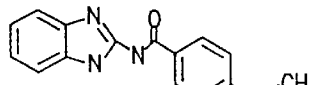 | 59-0105 | 267.287 | |
| 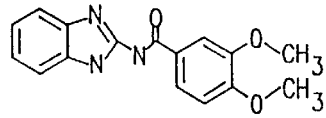 | 59-0106 | 297.312 | |
| 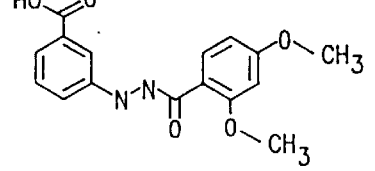 | 59-0107 | 332.378 | |
| 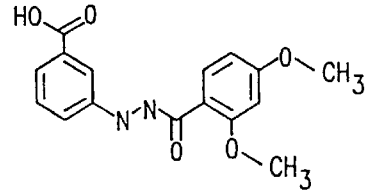 | 59-0108 | 316.311 | |
FIG. 13H-1

| Structure | ID | MW | |
|---|---|---|---|
| 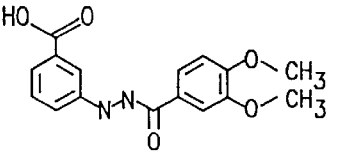 | 59-0109 | 316.311 | |
| 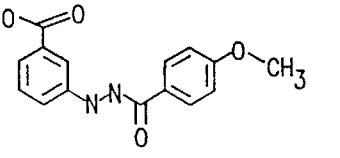 | 59-0110 | 286.286 | |
| 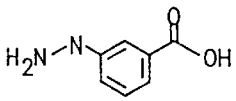 | 59-0111 | 152.152 | |
| 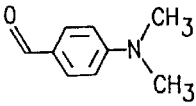 | 59-0112 | 149.192 | |
FIG. 13H-2

| | | | |
|---|---|---|---|
| 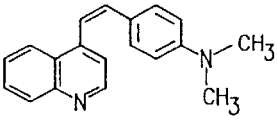 | 59-0113 | 274.365 | |
| 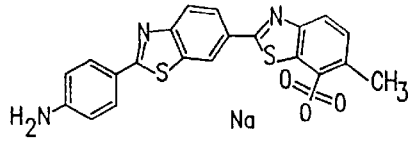 | 59-0114 | 475.548 | |
| 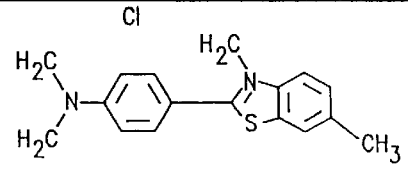 | 29-0115 | 318.87 | |
| 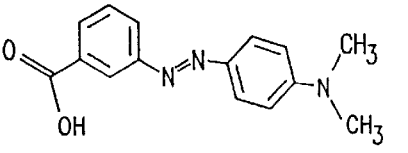 | 59-0116 | 269.302 | |
| 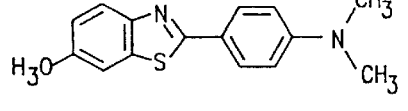 | 59-0117 | 268.382 | |
| 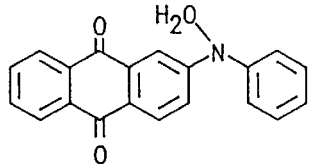 | 59-0118 | 313.354 | |
| 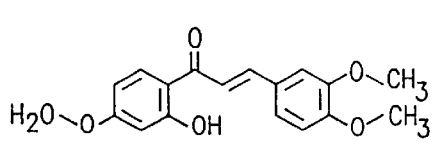 | 59-0119 | 314.335 | |
FIG. 13 I-1

| Structure | ID | MW | |
|---|---|---|---|
| 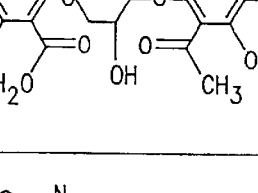 | 59-0120 | 504.485 | |
| 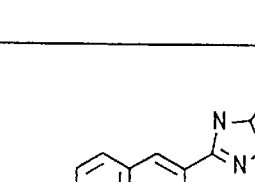 | 59-0121 | 245.284 | |
| 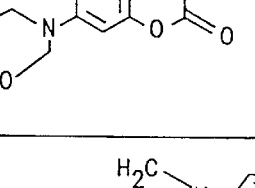 | 59-0122 | 333.389 | |
| 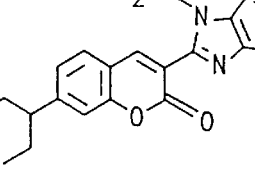 | 59-0123 | 347.416 | |
| 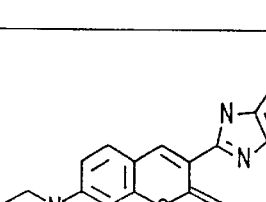 | 59-0124 | 350.44 | |
FIG. 13 I-2

| | | |
|---|---|---|
| 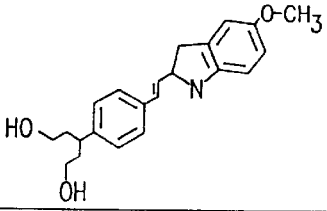 | 59-0125 | 372.447 |
| 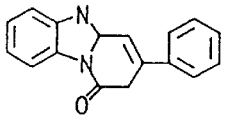 | 59-0126 | 260.295 |
| 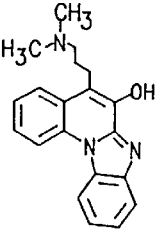 | 59-0127 | 329.405 |
| 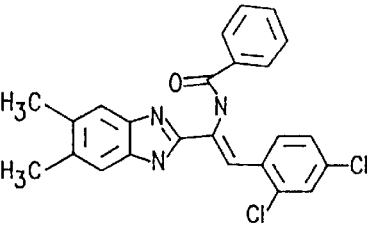 | 59-0128 | 436.34 |
| 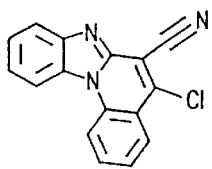 | 59-0129 | 277.713 |
| 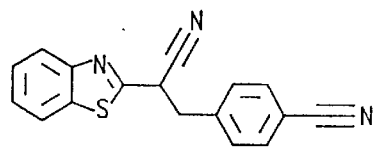 | 59-0130 | 287.345 |
| 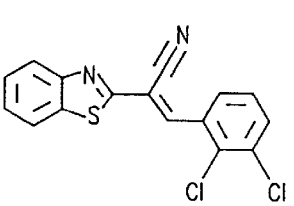 | 59-0131 | 331.225 |
FIG. 13J-1

| Structure | ID | Value | |
|---|---|---|---|
| 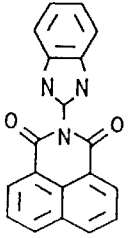 | 59-0132 | 313.315 | |
| 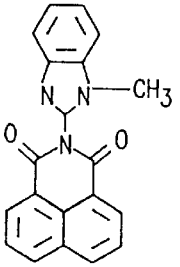 | 59-0133 | 327.342 | |
| 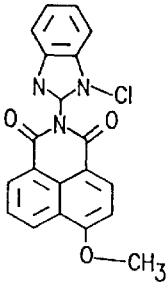 | 59-0134 | 357.367 | |
| 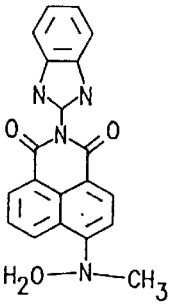 | 59-0135 | 356.383 | |
| 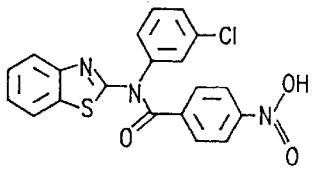 | 59-0136 | 411.868 | |
FIG. 13J-2

| Structure | ID | Value | |
|---|---|---|---|
| 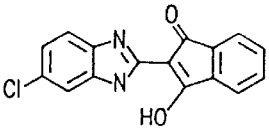 | 59-0137 | 296.712 | |
| 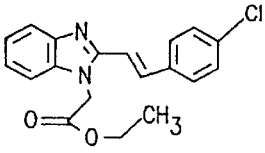 | 59-0138 | 340.808 | |
| 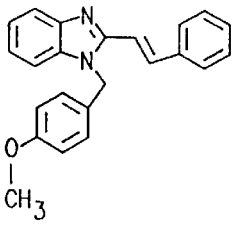 | 59-0139 | 340.424 | |
| 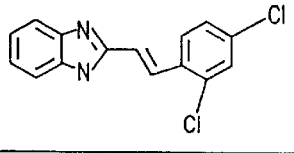 | 59-0140 | 289.164 | |
| 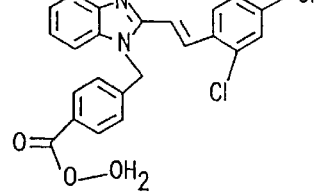 | 59-0141 | 437.324 | |
| 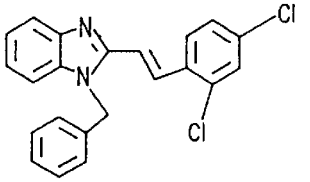 | 59-0142 | 379.288 | |
| 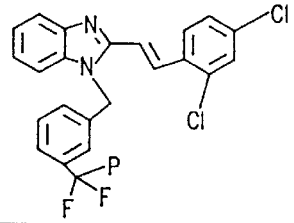 | 59-0143 | 447.285 | |
FIG. 13K-1

| Structure | ID | MW | |
|---|---|---|---|
| 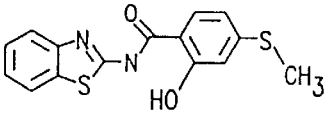 | 59-0144 | 316.404 | |
| 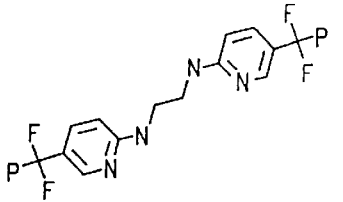 | 59-0145 | 350.265 | |
| 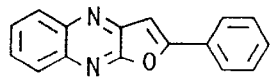 | 59-0146 | 246.268 | |
| 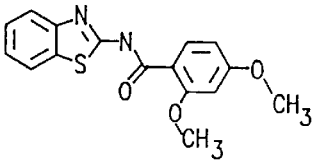 | 59-0147 | 314.364 | |
| 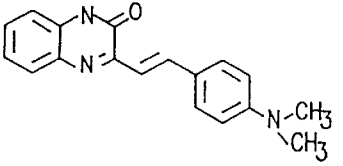 | 59-0148 | 291.352 | |
FIG. 13K-2

| Structure | ID | MW | |
|---|---|---|---|
| (benzothiazole-NHC(O)-phenyl(OCH3)(NO2)) | 59-0149 | 329.335 | |
| (quinoline-CH=CH-phenyl(OCH3)(N(CH3)2)) | 59-0150 | 304.391 | |
| (quinoline-C(O)NH-phenyl-OCH3) | 59-0151 | 278.31 | |
| (quinoline-C(O)NH-phenyl-F) | 59-0152 | 266.274 | |
| (quinoline-C(O)NH-phenyl-Cl) | 59-0153 | 282.729 | |
| (quinoline-C(O)NH-phenyl-CH3) | 59-0154 | 262.311 | |
| (quinoline-C(O)NH-phenyl-CF3) | 59-0155 | 316.281 | |

FIG. 13L-1

| Structure | ID | MW | |
|---|---|---|---|
| 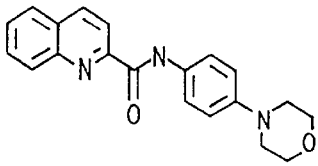 | 59-0156 | 333.389 | |
| 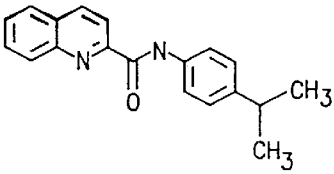 | 59-0157 | 290.364 | |
| 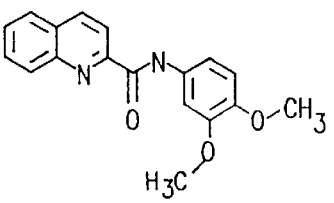 | 59-0158 | 308.335 | |
| 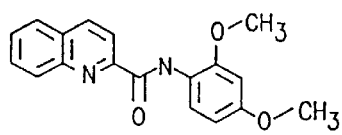 | 59-0159 | 308.335 | |
| 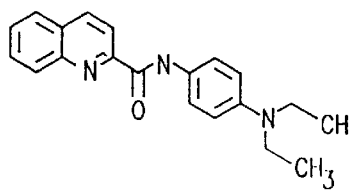 | 59-0160 | 319.406 | |
FIG. 13L-2

| | | |
|---|---|---|
| 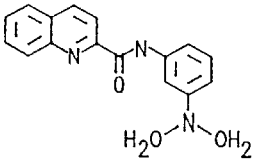 | 59-0161 | 291.352 |
| 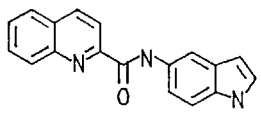 | 59-0162 | 287.321 |
| 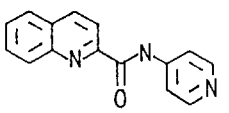 | 59-0163 | 249.272 |
| 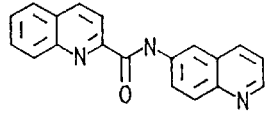 | 59-0164 | 299.332 |
| 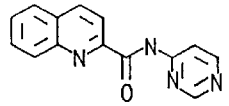 | 59-0165 | 250.26 |
| 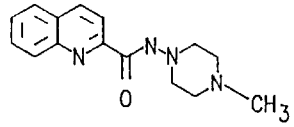 | 59-0166 | 270.334 |
| 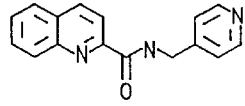 | 59-0167 | 263.299 |
FIG. 13M-1

| | | | |
|---|---|---|---|
| 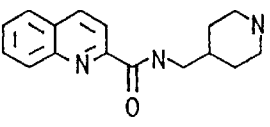 | 59-0168 | 269.346 | |
| 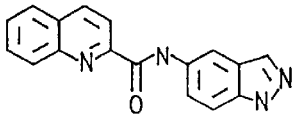 | 59-0169 | 288.309 | |
| 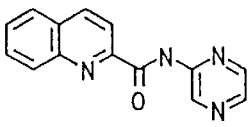 | 59-0170 | 250.26 | |
| 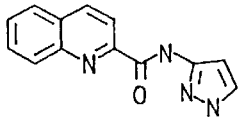 | 59-0171 | 238.249 | |
| 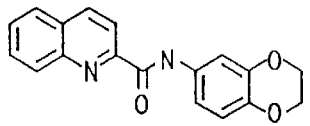 | 59-0172 | 306.32 | |
FIG. 13M-2

| | | | |
|---|---|---|---|
| 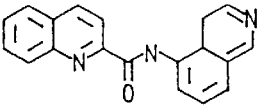 | 59-0173 | 299.332 | |
| 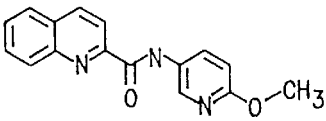 | 59-0174 | 279.298 | |
| 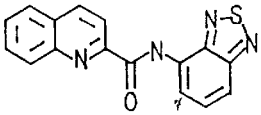 | 59-0175 | 306.348 | |
| 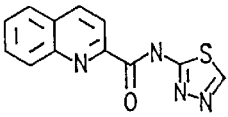 | 59-0176 | 256.288 | |
| 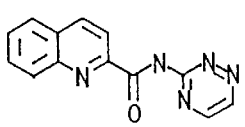 | 59-0177 | 251.248 | |
| 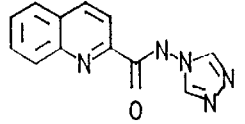 | 59-0178 | 239.237 | |
| 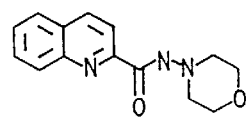 | 59-0179 | 257.292 | |
FIG. 13N-1

| Structure | ID | MW | |
|---|---|---|---|
| 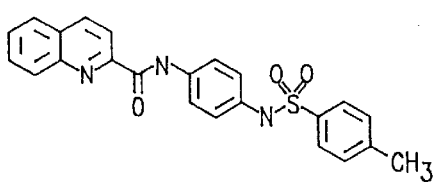 | 59-0180 | 417.487 | |
| 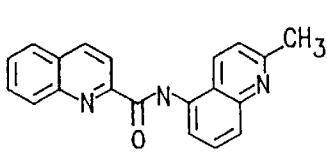 | 59-0181 | 313.358 | |
| 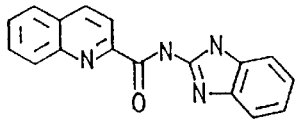 | 59-0182 | 288.309 | |
| 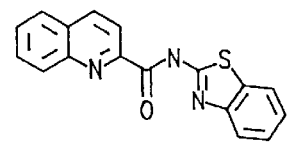 | 59-0183 | 305.36 | |
| 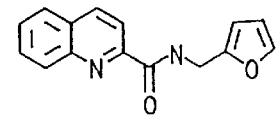 | 59-0184 | 252.272 | |
FIG. 13N-2

| Structure | No. | MW | |
|---|---|---|---|
| 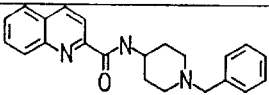 | 59-0185 | 345.444 | |
| 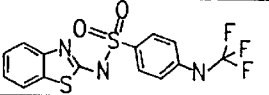 | 59-0186 | 374.362 | |
| 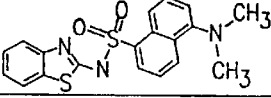 | 59-0187 | 383.494 | |
| 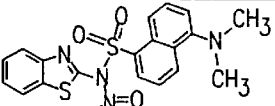 | 59-0188 | 616.784 | |
| 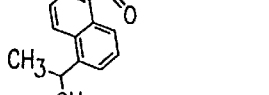 | 59-0189 | 490.579 | |
| 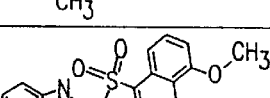 | 59-0190 | 550.631 | |
| 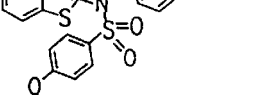 | 59-0191 | 584.605 | |
| 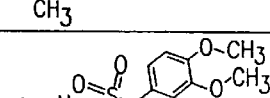 | 59-0192 | 344.389 | |
| 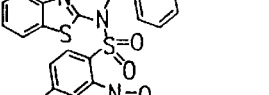 | 59-0193 | 344.389 | |
| 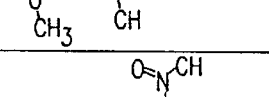 | 59-0194 | 344.389 | |
FIG. 130-1

| | | | |
|---|---|---|---|
|  | 59-0195 | 318.783 | |
|  | 59-0196 | 323.202 | |

| | | |
|---|---|---|
|  | 59-0197 | 323.202 |
| 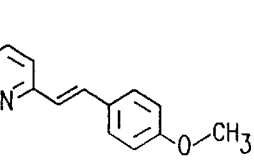 | 59-0198 | 261.323 |
| 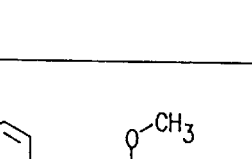 | 59-0199 | 291.348 |
| 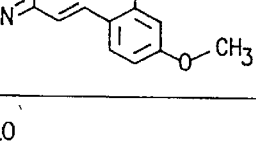 | 59-0200 | 342.349 |
| 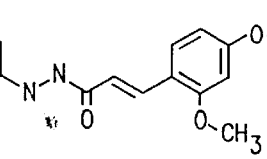 | 59-0201 | 331.326 |
| 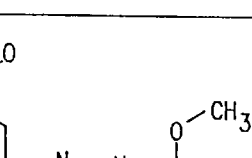 | 59-0202 | 300.337 |
| 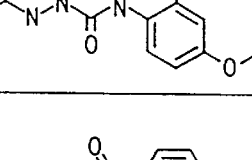 | 59-0203 | 292.336 |
FIG. 13P-1

| | | |
|---|---|---|
| 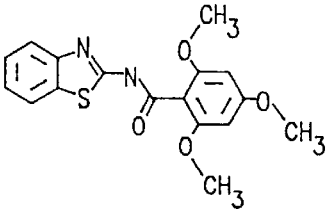 | 59-0204 | 344.389 |
| 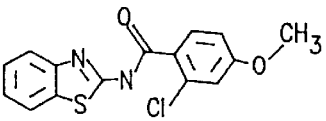 | 59-0205 | 318.783 |
| 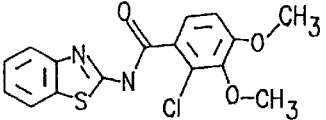 | 59-0206 | 348.809 |
| 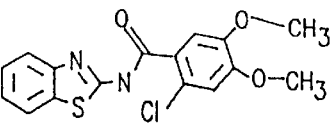 | 59-0207 | 348.809 |
| 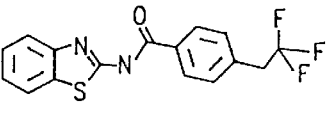 | 59-0208 | 336.308 |
FIG. 13P-2

| Structure | ID | MW | |
|---|---|---|---|
| 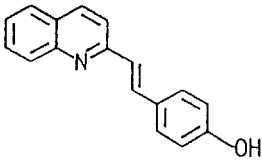 | 59-0209 | 247.296 | |
| 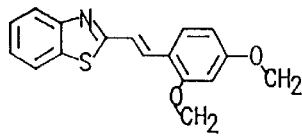 | 59-0210 | 297.376 | |
| 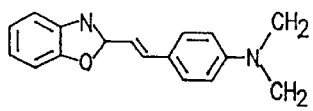 | 29-0211 | 264.326 | |
| 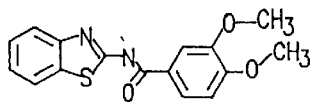 | 59-0212 | 314.364 | |
| 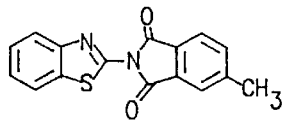 | 59-0213 | 294.333 | |
| 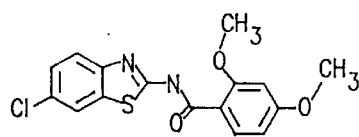 | 59-0214 | 348.809 | |
| 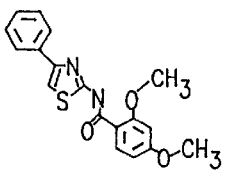 | 59-0215 | 340.401 | |
FIG. 13Q-1

| Structure | ID | MW | |
|---|---|---|---|
| 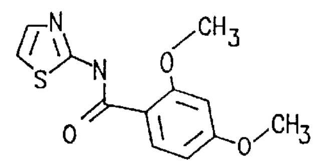 | 59-0216 | 264.304 | |
| 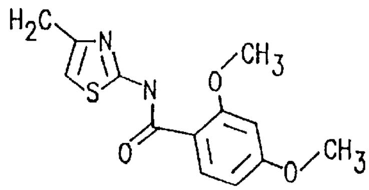 | 59-0217 | 278.331 | |
| 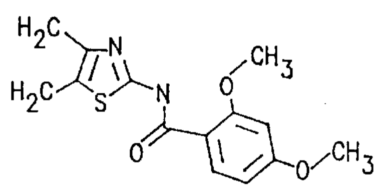 | 59-0218 | 292.357 | |
| 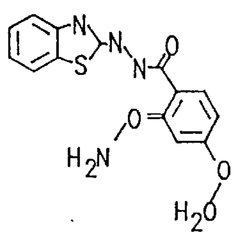 | 59-0219 | 329.379 | |
| 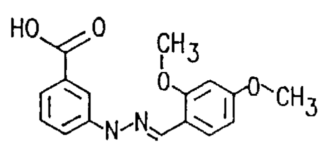 | 59-0220 | 300.312 | |

FIG. 13Q-2

| Structure | No. | MW | |
|---|---|---|---|
| (4-carboxyphenyl)-N=N-CH=benzene-N(CH3)2 | 59-0221 | 283.329 | |
| (3-carboxyphenyl)-N=N-CH=CH-CH=benzene-N(CH3)2 | 59-0222 | 309.367 | |
| (3-carboxyphenyl)-N=N-CH=(4-carboxyphenyl) | 59-0223 | 284.27 | |
| (3-carboxyphenyl)-N=N-CH=(2,3,4-trimethoxyphenyl) | 59-0224 | 330.338 | |
| (3-carboxyphenyl)-N=N-CH=(3-hydroxyphenyl) | 59-0225 | 256.26 | |
| (3-carboxyphenyl)-N=N-CH=(4-nitrophenyl) | 59-0226 | 285.258 | |
| benzothiazol-2-yl-N=N-CH=benzene-N(CH3)(OCH3) | 59-0227 | 296.396 | |

FIG. 13R-1

| Structure | ID | MW | |
|---|---|---|---|
| 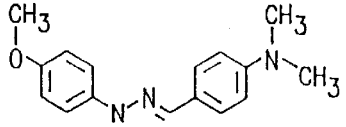 | 59-0228 | 269.346 | |
| 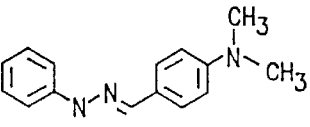 | 59-0229 | 239.32 | |
| 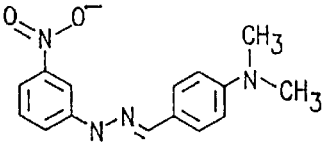 | 59-0230 | 284.317 | |
| 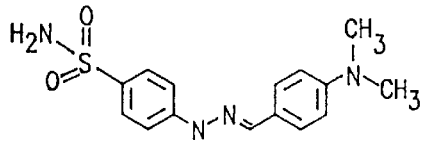 | 59-0231 | 318.399 | |
| 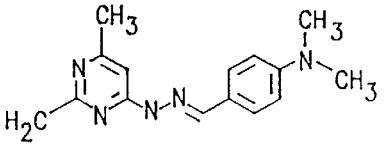 | 59-0232 | 269.35 | |
FIG. 13R-2

| | | | |
|---|---|---|---|
| 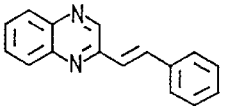 | 59-0233 | 232.285 | |
| 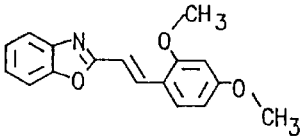 | 59-0234 | 281.31 | |
| 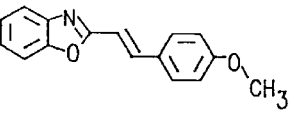 | 59-0235 | 251.284 | |
| 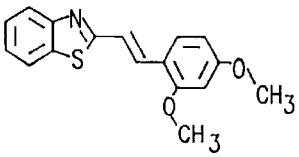 | 59-0236 | 280.325 | |
| 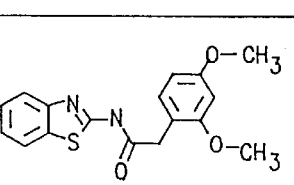 | 59-0237 | 328.39 | |
| 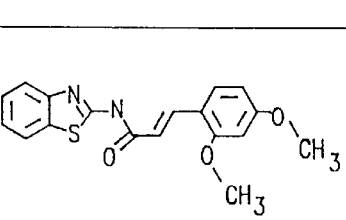 | 59-0238 | 340.401 | |
| 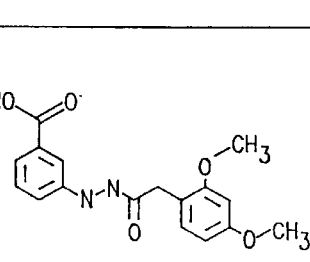 | 59-0239 | 330.338 | |
| 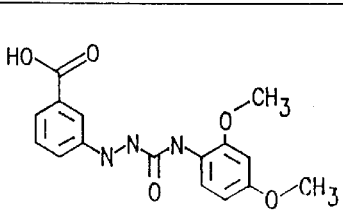 | 59-0240 | 347.393 | |
FIG. 13S-1

| | | | |
|---|---|---|---|
| 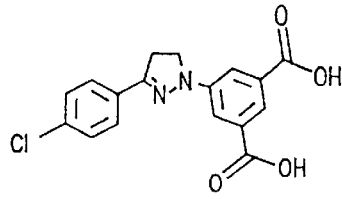 | 59-0241 | 344.753 | |
| 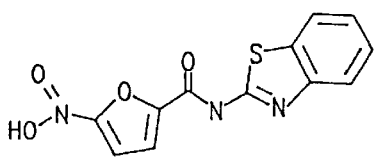 | 59-0242 | 291.286 | |
| 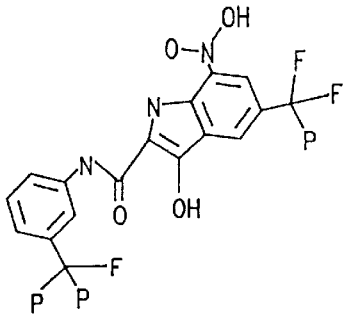 | 59-0243 | 455.334 | |
| 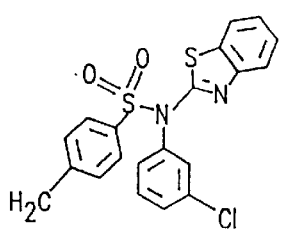 | 59-0244 | 414.935 | |
FIG. 13S-2

| Structure | ID | Value | |
|---|---|---|---|
| (structure) | 59-0245 | 419.887 | |
| (structure) | 59-0246 | 675.856 | |
| (structure) | 59-0247 | 333.385 | |
| (structure) | 59-0248 | 247.296 | |
| (structure) | 59-0249 | 298.297 | |
| (structure) | 59-0250 | 332.742 | |
| (structure) | 59-0251 | 386.426 | |
| (structure) | 59-0252 | 361.376 | |

FIG. 13T-1

| Structure | ID | MW | |
|---|---|---|---|
| Cl-benzothiazole-NH-C(O)-benzene(2,4-diOCH3) | 59-0253 | 348.809 | |
| H2C-benzothiazole-NH-C(O)-benzene(2,4-diOCH3) | 59-0254 | 328.39 | |
| H2C-S(O)-benzothiazole-NH-C(O)-benzene(2,4-diOCH3) | 59-0255 | 376.455 | |
| HO-N(=O)-benzothiazole-NH-C(O)-benzene(2,4-diOCH3) | 59-0256 | 361.376 | |

FIG. 13T-2

| Structure | No. | MW | |
|---|---|---|---|
| 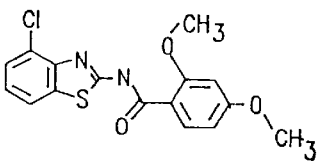 | 59-0257 | 348.809 | |
| 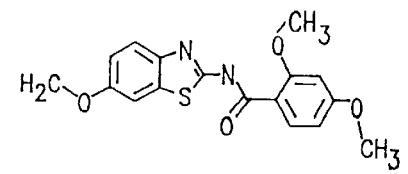 | 59-0258 | 344.389 | |
| 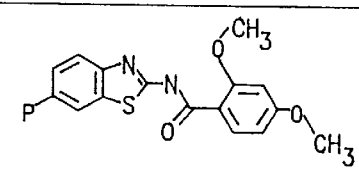 | 59-0259 | 332.354 | |
| 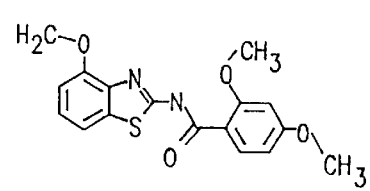 | 59-0260 | 344.389 | |
| 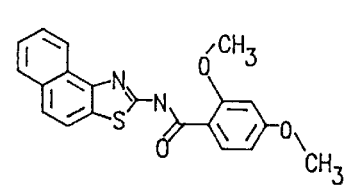 | 59-0261 | 364.423 | |
| 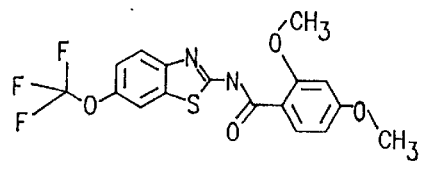 | 59-0262 | 398.36 | |
| 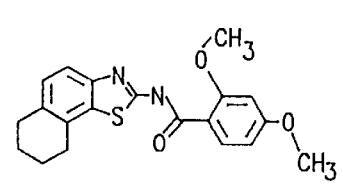 | 59-0263 | 368.455 | |
FIG. 13U-1

| | | | |
|---|---|---|---|
| 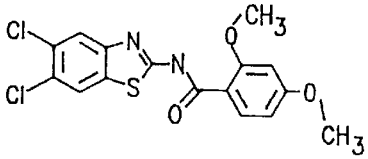 | 59-0264 | 383.254 | |
| 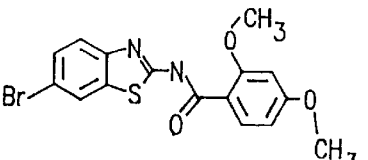 | 59-0265 | 393.26 | |
| 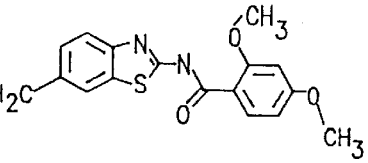 | 59-0266 | 328.39 | |
| 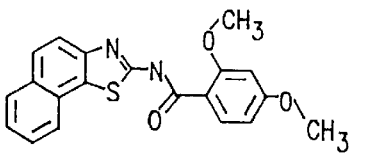 | 59-0267 | 364.423 | |
| 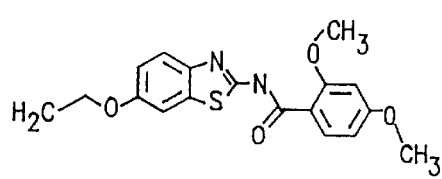 | 59-0268 | 358.416 | |
FIG. 13U-2

| Structure | ID | MW | |
|---|---|---|---|
| 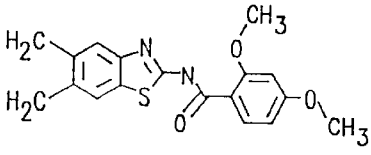 | 59-0269 | 342.417 | |
| 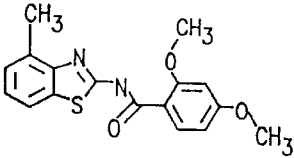 | 59-0270 | 328.39 | |
| 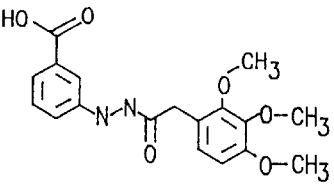 | 59-0271 | 360.364 | |
| 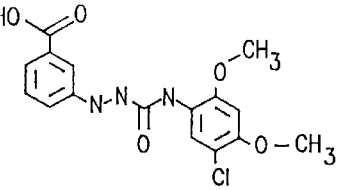 | 59-0272 | 381.838 | |
| 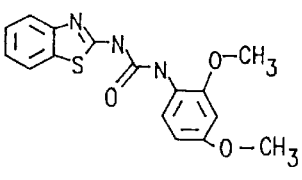 | 59-0273 | 345.445 | |
| 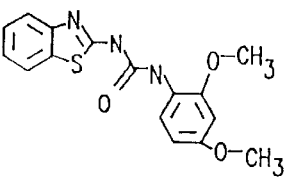 | 59-0274 | 329.379 | |
| 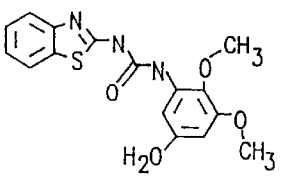 | 59-0275 | 328.39 | |
FIG. 13V-1

| | 59-0276 | 358.373 | |
|---|---|---|---|
| 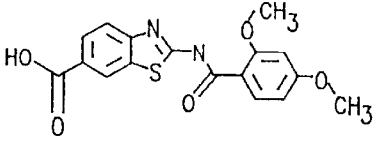 | | | |
| 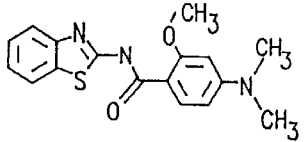 | 59-0279 | 327.406 | |
| 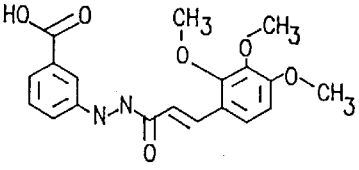 | 59-0277 | 372.375 | |
| 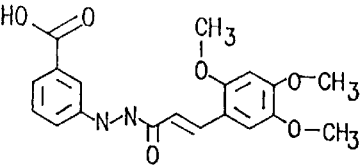 | 59-0278 | 372.375 | |
| 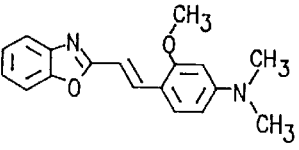 | 59-0280 | 394.352 | |
FIG. 13V-2

| Structure | ID | MW | |
|---|---|---|---|
| 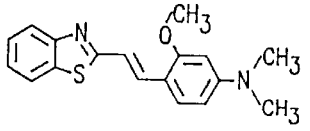 | 59-0281 | 310.419 | |
| 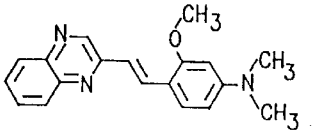 | 59-0282 | 305.379 | |
| 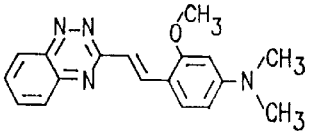 | 59-0283 | 306.367 | |
| 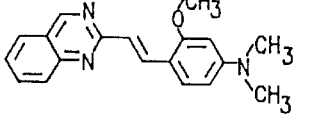 | 59-0284 | 305.379 | |
| 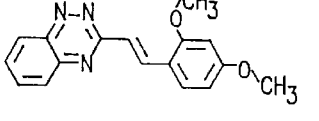 | 59-0285 | 393.324 | |
| 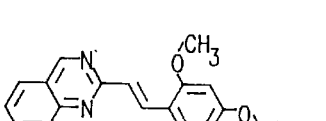 | 59-0286 | 292.336 | |
| 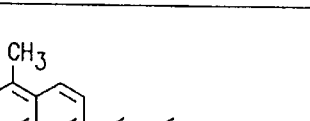 | 59-0287 | 306.32 | |
FIG. 13W-1

| Structure | ID | MW | |
|---|---|---|---|
| 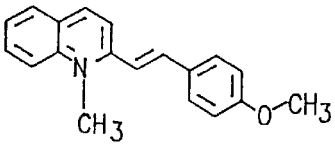 | 59-0288 | 276.357 | |
| 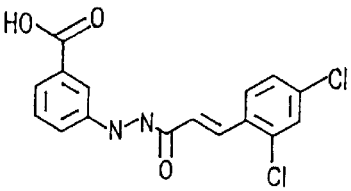 | 59-0289 | 351.188 | |
| 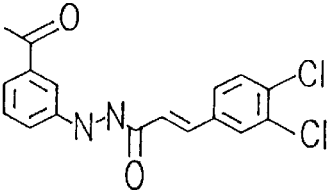 | 59-0290 | 351.188 | |
| 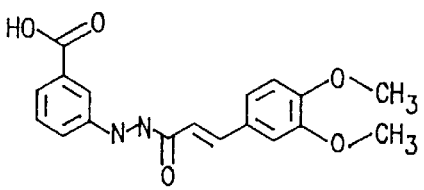 | 59-0291 | 342.349 | |
| 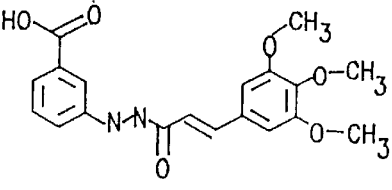 | 59-0292 | 372.375 | |
FIG. 13W-2

| Structure | ID | MW | |
|---|---|---|---|
| 3-[N'-(3,5-dimethoxycinnamoyl)hydrazino]benzoic acid | 59-0293 | 342.349 | |
| 3-[N'-(2,4-difluorocinnamoyl)hydrazino]benzoic acid | 59-0294 | 318.278 | |
| 3-[N'-(3-methoxycinnamoyl)hydrazino]benzoic acid | 59-0295 | 312.323 | |
| 3-[N'-(3-chlorocinnamoyl)hydrazino]benzoic acid | 59-0296 | 316.743 | |
| 3-[N'-(4-nitrocinnamoyl)hydrazino]benzoic acid | 59-0297 | 329.31 | |
| 3-[N'-(3-hydroxycinnamoyl)hydrazino]benzoic acid | 59-0298 | 298.297 | |
| chromone-tetrazole derivative | 59-0299 | 304.308 | |

FIG. 13X-1

| Structure | ID | Value | |
|---|---|---|---|
| 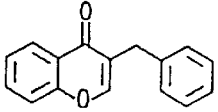 | 59-0300 | 236.269 | |
| 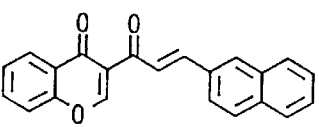 | 59-0301 | 326.35 | |
| 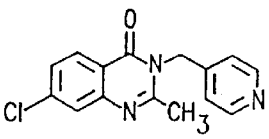 | 59-0302 | 285.733 | |
| 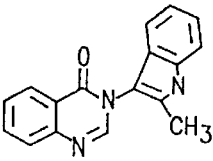 | 59-0303 | 275.31 | |
| 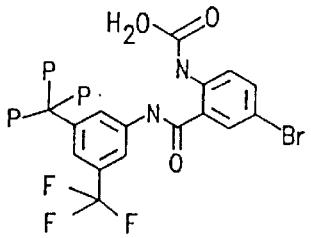 | 59-0304 | 469.178 | |
FIG. 13X-2

| Structure | ID | Value | |
|---|---|---|---|
| 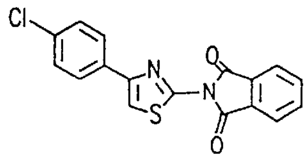 | 59-0305 | 340.789 | |
| 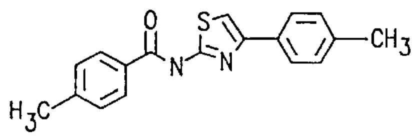 | 59-0306 | 308.403 | |
| 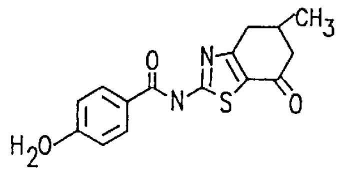 | 59-0307 | 300.38 | |
| 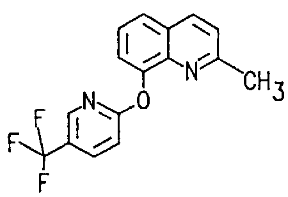 | 59-0308 | 304.27 | |
| 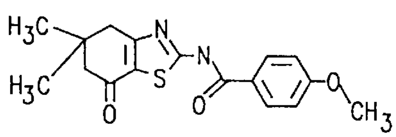 | 59-0309 | 330.406 | |
| 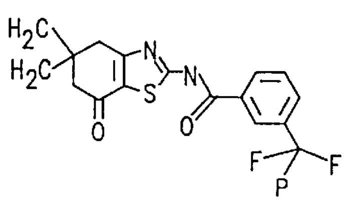 | 59-0310 | 368.378 | |
| 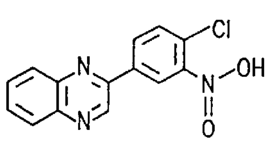 | 59-0311 | 287.705 | |

FIG. 13Y-1

| | | |
|---|---|---|
| 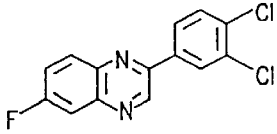 | 59-0313 | 293.127 |
| 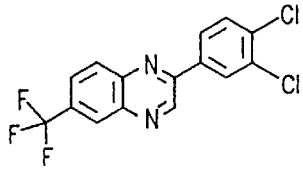 | 59-0314 | 343.134 |
| 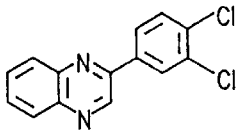 | 59-0315 | 275.137 |
| 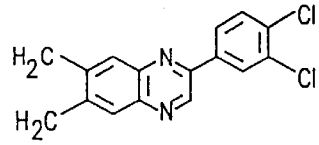 | 59-0316 | 303.191 |
|  | 59-0317 | 377.579 |
FIG. 13Y-2

| Structure | ID | Value | |
|---|---|---|---|
| 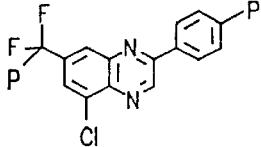 | 59-0318 | 326.679 | |
| 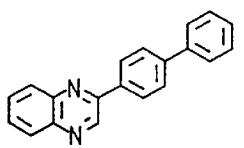 | 59-0319 | 282.345 | |
| 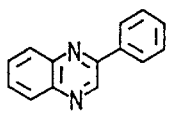 | 59-0320 | 206.247 | |
| 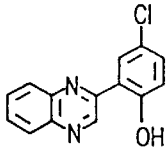 | 59-0321 | 256.691 | |
| 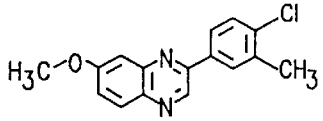 | 59-0322 | 284.745 | |
| 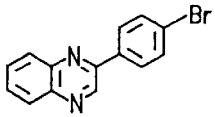 | 59-0323 | 285.143 | |
| 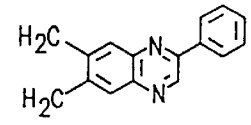 | 59-0324 | 234.301 | |
| 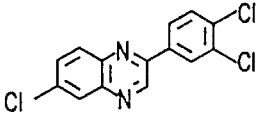 | 59-0312 | 309.582 | |
FIG. 13Z-1

| Structure | ID | MW | |
|---|---|---|---|
| 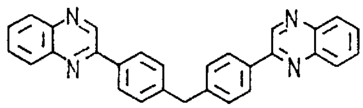 | 59-0325 | 424.505 | |
| 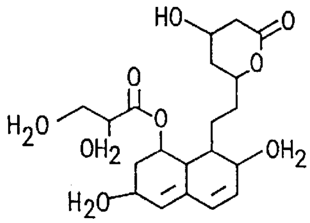 | 59-0326 | 404.543 | |
| 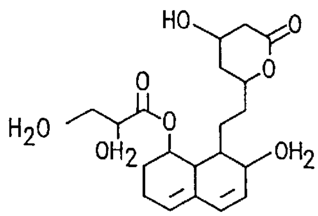 | 59-0327 | 390.517 | |
| 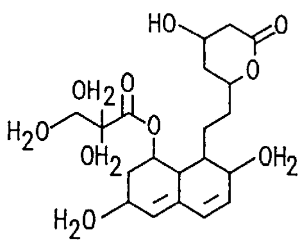 | 59-0328 | 418.57 | |

FIG. 13Z-2

| | 59-0329 | 424.53 | |
|---|---|---|---|
| | 59-0330 | 411.47 | |

FIG. 13AA

| | 59-0354 | 421.419 | |
|---|---|---|---|
| 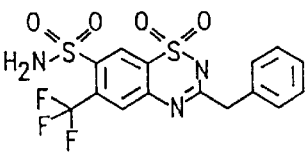 | | | |
| | 59-0342 | 425.497 | |
| 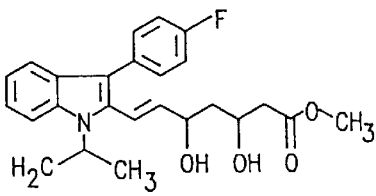 | | | |
FIG. 13BB

| Structure | Number | Value | |
|---|---|---|---|
| (benzoate-CH2-N-CH2-Ar(CF3)) | 59-0357 | 351.366 | |
| (F3C-Ar-NH-(CH2)3-NH-pyridyl-CF3) | 59-0361 | 364.292 | |
| (F3C-Ar-NH-C(O)-C(O)-NH-Ar-CF3) | 59-0362 | 376.255 | |
| (pyrimidine-NH-CH2CH2-NH-pyrimidine) | 59-0363 | 216.247 | |
| (F3C-pyridyl-N(CH3)-CH2CH2-N(CH3)-pyridyl-CF3) | 59-0364 | 378.318 | |
| (pyrazine-NH-CH2CH2-NH-pyrazine) | 59-0365 | 216.247 | |
| (F3C-pyridyl-S-CH2CH2-S-pyridyl-CF3) | 59-0366 | 384.367 | |
| (F3C-Ar-NH-CH2CH2-NH-Ar-CF3) | 59-0367 | 348.289 | |

FIG. 13CC

| Structure | ID | MW | | |
|---|---|---|---|---|
| 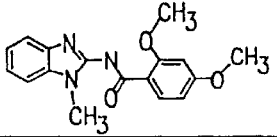 | 59-0368 | 311.339 | | |
| 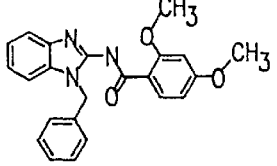 | 59-0369 | 387.437 | | |
| 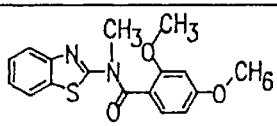 | 59-0370 | 328.39 | | |
| 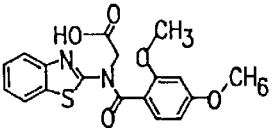 | 59-0371 | 372.399 | | |
| 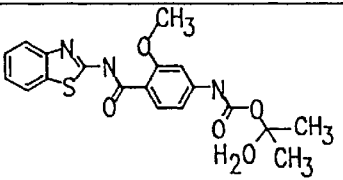 | 59-0372 | 399.469 | | |
| 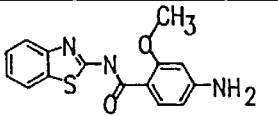 | 59-0373 | 299.353 | | |
| 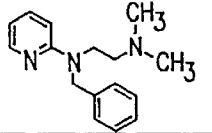 | 59-0374 | 255.363 | | |
| 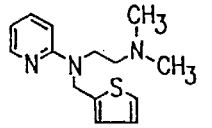 | 59-0375 | 261.391 | | |
| 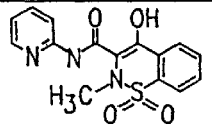 | 59-0376 | 331.351 | | |
| 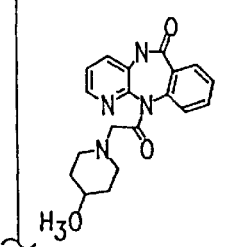 | 59-0377 | 351.408 | | |
FIG. 13DD-1

| | | 59-0378 | 285.389 | |
|---|---|---|---|---|
| | structure | 59-0379 | 337.379 | |

FIG. 13DD-2

| Structure | ID | MW | |
|---|---|---|---|
| 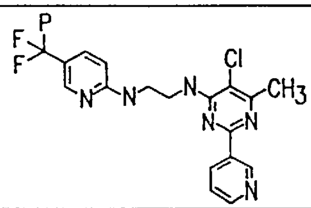 | 59-0380 | 408.813 | |
| 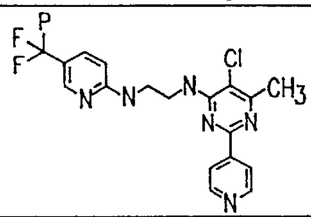 | 59-0381 | 408.813 | |
| 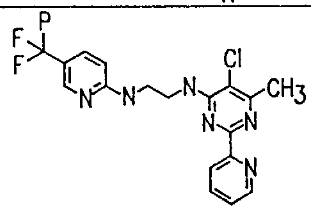 | 59-0382 | 408.813 | |
| 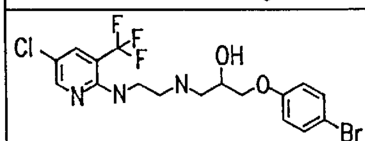 | 59-0383 | 468.699 | |
| 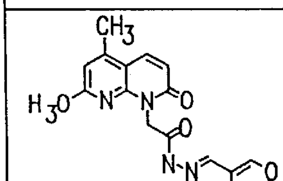 | 59-0384 | 340.405 | |
| 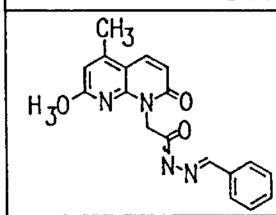 | 59-0385 | 334.377 | |
| 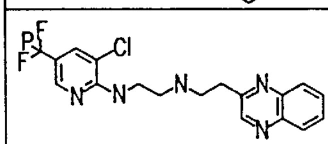 | 59-0386 | 367.761 | |
| 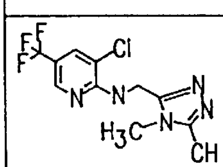 | 59-0387 | 323.729 | |
| 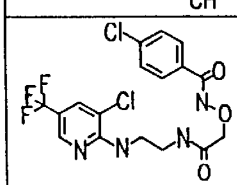 | 59-0388 | 451.23 | |

FIG. 13EE-1

| Structure | No. | Mass | |
|---|---|---|---|
| 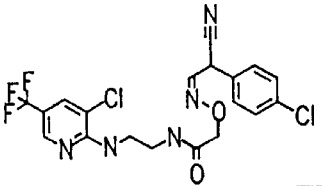 | 59-0389 | 474.268 | |
| 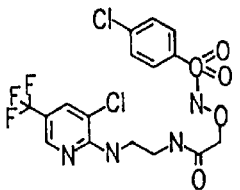 | 59-0390 | 487.284 | |
| 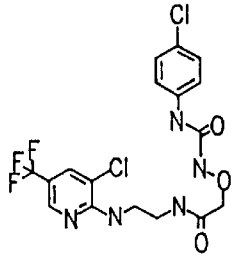 | 59-0391 | 466.245 | |
FIG. 13EE-2

| Structure | No. | Value | |
|---|---|---|---|
| 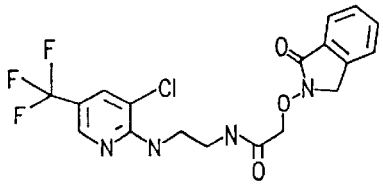 | 59-0392 | 442.78 | |
| 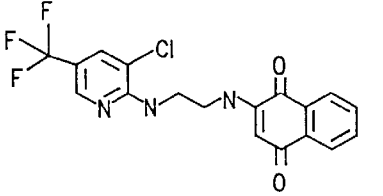 | 59-0393 | 395.767 | |
| 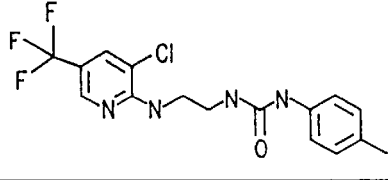 | 59.0394 | 393.195 | |
| 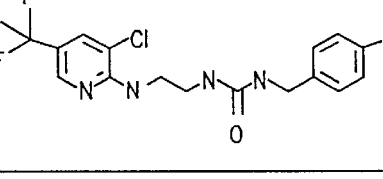 | 59-0395 | 370.804 | |
| 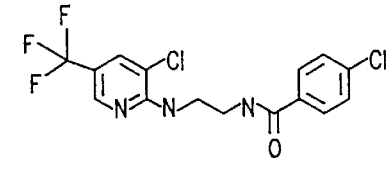 | 59-0396 | 378.18 | |
| 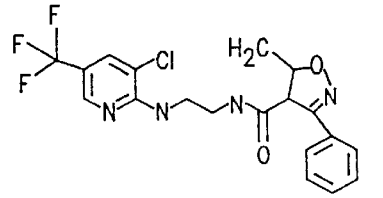 | 59-0397 | 424.808 | |
| 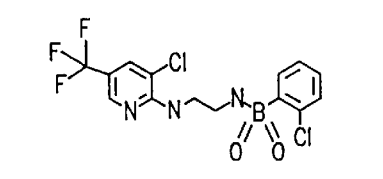 | 59-0398 | 414.234 | |
FIG. 13FF-1

| Structure | ID | Mass | |
|---|---|---|---|
| 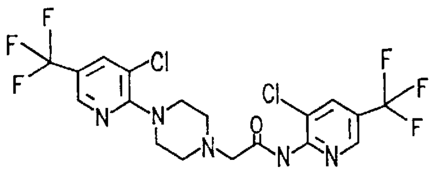 | 59-0399 | 502.245 | |
| 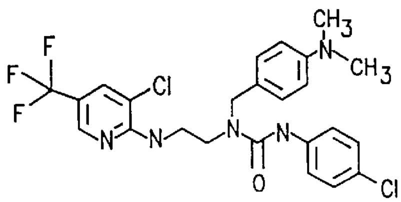 | 59-0400 | 526.388 | |
| 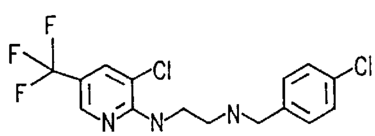 | 59-0401 | 364.197 | |
| 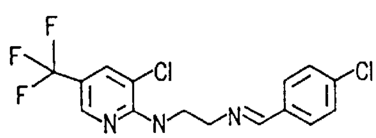 | 59-0402 | 362.181 | |
| 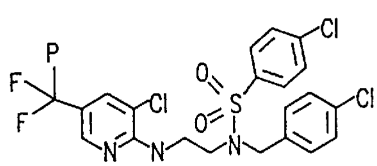 | 59-0403 | 538.803 | |

FIG. 13FF-2

| Structure | No. | MW | |
|---|---|---|---|
| 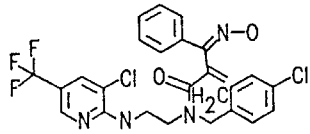 | 59-0404 | 549.378 | |
| 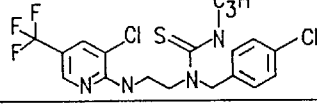 | 59-0405 | 437.315 | |
| 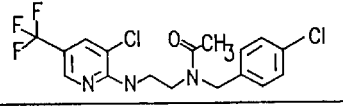 | 59-0406 | 406.233 | |
| 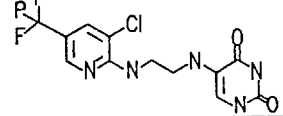 | 59-0407 | 349.699 | |
| 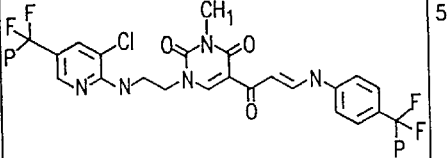 | 59-0408 | 561.868 | |
| 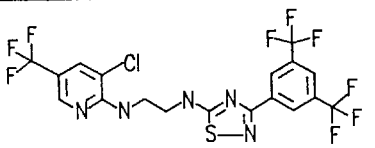 | 59-0409 | 535.821 | |
| 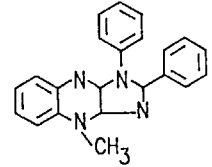 | 59-0410 | 340.428 | |
| 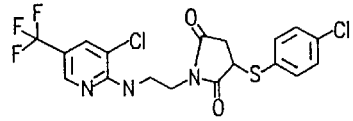 | 59-0411 | 464.294 | |
| 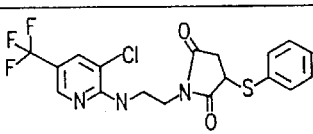 | 59-0412 | 429.849 | |
| 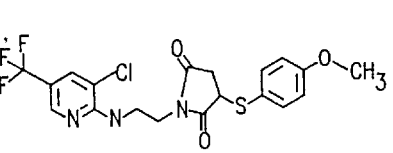 | 59-0413 | 459.874 | |
FIG. 13GG-1

| | 59-0414 | 497.846 | |
|---|---|---|---|
| 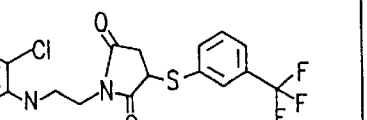 | | | |
| 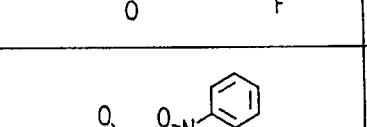 | 59-0415 | 516.905 | |
FIG. 13GG-2

| Structure | No. | MW | |
|---|---|---|---|
| 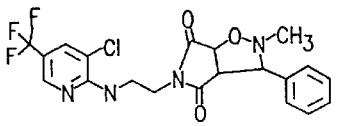 | 59-0416 | 454.834 | |
| 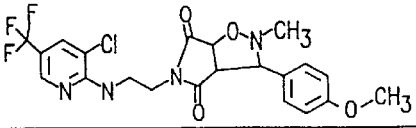 | 59-0417 | 484.86 | |
| 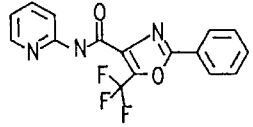 | 59-0418 | 333.268 | |
| 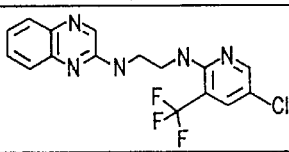 | 59-0419 | 367.761 | |
| 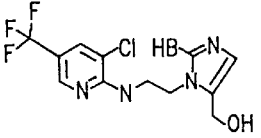 | 59-0420 | 352.767 | |
| 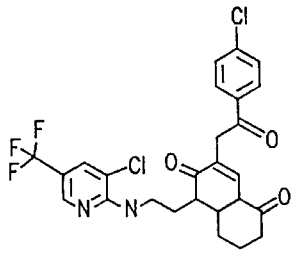 | 59-0421 | 539.339 | |
| 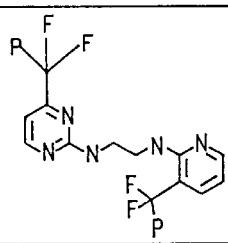 | 59-0422 | 351.253 | |
| 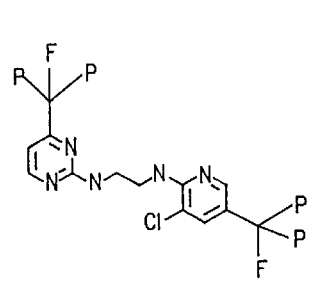 | 59-0423 | 385.698 | |
FIG. 13HH-1

| Structure | ID | Value | |
|---|---|---|---|
| (structure) | 59-0424 | 484.186 | |
| (structure) | 59-0425 | 400.186 | |
| (structure) | 59-0426 | 380.756 | |
| (structure) | 59-0427 | 414.213 | |

FIG. 13HH-2

| Structure | No. | MW | |
|---|---|---|---|
| 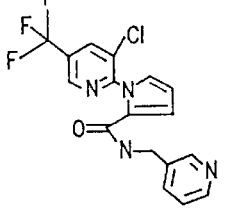 | 59-0428 | 380.756 | |
| 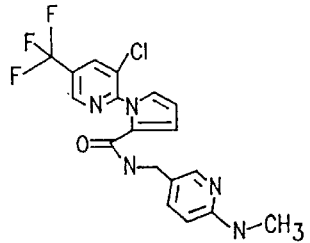 | 59-0429 | 409.793 | |
| 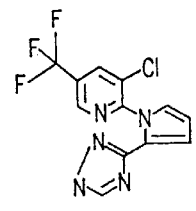 | 59.0430 | 313.669 | |
| 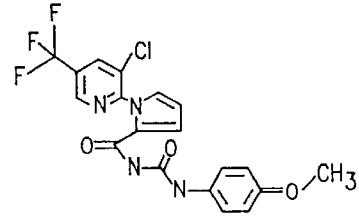 | 59-0431 | 454.859 | |
| 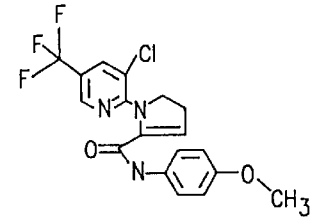 | 59-0432 | 395.767 | |
| 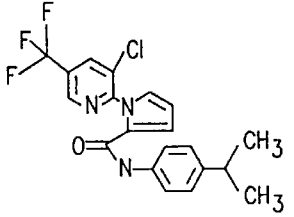 | 59-0433 | 407.821 | |
FIG. 13 II-I

| | | |
|---|---|---|
| 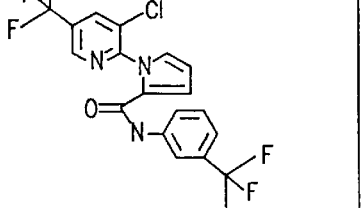 | 59-0435 | 433.738 |
| 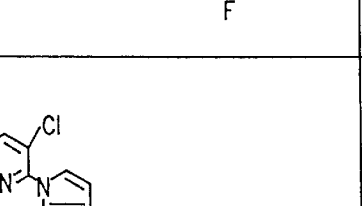 | 59-0436 | 444.637 |
| 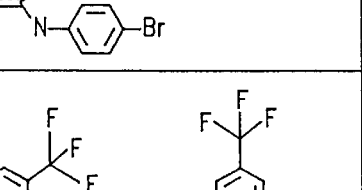 | 59-0439 | 525.826 |
FIG. 13 II-2

| Structure | No. | MW | |
|---|---|---|---|
| 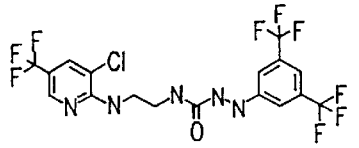 | 59-0440 | 525.826 | |
| 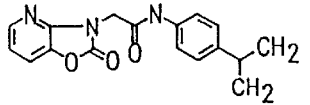 | 59-0441 | 311.339 | |
| 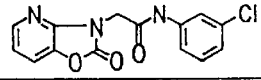 | 59-0442 | 303.704 | |
| 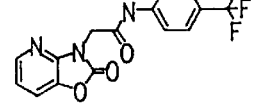 | 59-0443 | 337.256 | |
| 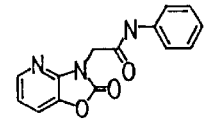 | 59-0444 | 269.259 | |
| 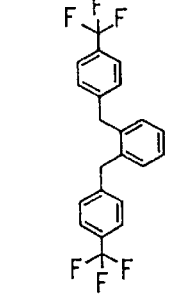 | 59-0445 | 404.356 | |
| 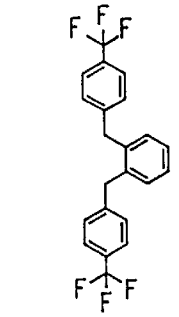 | 59-0446 | 404.356 | |
| 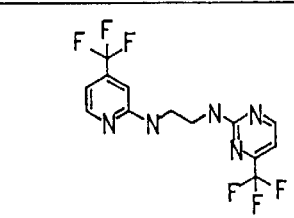 | 59-0447 | 352.241 | |
| 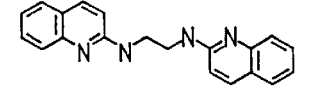 | 59-0448 | 314.39 | |
FIG. 13JJ-1

| | 59-0449 | 394.274 | |
| --- | --- | --- | --- |
| | 59-0450 | 329.281 | |
| | 59-0451 | 384.71 | |

FIG. 13JJ-2

| Structure | ID | MW | |
|---|---|---|---|
| H₃C-pyridine-NH-CH₂CH₂-NH-pyridine-CH₃ | 59-0452 | 242.324 | |
| pyridine-NH-CH₂CH₂-NH-pyridine | 59-0453 | 214.271 | |
| NC-pyridine-NH-CH₂CH₂-NH-pyridine-CN | 59-0454 | 264.291 | |
| H₃C(O)-pyridine-NH-CH₂CH₂-NH-pyridine-C(O)NH₂ | 59-0455 | 300.32 | |
| HO-N(O)-pyridine-NH-CH₂CH₂-NH-pyridine-N(O)-OH | 59-0056 | 308.296 | |
| H₃CO-C(O)-pyridine-NH-CH₂CH₂-NH-pyridine-C(O)-OCH₃ | 59-0457 | 330.342 | |
| (H₂C)₂N-pyridine-NH-CH₂CH₂-NH-pyridine-N(CH₂)₂ | 59-0458 | 300.408 | |
| F₃C-pyridine-NH-CH(CH₂)-CH₂-NH-pyridine-CF₃ | 59-0459 | 364.292 | |
| F₃C-pyridine-NH-CH₂-phenyl | 59-0460 | 252.238 | |
| F₃C-pyridine-NH-CH₂CH₂-phenyl | 59-0461 | 266.265 | |
| F₃C-pyridine-NH-CH₂CH₂CH₂-phenyl | 59-0462 | 280.292 | |
| F₃C-pyridine-NH-CH₂-pyridine | 59-0463 | 253.226 | |

FIG. 13KK

| Structure | ID | Value | |
|---|---|---|---|
| 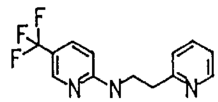 | 59-0464 | 267.253 | |
| 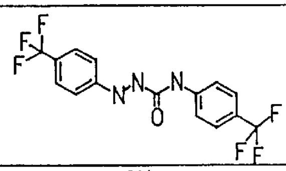 | 59-0465 | 363.26 | |
| 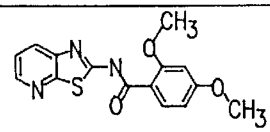 | 59-0466 | 315.352 | |
| 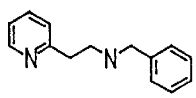 | 59-0467 | 212.294 | |
| 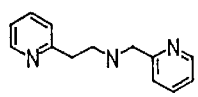 | 59-0468 | 213.283 | |
| 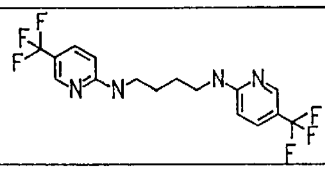 | 59-0469 | 378.318 | |
| 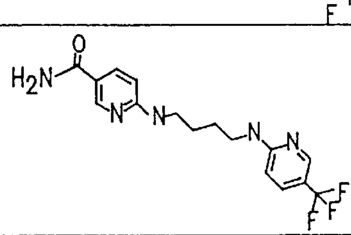 | 59-0470 | 325.293 | |
| 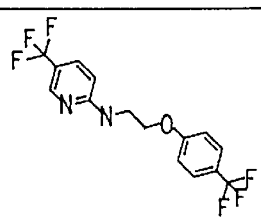 | 59-0471 | 350.261 | |
| 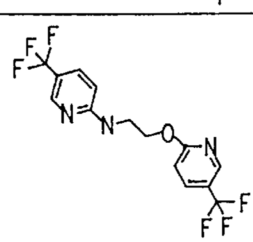 | 59-0472 | 351.249 | |

FIG. 13LL

| Structure | ID | Mass | |
|---|---|---|---|
| 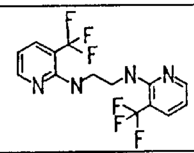 | 59-0476 | 350.265 | |
| 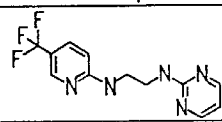 | 59-0477 | 283.256 | |
| 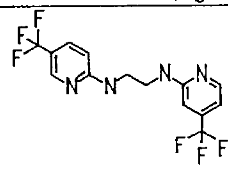 | 59-0478 | 351.253 | |
| 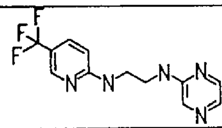 | 59-0479 | 283.256 | |
| 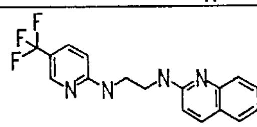 | 59-0480 | 332.328 | |
| 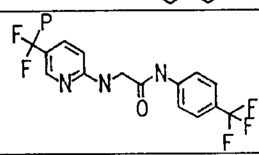 | 59-0481 | 363.26 | |
| 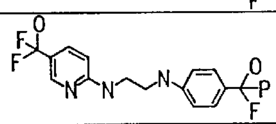 | 59-0482 | 349.277 | |
| 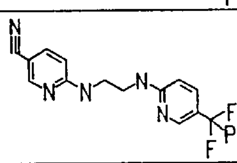 | 59-0483 | 307.278 | |
| 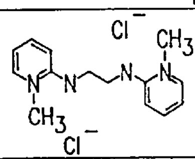 | 59-0484 | 315.246 | |
| 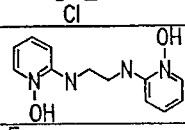 | 59-0485 | 250.3 | |
| 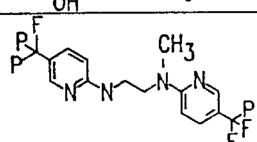 | 59-0486 | 364.292 | |
| 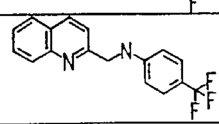 | 59-0487 | 302.298 | |

FIG. 13MM

| Structure | Number | Value | |
|---|---|---|---|
| (structure) | 59-0488 | 486.259 | |
| (structure) | 59-0489 | 255.3 | |
| (structure) | 59-0490 | 322.309 | |
| (structure) | 59-0491 | 317.269 | |
| (structure) | 59-0492 | 283.161 | |
| (structure) | 59-0493 | 364.248 | |
| (structure) | 59-0494 | 232.285 | |
| (structure) | 59-0495 | 299.294 | |
| (structure) | 59-0496 | 354.33 | |
| (structure) | 59-0497 | 340.303 | |
| (structure) | 59-0498 | 282.268 | |
| (structure) | 59-0499 | 296.294 | |

FIG. 13NN

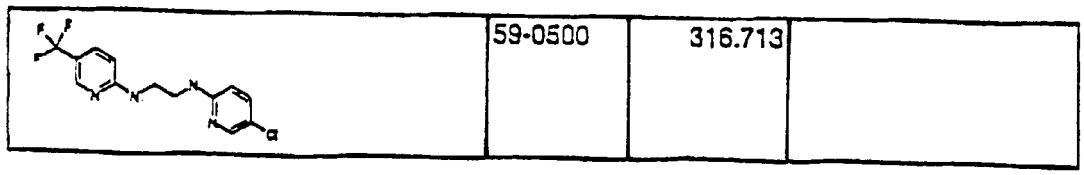
FIG. 1300

COMPOSITIONS AND METHODS FOR TREATING BONE DEFICIT CONDITIONS

This is a 371 of PCT/US97/18864 Oct. 23, 1997 now WO 98/17267.

TECHNICAL FIELD

The invention relates to compositions and methods for use in limiting undesired bone loss in a vertebrate at risk of such bone loss, in treating conditions that are characterized by undesired bone loss or by the need for bone growth, in treating fractures, and in treating cartilage disorders. More specifically, the invention concerns the use of specific classes of compounds identified or characterized by a high throughput screening assay.

BACKGROUND ART

Bone is not a static tissue. It is subject to constant breakdown and resynthesis in a complex process mediated by osteoblasts, which produce new bone, and osteoclasts, which destroy bone. The activities of these cells are regulated by a large number of cytokines and growth factors, many of which have now been identified and cloned. Mundy has described the current knowledge related to these factors (Mundy, G. R. *Clin Orthop* 324:24–28, 1996, Mundy, G. R. *J Bone Miner Res* 8:S505–10, 1993).

Although there is a great deal of information available on the factors which influence the breakdown and resorption of bone, information on growth factors which stimulate the formation of new bone is more limited. Investigators have searched for sources of such activities, and have found that bone tissue itself is a storehouse for factors which have the capacity for stimulating bone cells. Thus, extracts of bovine bone tissue obtained from slaughterhouses contain not only structural proteins which are responsible for maintaining the structural integrity of bone, but also biologically active bone growth factors which can stimulate bone cells to proliferate. Among these latter factors are transforming growth factor β, the heparin-binding growth factors (acidic and basic fibroblast growth factor), the insulin-like growth factors (insulin-like growth factor I and insulin-like growth factor II), and a recently described family of proteins called bone morphogenetic proteins (BMPs). All of these growth factors have effects on other types of cells, as well as on bone cells.

The BMPs are novel factors in the extended transforming growth factor β superfamily. They were first identified by Wozney J. et al. *Science* (1988) 242:1528–34, using gene cloning techniques, following earlier descriptions characterizing the biological activity in extracts of demineralized bone (Urist M. *Science* (1965) 150:893–99). Recombinant BMP2 and BMP4 can induce new bone formation when they are injected locally into the subcutaneous tissues of rats (Wozney J. *Molec Reprod Dev* (1992) 32:160–67). These factors are expressed by normal osteoblasts as they differentiate, and have been shown to stimulate osteoblast differentiation and bone nodule formation in vitro as well as bone formation in vivo (Harris S. et al. *J. Bone Miner Res* (1994) 9:855–63). This latter property suggests potential usefulness as therapeutic agents in diseases which result in bone loss.

The cells which are responsible for forming bone are osteoblasts. As osteoblasts differentiate from precursors to mature bone-forming cells, they express and secrete a number of enzymes and structural proteins of the bone matrix, including Type-1 collagen, osteocalcin, osteopontin and alkaline phosphatase (Stein G. et al. *Curr Opin Cell Biol* (1990) 2:1018–27, Harris S. et al. (1994), supra). They also synthesize a number of growth regulatory peptides which are stored in the bone matrix, and are presumably responsible for normal bone formation. These growth regulatory peptides include the BMPs (Harris S. et at (1994), supra). In studies of primary cultures of fetal rat calvarial osteoblasts, BMPs 1, 2, 3, 4, and 6 are expressed by cultured cells prior to the formation of mineralized bone nodules (Harris S. et al. (1994), supra). Like alkaline phosphatase, osteocalcin and osteopontin, the BMPs are expressed by cultured osteoblasts as they proliferate and differentiate.

Although the BMPs are potent stimulators of bone formation in vitro and in vivo, there are disadvantages to their use as therapeutic agents to enhance bone healing. Receptors for the bone morphogenetic proteins have been identified in many tissues, and the BMPs themselves are expressed in a large variety of tissues in specific temporal and spatial patterns. This suggests that BMPs may have effects on many tissues other than bone, potentially limiting their usefulness as therapeutic agents when administered systemically. Moreover, since they are peptides, they would have to be administered by injection. These disadvantages impose severe limitations to the development of BMPs as therapeutic agents.

There is a plethora of conditions which are characterized by the need to enhance bone formation. Perhaps the most obvious is the case of bone fractures, where it would be desirable to stimulate bone growth and to hasten and complete bone repair. Agents that enhance bone formation would also be useful in facial reconstruction procedures. Other bone deficit conditions include bone segmental defects, periodontal disease, metastatic bone disease, osteolytic bone disease and conditions where connective tissue repair would be beneficial, such as healing or regeneration of cartilage defects or injury. Also of great significance is the chronic condition of osteoporosis, including age-related osteoporosis and osteoporosis associated with postmenopausal hormone status. Other conditions characterized by the need for bone growth include primary and secondary hyperparathyroidism, disuse osteoporosis, diabetes-related osteoporosis, and glucocorticoid-related osteoporosis. In addition, or alternatively, the compounds of the present invention may modulate metabolism, proliferation and/or differentiation of normal or aberrant cells or tissues.

There are currently no satisfactory pharmaceutical approaches to managing any of these conditions. Bone fractures are still treated exclusively using casts, braces, anchoring devices and other strictly mechanical means. Further bone deterioration associated with postmenopausal osteoporosis has been decreased or prevented with estrogens or bisphosphonates.

U.S. Pat. No. 5,280,040 discloses a class of compounds which are 3,4-diaryl chromans. These compounds can be considered derivatives of 2,3,4 triphenyl butanol, where the hydroxy at the 1-position forms an ether with the ortho position of the phenyl group substituted at the 4-position of the butanol. The parent 3,4-diaryl chromans do not contain nitrogen atoms in the aromatic moieties or their linkers. A preferred compound, centchroman, contains a nitrogen substituent only in one of the substituents on a phenyl moiety. These compounds are disclosed in the '040 patent as useful in the treatment of osteoporosis.

In addition, the PCT application WO97/15308 published May 1, 1997 describes a number of classes of compounds that are active in the screening assay described below and are useful in treating bone disorders. These compounds, generically, are of the formulae

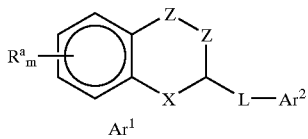

wherein $R^a$ is a non-interfering substituent;
m is an integer of 0–4;
each dotted line represents an optional π-bond;
each Z is independently N, NR, O, S, CR or $CR_2$, where each R is independently H or alkyl (1–6C);
X is O, S, SO or $SO_2$;
L is a flexible linker; and
$Ar^2$ is a substituted or unsubstituted 6-membered aromatic ring; or:

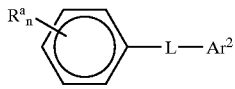

wherein $R^a$ is a non-interfering substituent,
n is an integer of 0 and 5;
L is a flexible linker which does not contain nitrogen or is a constrained linker; and
$Ar^2$ is a substituted or unsubstituted phenyl or a substituted or unsubstituted naphthyl.

There remains a need for additional compositions which can ameliorate the effects of abnormalities in bone formation or resorption. The present invention expands the repertoire of compounds useful for limiting or treating bone deficit conditions, and for other uses that should be apparent to those skilled in the art from the teachings herein.

DISCLOSURE OF THE INVENTION

The invention provides compounds that can be administered as ordinary pharmaceuticals and have the metabolic effect of enhancing bone growth or inhibiting resorption. The compounds of the invention can be identified using an assay for their ability to activate control elements associated with bone anabolic factors. Thus, the invention is directed to methods and compositions for treating bone disorders, which methods and compositions use, as active ingredients, compounds wherein two aromatic systems are coupled so as to be spaced apart from each other by about 1.5 to about 15 Angstroms. The thus-linked systems (including the linker coupling them) preferably include at least one nitrogen atom.

Therefore, the compounds useful in the invention can be described as having the formula $Ar^1$-linker-$Ar^2$, wherein each of $Ar^1$ and $Ar^2$ is independently an aromatic system and the linker portion of the formula spaces $Ar^1$ and $Ar^2$ apart by a distance of approximately 1.5–15 Angstroms. $Ar^1$, $Ar^2$ and the linker may optionally be substituted with non interfering substituents. In the useful compounds, there is preferably at least one nitrogen atom in either $AR^1$, $Ar^2$ and/or the linker, independent of any substituents thereon. Preferably, the compounds of the invention contain at least one additional heteroatom selected from the group consisting of N, S and O, independent of any substituent.

Thus, in one aspect, the invention is directed to a method to treat a condition in a vertebrate animal characterized by a deficiency in, or need for, bone growth replacement and/or an undesirable level of bone resorption, which method comprises administering to a vertebrate subject in need of such treatment an effective amount of certain compounds of the formula:

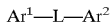

wherein each of $Ar^1$ and $Ar^2$ is independently substituted or unsubstituted phenyl, substituted or unsubstituted naphthyl, a substituted or unsubstituted aromatic system containing a 6-membered heterocycle, or a substituted or unsubstituted aromatic system containing a 5-membered heterocycle; and L is a linker that provides spacing of 1.5–15 Å.

In other aspects, the invention relates to pharmaceutical compositions for use in the method, and to the compounds for use in preparing a medicament for use in the method.

BRIEF DESCRIPTION OF THE DRAWINGS

FIG. 1 gives a schematic representation of the compounds used as active ingredients in the methods and compositions of the invention.

FIGS. 3 thru 4BB show illustrative compounds of the invention and the results obtained with them in an in vitro test for stimulation of bone growth.

FIGS. 6A, 6B and 6C show structures and results of a screening assay for a group of compounds which varies the parameters of lead compound 50-0197.

FIG. 7 shows structures and results of a screening assay for a group of compounds which varies the parameters of lead compound 59-0145.

FIG. 9 shows the results in an ex vivo calvarial assay for various compunds of the invention.

FIG. 13 (A–OO)(41 pages) is a list of compounds used in screening for bone morphogenic activity according to the screening assay set forth herein.

MODES OF CARRYING OUT THE INVENTION

Figure 2:
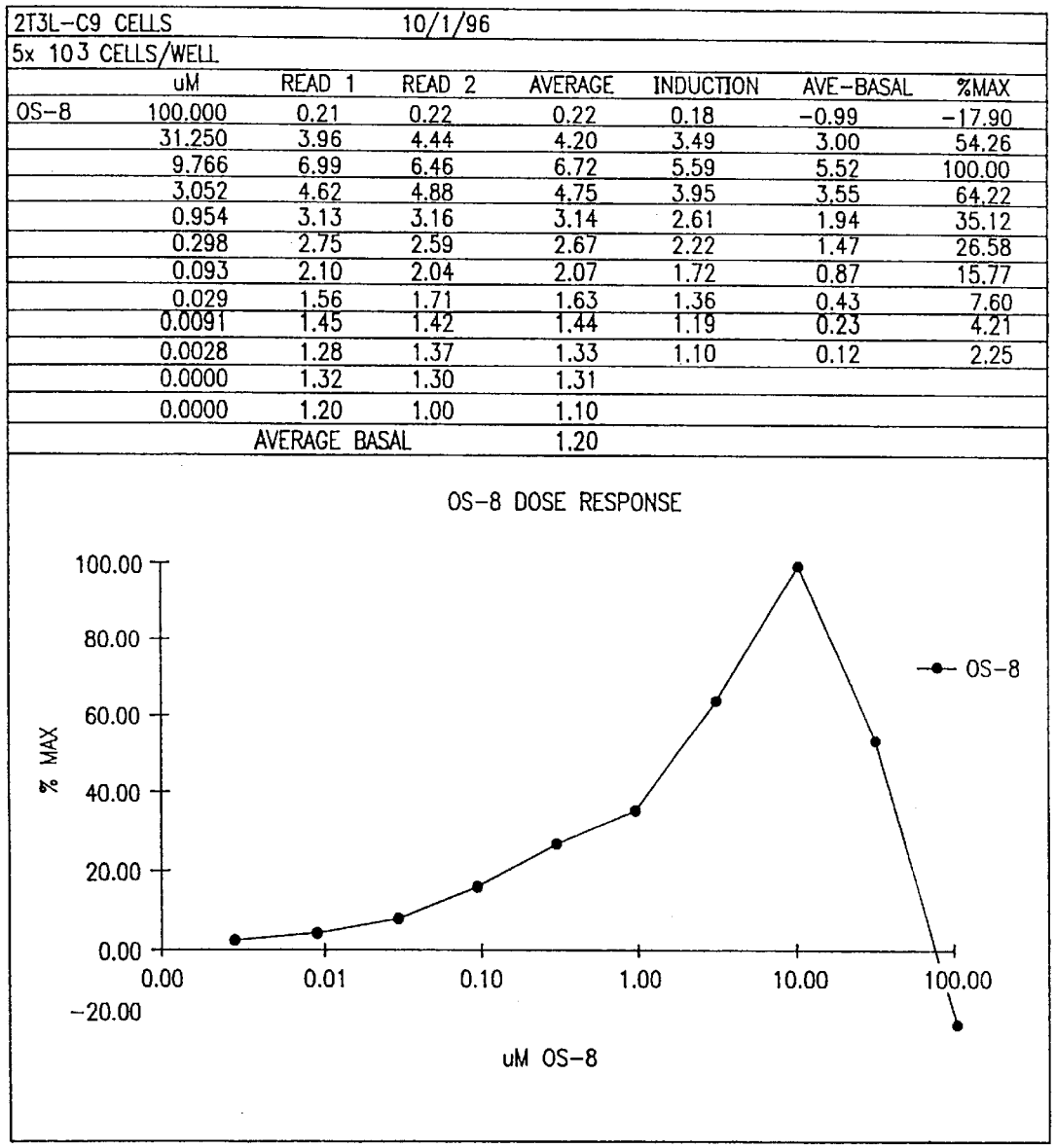
FIG. 2 shows the dose response curve for a positive control compound, designated 59-0008.
Figure 4J:
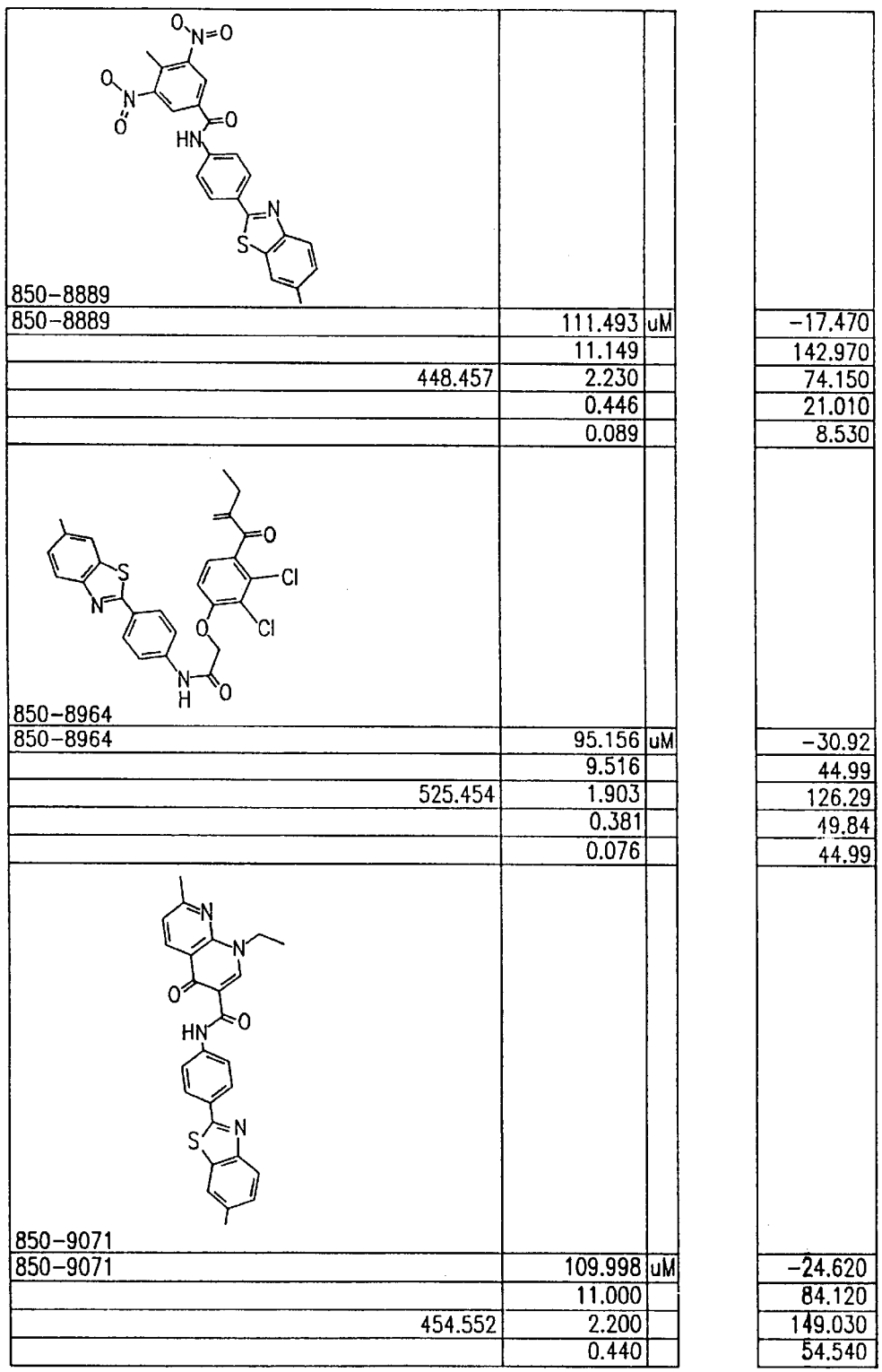
Figure 4M:
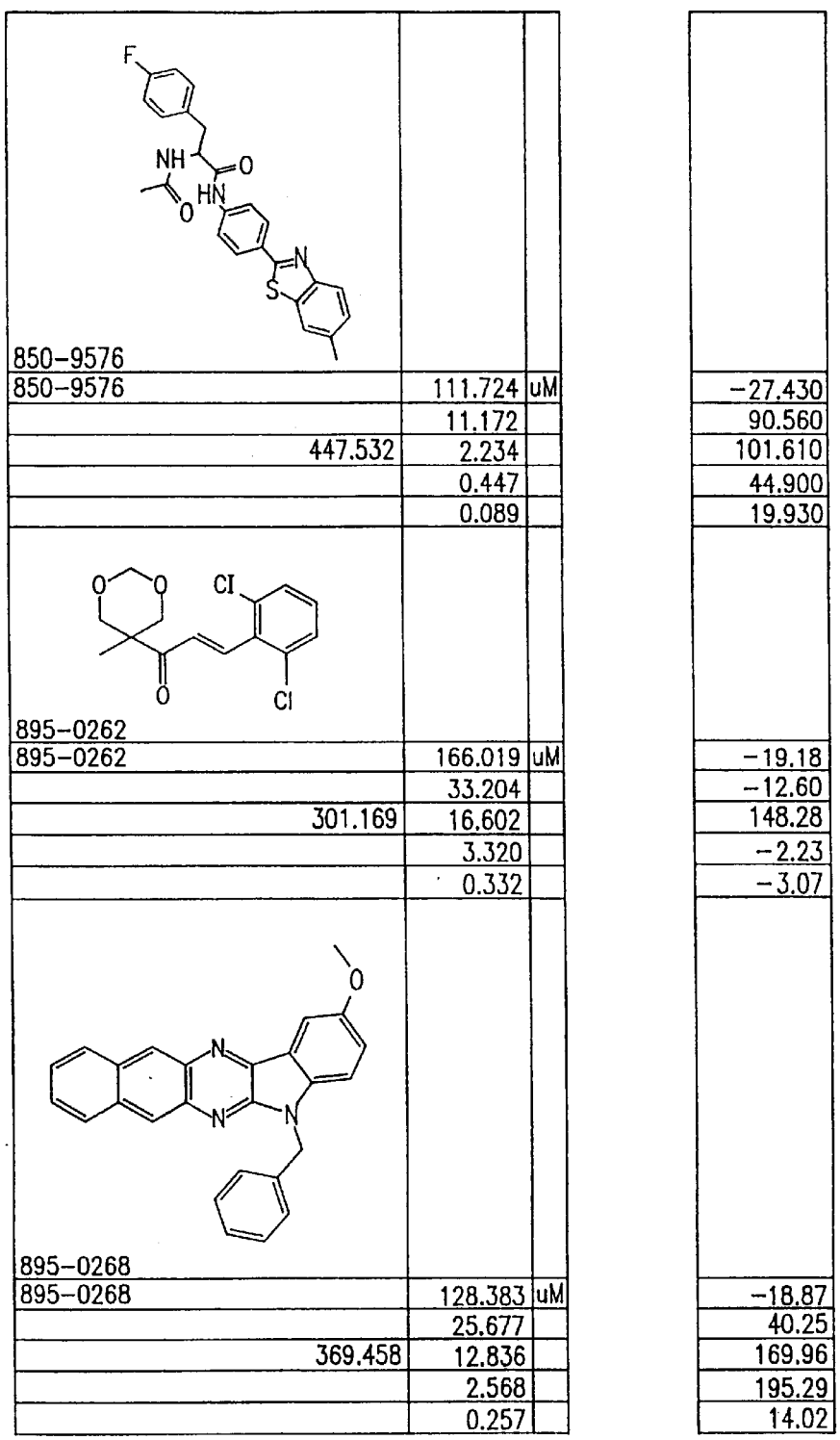
Figure 4V:
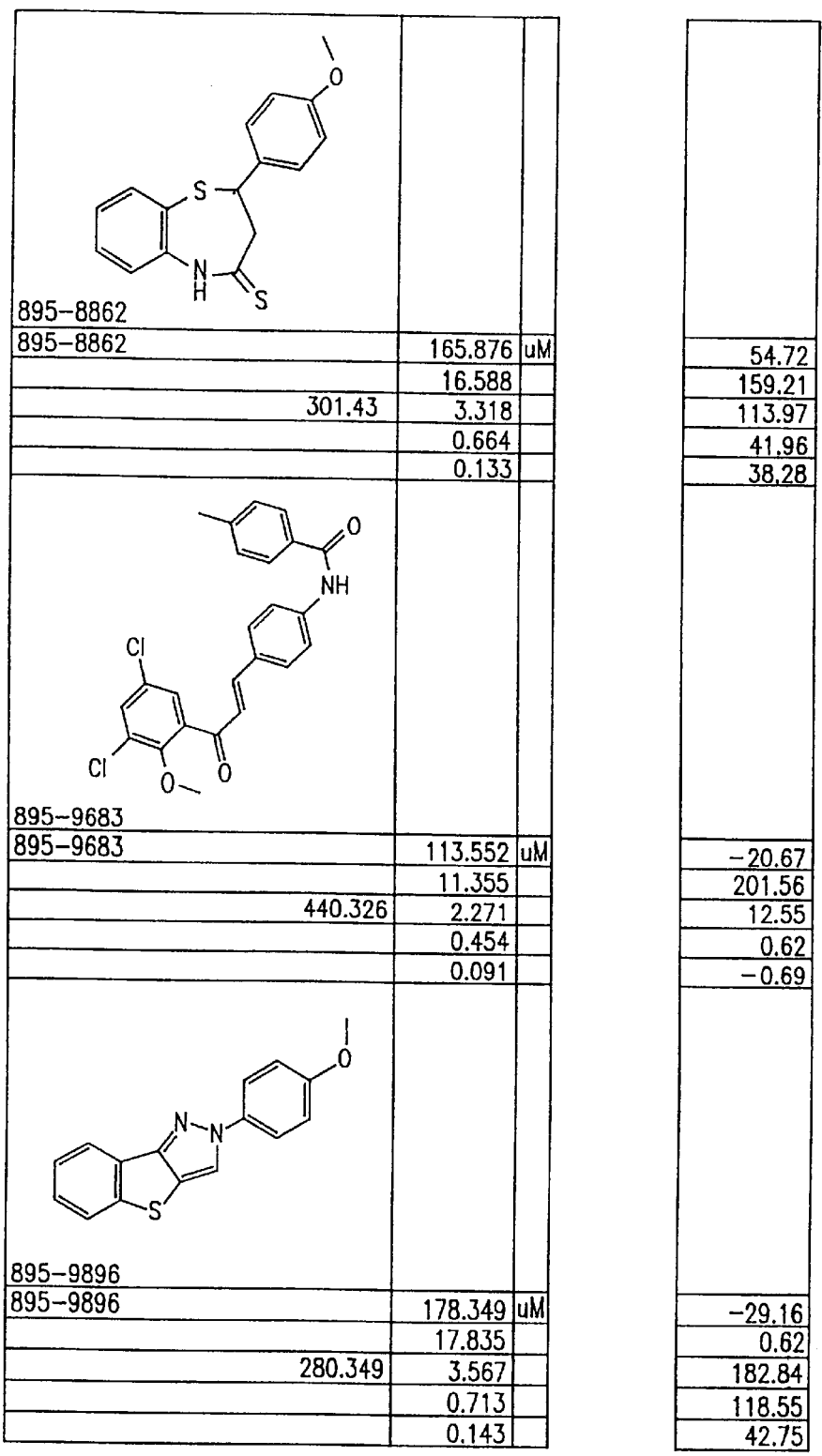
Figure 4B:
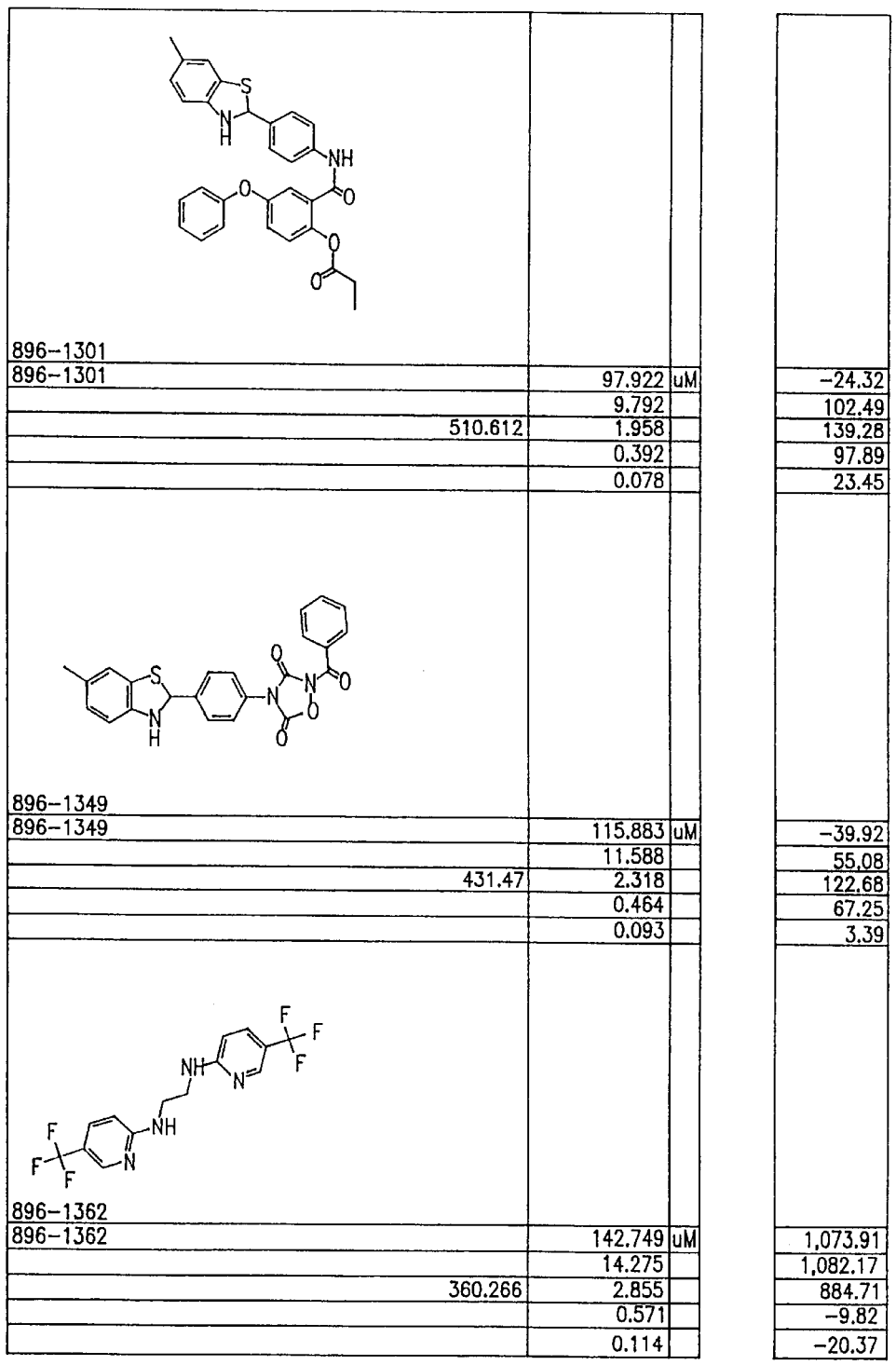

A rapid throughput screening test for compounds capable of stimulating expression of a reporter gene linked to a BMP promoter (a surrogate for the production of bone morphogenetic factors that are endogenously produced) is described in WO96/38590 published Dec. 5, 1996, the contents of which are incorporated herein by reference. This assay is also described as a portion of a study of immortalized murine osteoblasts (derived from a mouse expressing a transgene composed of a BMP2 promoter driving expression of T-antigen) in Ghosh-Choudhery, N. et al. *Endocrinology* (1996) 137:331–39. In this study, the immortalized cells were stably transfected with a plasmid containing a luciferase reporter gene driven by a mouse BMP2 promoter (−2736/114 bp), and responded in a dose-dependent manner to recombinant human BMP2.

Briefly, the assay utilizes cells transformed permanently or transiently with constructs in which the promoter of a bone morphogenetic protein, specifically BMP2 or BMP4, is coupled to a reporter gene, typically luciferase. These transformed cells are then evaluated for the production of the reporter gene product; compounds that activate the BMP promoter will drive production of the reporter protein, which can be readily assayed. Over 40,000 compounds have been subjected to this rapid screening technique, and only a very small percentage are able to elicit a level of production of luciferase 5-fold greater than that produced by vehicle. Compounds that activate the BMP promoter share certain structural characteristics not present in inactive compounds. The active compounds ("BMP promoter-active compounds" or "active compounds") are useful in promoting bone or cartilage growth, and thus in the treatment of vertebrates in need of bone or cartilage growth.

BMP promoter-active compounds can be examined in a variety of other assays that test specificity and toxicity. For instance, nonBMP promoters or response elements can be linked to a reporter gene and inserted into an appropriate host cell. Cytotoxicity can be determined by visual or microscopic examination of BMP promoter- and/or non-BMP promoter-reporter gene-containing cells, for instance. Alternatively, nucleic acid and/or protein synthesis by the cells can be monitored. For in vivo assays, tissues may be removed and examined visually or microscopically, and optionally examined in conjunction with dyes or stains that facilitate histologic examination. In assessing in vivo assay results, it may also be useful to examine biodistribution of the test compound, using conventional medicinal chemistry/animal model techniques.

As used herein, "limit" or "limiting" and "treat" or "treatment" are interchangeable terms. The terms include a postponement of development of bone deficit symptoms and/or a reduction in the severity of such symptoms that will or are expected to develop. The terms further include ameliorating existing bone or cartilage deficit symptoms, preventing additional symptoms, ameliorating or preventing the underlying metabolic causes of symptoms, preventing or reversing bone resorption and/or encouraging bone growth. Thus, the terms denote that a beneficial result has been conferred on a vertebrate subject with a cartilage, bone or skeletal deficit, or with the potential to develop such deficit.

By "bone deficit" is meant an imbalance in the ratio of bone formation to bone resorption, such that, if unmodified, the subject will exhibit less bone than desirable, or the subject's bones will be less intact and coherent than desired. Bone deficit may also result from fracture, from surgical intervention or from dental or periodontal disease. By "cartilage defect" is meant damaged cartilage, less cartilage than desired, or cartilage that is less intact and coherent than desired.

Representative uses of the compounds of the present invention include: repair of bone defects and deficiencies, such as those occuring in closed, open and nonunion fractures; prophylactic use in closed and open fracture reduction; promotion of bone healing in plastic surgery; stimulation of bone ingrowth into noncemented prosthetic joints and dental implants; elevation of peak bone mass in premenopausal women; treatment of growth deficiencies; treatment of peridontal disease and defects, and other tooth repair processes; increase in bone formation during distraction osteogenesis; and treatment of other skeletal disorders, such as age-related osteoporosis, postmenopausal osteoporosis, glucocorticoid-induced osteoporosis or disuse osteoporosis and arthritis. The compounds of the present invention can also be useful in repair of congenital, trauma-induced or surgical resection of bone (for instance, for cancer treatment), and in cosmetic surgery. Further, the compounds of the present invention can be used for limiting or treating cartilage defects or disorders, and may be useful in wound healing or tissue repair.

Bone or cartilage deficit or defect can be treated in vertebrate subjects by administering compounds of the invention which have been identified through suitable screening assays and which exhibit certain structural characteristics. The compositions of the invention may be administered systemically or locally. For systemic use, the compounds herein are formulated for parenteral (e.g., intravenous, subcutaneous, intramuscular, intraperitoneal, intranasal or transdermal) or enteral (e.g., oral or rectal) delivery according to conventional methods. Intravenous administration will be by a series of injections or by continuous infusion over an extended period. Administration by injection or other routes of discretely spaced administration will generally be performed at intervals ranging from weekly to once to three times daily. Alternatively, the compounds disclosed herein may be administered in a cyclical manner (administration of disclosed compound; followed by no administration; followed by administration of disclosed compound, and the like). Treatment will continue until the desired outcome is achieved. In general, pharmaceutical formulations will include a compound of the present invention in combination with a pharmaceutically acceptable vehicle, such as saline, buffered saline, 5% dextrose in water, borate-buffered saline containing trace metals or the like. Formulations may further include one or more excipients, preservatives, solubilizers, buffering agents, albumin to prevent protein loss on vial surfaces, lubricants, fillers, stabilizers, etc. Methods of formulation are well known in the art and are disclosed, for example, in *Remington's Pharmaceutical Sciences*, Gennaro, ed., Mack Publishing Co., Easton Pa., 1990, which is incorporated herein by reference. Pharmaceutical compositions for use within the present invention can be in the form of sterile, nonpyrogenic liquid solutions or suspensions, coated capsules, suppositories, lyophilized powders, transdermal patches or other forms known in the art. Local administration may be by injection at the site of injury or defect, or by insertion or attachment of a solid carrier at the site, or by direct, topical application of a viscous liquid. For local administration, the delivery vehicle preferably provides a matrix for the growing bone or cartilage, and more preferably is a vehicle that can be absorbed by the subject without adverse effects.

Delivery of compounds herein to wound sites may be enhanced by the use of controlled-release compositions, such as those described in WIPO publication WO 93/20859, which is incorporated herein by reference in its entirety. Films of this type are particularly useful as coatings for prosthetic devices and surgical implants. The films may, for example, be wrapped around the outer surfaces of surgical screws, rods, pins, plates and the like. Implantable devices of this type are routinely used in orthopedic surgery. The films can also be used to coat bone filling materials, such as hydroxyapatite blocks, demineralized bone matrix plugs, collagen matrices and the like. In general, a film or device as described herein is applied to the bone at the fracture site. Application is generally by implantation into the bone or attachment to the surface using standard surgical procedures.

In addition to the copolymers and carriers noted above, the biodegradable films and matrices may include other active or inert components. Of particular interest are those agents that promote tissue growth or infiltration, such as growth factors. Exemplary growth factors for this purpose include epidermal growth factor (EGF), fibroblast growth factor (FGF), platelet-derived growth factor (PDGF), transforming growth factors (TGFs), parathyroid hormone (PTH), leukemia inhibitory factor (LIF), and insulin-like growth factors (IGFs). Agents that promote bone growth, such as bone morphogenetic proteins (U.S. Pat. No. 4,761, 471; PCT Publication WO 90/11366), osteogenin (Sampath et al. *Proc. Natl. Acad. Sci. USA* (1987) 84:7109–13) and NaF (Tencer et al. *J. Biomed. Mat. Res.* (1989) 23: 571–89) are also preferred. Biodegradable films or matrices include calcium sulfate, tricalcium phosphate, hydroxyapatite, polylactic acid, polyanhydrides, bone or dermal collagen, pure proteins, extracellular matrix components and combinations thereof. Such biodegradable materials may be used in combination with nonbiodegradable materials, to provide desired mechanical, cosmetic or tissue or matrix interface properties.

Alternative methods for delivery of compounds of the present invention include use of ALZET osmotic minipumps (Alza Corp., Palo Alto, Calif.); sustained release matrix materials such as those disclosed in Wang et al. (PCT Publication WO 90/11366); electrically charged dextran beads, as disclosed in Bao et al. (PCT Publication WO 92/03125); collagen-based delivery systems, for example, as disclosed in Ksander et al. *Ann. Surg.* (1990) 211(3):288–94; methylcellulose gel systems, as disclosed in Beck et al. *J. Bone Min. Res.* (1991) 6(11):1257–65; and alginate-based systems, as disclosed in Edelman et al. *Biomaterials* (1991) 12:619–26. Other methods well known in the art for sustained local delivery in bone include porous coated metal protheses that can be impregnated and solid plastic rods with therapeutic compositions incorporated within them.

The compounds of the present invention may also be used in conjunction with agents that inhibit bone resorption. Antiresorptive agents, such as estrogen, bisphosphonates and calcitonin, are preferred for this purpose. More specifically, the compounds disclosed herein may be administered for a period of time (for instance, months to years) sufficient to obtain correction of a bone deficit condition. Once the bone deficit condition has been corrected, the vertebrate can be administered an anti-resorptive compound to maintain the corrected bone condition. Alternatively, the compounds disclosed herein may be adminstered with an anti-resorptive compound in a cyclical manner (administration of disclosed compound, followed by anti-resorptive, followed by disclosed compound, and the like).

In additional formulations, conventional preparations such as those described below may be used.

Aqueous suspensions may contain the active ingredient in admixture with pharmacologically acceptable excipients, comprising suspending agents, such as methyl cellulose; and wetting agents, such as lecithin, lysolethicin or long-chain fatty alcohols. The said aqueous suspensions may also contain preservatives, coloring agents, flavoring agents and sweetening agents in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure.

If desired, the osteogenic agents can be incorporated into liposomes by any of the reported methods of preparing liposomes for use in treating various pathogenic conditions. The present compositions may utilize the compounds noted above incorporated in liposomes in order to direct these compounds to macrophages, monocytes, other cells and tissues and organs which take up the liposomal composition. The liposome-incorporated compounds of the invention can be utilized by parenteral administration, to allow for the efficacious use of lower doses of the compounds. Ligands may also be incorporated to further focus the specificity of the liposomes.

Suitable conventional methods of liposome preparation include, but are not limited to, those disclosed by Bangham, A. D. et al. *J Mol Biol* (1965) 23:238–252, Olson, F. et al. *Biochim Biophys Acta* (1979) 557:9–23, Szoka, F. et al. *Proc Natl Acad Sci USA* (1978) 75:4194–4198, Mayhew, E. et al. *Biochem, Biophys. Acta* (1984) 775:169–175, Kim, S. et al. *Biochim Biophys Acta* (1983) 728:339:348, and Mayer, et al. *Biochim Biophys Acta* (1986) 858:161–168.

The liposomes may be made from the present compounds in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine, or phosphatidylinositol. Synthetic phospholipids that may also be used, include, but are not limited to: dimyristoylphosphatidylcholine, dioleoylphosphatidylcholine, dipalmitoylphosphatidylcholine and distearoylphosphatidycholine, and the corresponding synthetic phosphatidylethanolamines and phosphatidylglycerols. Cholesterol or other sterols, cholesterol hemisuccinate, glycolipids, cerebrosides, fatty acids, gangliosides, sphingolipids, 1,2-bis(oleoyloxy)-3-(trimethyl ammonio)propane (DOTAP), N-[1-(2,3-dioleoyl)propyl-N, N,N-trimethylammonium chloride (DOTMA), and other cationic lipids may be incorporated into the liposomes, as is known to those skilled in the art. The relative amounts of phospholipid and additives used in the liposomes may be varied if desired. The preferred ranges are from about 60 to 90 mole percent of the phospholipid; cholesterol, cholesterol hemisuccinate, fatty acids or cationic lipids may be used in amounts ranging from 0 to 50 mole percent. The amounts of the present compounds incorporated into the lipid layer of liposomes can be varied with the concentration of their lipids ranging from about 0.01 to about 50 mole percent.

Using conventional methods, approximately 20 to 30% of the compound present in solution can be entrapped in liposomes; thus, approximately 70 to 80% of the active compound is wasted. In contrast, where the compound is incorporated into liposomes, virtually all of the compound is incorporated into the liposome, and essentially none of the active compound is wasted.

The liposomes with the above formulations may be made still more specific for their intended targets with the incorporation of monoclonal antibodies or other ligands specific for a target. For example, monoclonal antibodies to the BMP receptor may be incorporated into the liposome by linkage to phosphatidylethanolamine (PE) incorporated into the liposome by the method of Leserman, L. et al. *Nature* (1980) 288:602–604.

Veterinary uses of the disclosed compounds are also contemplated. Such uses would include limitation or treatment of bone or cartilage deficits or defects in domestic animals, livestock and thoroughbred horses. The compounds described herein can also modify a target tissue or organ environment, so as to attract bone-forming cells to an environment in need of such cells.

The compounds of the present invention may also be used to stimulate growth of bone-forming cells or their precursors, or to induce differentiation of bone-forming cell precursors, either in vitro or ex vivo. As used herein, the term "precursor cell" refers to a cell that is committed to a differentiation pathway, but that generally does not express markers or function as a mature, fully differentiated cell. As used herein, the term "mesenchymal cells" or "mesenchymal stem cells" refers to pluripotent progenitor cells that are capable of dividing many times, and whose progeny will give rise to skeletal tissues, including cartilage, bone, tendon, ligament, marrow stroma and connective tissue (see A. Caplan *J. Orthop. Res.* (1991) 9:641–50). As used herein, the term "osteogenic cells" includes osteoblasts and osteoblast precursor cells. More particularly, the disclosed compounds are useful for stimulating a cell population containing marrow mesenchymal cells, thereby increasing the number of osteogenic cells in that cell population. In a preferred method, hematopoietic cells are removed from the cell population, either before or after stimulation with the disclosed compounds. Through practice of such methods, osteogenic cells may be expanded. The expanded osteogenic cells can be infused (or reinfused) into a vertebrate subject in need thereof. For instance, a subject's own mesenchymal stem cells can be exposed to compounds of the present invention ex vivo, and the resultant osteogenic cells could be infused or directed to a desired site within the subject, where further proliferation and/or differentiation of the osteogenic cells can occur without immunorejection. Alternatively, the cell population exposed to the disclosed compounds may be immortalized human fetal osteoblastic or osteogenic cells. If such cells are infused or implanted in a vertebrate subject, it may be advantageous to "immunoprotect" these nonself cells, or to immunosuppress (preferably locally) the recipient to enhance transplantation and bone or cartilage repair.

Within the present invention, an "effective amount" of a composition is that amount which produces a statistically significant effect. For example, an "effective amount" for therapeutic uses is the amount of the composition comprising an active compound herein required to provide a clinically significant increase in healing rates in fracture repair; reversal of bone loss in osteoporosis; reversal of cartilage defects or disorders; prevention or delay of onset of osteoporosis; stimulation and/or augmentation of bone formation in fracture nonunions and distraction osteogenesis; increase and/or acceleration of bone growth into prosthetic devices; and repair of dental defects. Such effective amounts will be determined using routine optimization techniques and are dependent on the particular condition to be treated, the condition of the patient, the route of administration, the formulation, and the judgment of the practitioner and other factors evident to those skilled in the art. The dosage required for the compounds of the invention (for example, in osteoporosis where an increase in bone formation is desired) is manifested as a statistically significant difference in bone mass between treatment and control groups. This difference in bone mass may be seen, for example, as a 5–20% or more increase in bone mass in the treatment group. Other measurements of clinically significant increases in healing may include, for example, tests for breaking strength and tension, breaking strength and torsion, 4-point bending, increased connectivity in bone biopsies and other biomechanical tests well known to those skilled in the art. General guidance for treatment regimens is obtained from experiments carried out in animal models of the disease of interest.

The dosage of the compounds of the invention will vary according to the extent and severity of the need for treatment, the activity of the administered compound, the general health of the subject, and other considerations well known to the skilled artisan. Generally, they can be administered to a typical human on a daily basis on an oral dose of about 0.1 mg/kg–1000 mg/kg, and more preferably from about 1 mg/kg to about 200 mg/kg. The parenteral dose will appropriately be 20–100% of the oral dose.

Screening Assays

The osteogenic activity of the compounds used in the methods of the invention can be verified using in vitro screening techniques, such as the assessment of transcription of a reporter gene coupled to a bone morphogenetic protein-associated promoter, as described above, or in alternative assays such as the following:

Technique for Neonatal Mouse Calvarial Assay (In vitro)

This assay is similar to that described by Gowen M. & Mundy G. *J Immunol* (1986) 136:2478–82. Briefly, four days after birth, the front and parietal bones of ICR Swiss white mouse pups are removed by microdissection and split along the sagittal suture. The bones are incubated in BGJb medium (Irvine Scientific, Santa Ana, Calif.) plus 0.02% (or lower concentration) β-methylcyclodextrin, wherein the medium also contains test or control substances, at 37° C. in a humidified atmosphere of 5% $CO_2$ and 95% air for 96 hours.

Following this, the bones are removed from the incubation media and fixed in 10% buffered formalin for 24–48 hours, decalcified in 14% EDTA for 1 week, processed through graded alcohols; and embedded in paraffin wax. Three µm sections of the calvaria are prepared. Representative sections are selected for histomorphometric assessment of bone formation and bone resorption. Bone changes are measured on sections cut 200 µm apart. Osteoblasts and osteoclasts are identified by their distinctive morphology.

Other auxiliary assays can be used as controls to determine nonBMP promoter-mediated effects of test compounds. For example, mitogenic activity can be measured using screening assays featuring a serum-response element (SRE) as a promoter and a luciferase reporter gene. More specifically, these screening assays can detect signalling through SRE-mediated pathways, such as the protein kinase C pathway. For instance, an osteoblast activator SRE-luciferase screen and an insulin mimetic SRE-luciferase screen are useful for this purpose. Similarly, test compound stimulation of cAMP response element (CRE)-mediated pathways can also be assayed. For instance, cells transfected with receptors for PTH and calcitonin (two bone-active agents) can be used in CRE-luciferase screens to detect elevated cAMP levels. Thus, the BMP promoter specificity of a test compound can be examined through use of these types of auxiliary assays.

In vivo Assay of Effects of Compounds on Murine Calvarial Bone Growth

Male ICR Swiss white mice, aged 4–6 weeks and weighing 13–26 gm, are employed, using 4–5 mice per group. The calvarial bone growth assay is performed as described in PCT application WO 95/24211. Briefly, the test compound or appropriate control vehicle is injected into the subcutaneous tissue over the right calvaria of normal mice. Typically, the control vehicle is the vehicle in which the compound was solubilized, and is PBS containing 5% DMSO or is PBS containing Tween (2 µl/10 ml). The animals are sacrificed on day 14 and bone growth measured by histomorphometry. Bone samples for quantitation are cleaned from adjacent tissues and fixed in 10% buffered formalin for 24–48 hours, decalcified in 14% EDTA for 1–3 weeks, processed through graded alcohols; and embedded in paraffin wax. Three to five µm sections of the calvaria are prepared, and representative sections are selected for histomorphometric assessment of the effects on bone formation and bone resorption. Sections are measured by using a camera lucida attachment to trace directly the microscopic image onto a digitizing plate. Bone changes are measured on sections cut 200 µm apart, over 4 adjacent 1×1 mm fields on both the injected and noninjected sides of the calvaria. New bone is identified by its characteristic woven structure, and osteoclasts and osteoblasts are identified by their distinctive morphology. Histomorphometry software (OsteoMeasure, Osteometrix, Inc., Atlanta) is used to process digitizer input to determine cell counts and measure areas or perimeters.

Additional In Vivo Assays

Lead compounds can be further tested in intact animals using an in vivo, dosing assay. Prototypical dosing may be accomplished by subcutaneous, intraperitoneal or oral administration, and may be performed by injection, sustained release or other delivery techniques. The time period for administration of test compound may vary (for instance, 28 days as well as 35 days may be appropriate). An exemplary, in vivo subcutaneous dosing assay may be conducted as follows:

In a typical study, 70 three-month-old female Sprague-Dawley rats are weight-matched and divided into seven groups, with ten animals in each group. This includes a baseline control group of animals sacrificed at the initiation of the study; a control group administered vehicle only; a PBS-treated control group; and a positive control group administered a compound (nonprotein or protein) known to promote bone growth. Three dosage levels of the compound to be tested are administered to the remaining three groups.

Briefly, test compound, positive control compound, PBS, or vehicle alone is administered subcutaneously once per day for 35 days. All animals are injected with calcein nine days and two days before sacrifice (two injections of calcein administered each designated day). Weekly body weights are determined. At the end of the 35-day cycle, the animals are weighed and bled by orbital or cardiac puncture. Serum calcium, phosphate, osteocalcin, and CBCs are determined. Both leg bones (femur and tibia) and lumbar vertebrae are removed, cleaned of adhering soft tissue, and stored in 70% ethanol for evaluation, as performed by peripheral quantitative computed tomography (pqCT; Ferretti, J. *Bone* (1995) 17:353S–64S), dual energy X-ray absorptiometry (DEXA; Laval-Jeantet A. et al. *Calcif Tissue Intl* (1995) 56:14–18; J. Casez et al. *Bone and Mineral* (1994) 26:61–68) and/or histomorphometry. The effect of test compounds on bone remodeling can thus be evaluated.

Lead compounds also be tested in acute ovariectomized animals (prevention model) using an in vivo dosing assay. Such assays may also include an estrogen-treated group as a control. An exemplary subcutaneous dosing assay is performed as follows:

In a typical study, 80 three-month-old female Sprague-Dawley rats are weight-matched and divided into eight groups, with ten animals in each group. This includes a baseline control group of animals sacrificed at the initiation of the study; three control groups (sham ovariectomized (sham OVX)+vehicle only; ovariectomized (OVX)+vehicle only; PBS-treated OVX); and a control OVX group that is administered a compound known to promote bone growth. Three dosage levels of the compound to be tested are administered to the remaining three groups of OVX animals.

Since ovariectomy (OVX) induces hyperphagia, all OVX animals are pair-fed with sham OVX animals throughout the 35 day study. Briefly, test compound, positive control compound, PBS, or vehicle alone is administered subcutaneously once per day for 35 days. Alternatively, test compound can be formulated in implantable pellets that are implanted for 35 days, or may be administered orally, such as by gastric gavage. All animals, including sham OVX/vehicle and OVX/vehicle groups, are injected intraperitoneally with calcein nine days and two days before sacrifice (two injections of calcein administered each designated day, to ensure proper labeling of newly formed bone). Weekly body weights are determined. At the end of the 35-day cycle, the animals' blood and tissues are processed as described above.

Lead compounds may also be tested in chronic OVX animals (treatment model). An exemplary protocol for treatment of established bone loss in ovariectomized animals that can be used to assess efficacy of anabolic agents may be performed as follows. Briefly, 80 to 100 six month old female, Sprague-Dawley rats are subjected to sham surgery (sham OVX) or ovariectomy (OVX) at time 0, and 10 rats are sacrificed to serve as baseline controls. Body weights are recorded weekly during the experiment. After approximately 6 weeks of bone depletion (42 days), 10 sham OVX and 10 OVX rats are randomly selected for sacrifice as depletion period controls. Of the remaining animals, 10 sham OVX and 10 OVX rats are used as placebo-treated controls. The remaining OVX animals are treated with 3 to 5 doses of test drug for a period of 5 weeks (35 days). As a postitive control, a group of OVX rats can be treated with an agent such as PTH, a known anabolic agent in this model (Kimmel et al. *Endocrinology* (1993) 132:1577–84). To determine effects on bone formation, the following procedure can be followed. The femurs, tibiae and lumbar vertebrae 1 to 4 are excised and collected. The proximal left and right tibiae are used for pqCT measurements, cancellous bone mineral density (BMD) (gravimetric determination), and histology, while the midshaft of each tibiae is subjected to cortical BMD or histology. The femurs are prepared for pqCT scanning of the midshaft prior to biomechanical testing. With respect to lumbar vertebrae (LV), LV2 are processed for BMD (pqCT may also be performed); LV3 are prepared for undecalcified bone histology; and LV4 are processed for mechanical testing.

Nature of the Compounds Useful in the Invention

All of the compounds of the invention contain two aromatic systems, $Ar^1$ and $AR^2$, spaced apart by a linker at a distance of 1.5–15 Å, and may preferably contain at least one nitrogen atom. A summary of the structural features of the compounds included within the invention is shown in FIG. 1.

As shown, $Ar^1$ and $Ar^2$ may include various preferred embodiments. These are selected from the group consisting of a substituted or unsubstituted aromatic ring system containing a 5-membered heterocycle; a substituted or unsubstituted aromatic ring system containing a six-membered heterocycle; a substituted or unsubstituted naphthalene moiety, and a substituted or unsubstituted benzene moiety. There are 16 possible combinations of these embodiments, if $Ar^1$ and $Ar^2$ are considered distinguishable. As will be clear, however, the designation of one aromatic system as $Ar^1$ and the other as $Ar^2$ is arbitrary; thus there are only ten possible combinations. However, for simplicity, $Ar^1$ and $Ar^2$ are designated separately with the realization that the choice is arbitrarily made. All linkers described herein if not palindromic, are considered to link $AR^1$ to $Ar^2$ or vice-versa whether or not the complementary orientation is explicitly shown (as it is in some cases). Thus, if $Ar^1$ and $Ar^2$ are different and a linker is specified as —CONR—, it is understood that also included is the linker —NRCO— when the designations $Ar^1$ and $Ar^2$ are retained.

The noninterfering substituents on the aromatic system represented by $AR^1$ and the noninterfering substituents on the aromatic system represented by $Ar^2$ are represented in the formulas herein by $R^a$ and $R^b$, respectively. Generally, these substituents can be of wide variety. Among substituents that do not interfere with (and in some instances may be desirable for) the beneficial effect of the compounds of the invention on bone in treated subjects are included alkyl (1–6C, preferably lower alkyl 1–4C), including straight or branched-chain forms thereof, alkenyl (1–6C, preferably 1–4C), alkynyl (1–6C, preferably 1–4C), all of which can be straight or branched chains or are aryl (6–10C) or alkylaryl (6–15C) or aryl alkyl (6–15C) and may contain further substituents. $R^a$ and $R^b$ may also include halogens, (e.g. F, Cl, Br and I); siloxy, OR, SR, $NR_2$, OOCR, COOR, NCOR, NCOOR, and benzoyl, $CF_3$, $OCF_3$, $SCF_3$, $N(CF_3)_2$, NO, $NO_2$, CN, SO, $SO_2R$, $SO_3R$ and the like, wherein R is alkyl (1–6C) or is H. Similarly, these substituents may contain R' as a substitute for R wherein R' is aryl (6–10C) or alkylaryl (6–15C) or aryl alkyl (6–15C). Where $R^a$ or $R^b$ substituents are in adjacent positions in the aromatic system, they may combine to form a ring. Further, rings may be included in substituents which contain sufficient carbon and heteroatoms to provide this possibility.

The choice of noninterfering substituents depends on the overall nature of the system. For example, in compounds of the invention wherein two pyridine rings are linked through a saturated flexible linker, a $CF_3$ substituent para to the linker in each of the pyridine rings is particularly preferred. In those systems wherein a quinoline is coupled through a flexible conjugated or nonconjugated linker to a phenyl substituent or to a naphthyl substituent, an amino group para to the linker in the phenyl or naphthyl moiety is preferred. Particularly preferred amino groups are dimethylamino and diethylamino. In systems wherein a benzothiazole is coupled to phenyl through a flexible linker, preferred substituents on the phenyl moiety include alkoxy or alkylthio in combination with halo, in particular, chloro. Also preferred is the presence of a diethylamino group in the phenyl moiety para to the position that is coupled to the linker. In general, the presence of a substituent in the phenyl moiety para to the position of joinder to the linker is preferred.

Generally, preferred noninterfering substituents include hydrocarbyl groups of 1–6C, including saturated and unsaturated, linear or branched hydrocarbyl as well as hydrocarbyl groups containing ring systems; halo groups, alkoxy, hydroxy, amino, monoalkyl- and dialkylamino where the alkyl groups are 1–6C, CN, $CF_3$, $OCF_3$ and COOR, and the like.

Although the number of $R^a$ and $R^b$ may typically be 0–4 (m) or 0–5 (n) depending on the available positions in the aromatic system, preferred embodiments include those wherein the number of $R^a$ is 0, 1 or 2 and of $R^b$ is 0, 1, 2 or 3, particularly 1 or 2.

The linker group, L, may be a covalent bond or any group having a valence of at least two and covering a linear distance of from about 1.5 to about 15 Angstroms, including those that contain cyclic moieties, that meet this spatial requirement. Useful linkers are divided, by definition herein, into three general categories: (1) flexible nonconjugating linkers, (2) flexible conjugating linkers, and (3) constrained linkers. The preferred choice of linker will depend on the choices for $Ar^1$ and $Ar^2$.

As defined herein, flexible nonconjugating linkers are those that link only one position of $Ar^1$ to one position of $Ar^2$, and provide only a single covalent bond or a single chain between $Ar^1$ and $Ar^2$. The chain may contain branches, but may not contain π-bonds (except in the branches) or cyclic portions in the chain. The linker atoms in the chain itself rotate freely around single covalent bonds, and thus the linker has more than two degrees of freedom. Particularly useful flexible nonconjugating linkers, besides a covalent bond, are those of the formulas: —NR—, —$CR_2$—, —S—, or —O—, wherein R is H or alkyl (1–6C), more preferably H or lower alkyl (1–4C) and more preferably H. Also contemplated are those of the formulas: —NRCO—, —CONR—, —$CR_2S$—, —$SCR_2$—, —$OCR_2$—, —$CR_2O$—, —NRNR—, —$CR_2CR_2$—, —$NRSO_2$—, —$SO_2NR$—, —$CR_2CO$—, —$COCR_2$—, and —NR— NR—CO—$CR_2$— and its complement —$CR_2$—CO— NR—NR—, or —$NRCR_2CR_2NR$— or the thiolated counterparts, and particularly —$NHCR_2CR_2NH$—, including the isosteres thereof, such as —NRNRCSNR— and —NRNRCONR—. Also contemplated are those of the formulas: —$NH(CH_2)_2NH$—, —$O(CR_2)_2O$—, and —$S(CR_2)_2S$—, including the isosteres thereof. The optimum choice among flexible nonconjugating linkers is dependent on the nature of $Ar^1$ and $Ar^2$.

Flexible conjugating linkers are those that link only one position of $Ar^1$ to one position of $Ar^2$, but incorporate at least one double or triple bond or one or more cyclic systems in the chain itself and thus have only two degrees of freedom. A flexible conjugating linker may form a completely conjugated π-bond linking system between $Ar^1$ and $Ar^2$, thus providing for co-planarity of $Ar^1$ and $Ar^2$. Examples of useful flexible conjugating linkers include: —RC=CR—; —N=N—; —C≡C—; —RC=N—; —N=CR—; —NR—N=CR—; —NR—NR—CO—CR=CR—, —N=$NCOCR_2$—, —N=$NCSCR_2$, —N=$NCOCR_2CR_2$, —N=NCONR—, —N=NCSNR—, and the like, where R is H or alkyl (1–6C); preferably H or lower alkyl (1–4C); and more preferably H.

Constrained linkers are those that have more than one point of attachment to either or both $AR^1$ and $Ar^2$ and, thus, generally allow for only one degree of freedom. Constrained linkers most frequently form fused 5- or 6-membered cyclic moieties with $Ar^1$ and/or $Ar^2$ where either $Ar^1$ or $Ar^2$ has at least one substituent appropriately positioned to form a second covalent bond with the linker, e.g., where $Ar^2$ is a phenyl group with a reactive, ortho-positioned substituent, or is derivatized to the linker directly at the ortho position. (Although the aromatic moieties should properly be referred to as phenylene or naphthylene in such cases, generally the term "phenyl" or "naphthyl" is used herein to include both monovalent and bivalent forms of these moieties.) Examples of particularly useful constrained linkers include

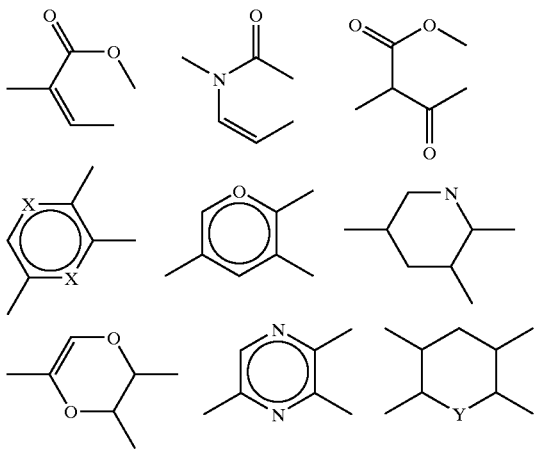

and the like, where X is O, N, S or CR, and Y is $CR_2$ or C=O.

In one class of preferred embodiments, $Ar^1$ is an aromatic system containing a 5-membered heterocycle, of the formula:

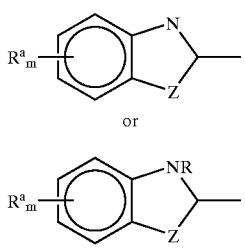

(1a)

or (2a)

wherein Z is S, O, NR or —$CR_2$ in formula (1a) or CR in formula (2a), where each R is independently H or alkyl (1–6C), the dotted line represents an optional π-bond, each $R^a$ is independently a noninterfering substituent as defined above, and m is an integer of 0–4.

In general, $Ar^2$ is phenyl, naphthyl, or an aromatic system containing a 5- or 6-membered heterocyclic ring. All may be unsubstituted or substituted with noninterfering substituents, $R^b$.

When $Ar^2$ is an aromatic system containing a six-membered heterocycle, the formula of said system is preferably:

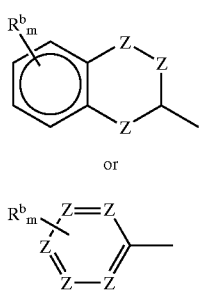

(iii)

or (iv( wherein each Z is independently a heteroatom selected from the group consisting of S, O and N; or is CR or $CR_2$, the dotted lines represent optional π-bonds, each $R^b$ is independently a noninterfering substituent, and m is an integer of 0–4, with the proviso that at least one Z must be a heteroatom.

$Ar^2$ in these compounds may also have the formula

(v)

where $R^b$ is a noninterfering substituent as defined above and n is an integer from 0 to 5.

Similarly, when $Ar^2$ is naphthyl, it may contain 0–5 $R^b$ substitutions. When $Ar^2$ is an aromatic system containing a 5-membered heterocycle, preferred forms are those as described for $AR^1$.

Thus, in one set of preferred compounds, $Ar^1$ is

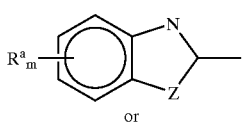

(1a)

or

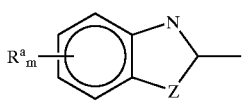

(2a)

wherein each $R^b$ is a noninterfering substituent, m is an integer of 0–4, the dotted line represents an optional πbond, and Z is O, S, NR or $CR_2$ in formula (1) or is CR in formula (2) wherein each R is independently H or alkyl (1–6C).

In one group of these compounds, L is a flexible conjugating or nonconjugating linker. In this group, when Z is NR, $Ar^2$ is preferably a substituted or unsubstituted aromatic system containing a 5-membered heterocycle or is

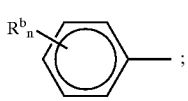

(v)

;

wherein $R^b$ is a noninterfering substituent and n is an integer of 0–5; and/or L is —N=N—, —N=CR—, —RC=CR—, —NRNR—, —$CR_2$NR—, —$CR_2CR_2$—, —NRCO— or —CONR— where R is H or alkyl (1–6C); and/or the dotted line represents a π bond.

In these embodiments as well as in alternative embodiments of $AR^2$, it is preferred that each $R^b$ is independently halo, OR, SR, $NR^2$, NO, $NO_2$, $OCF_3$ or $CF_3$ wherein R is H or alkyl (1–6C), or $R^b$ comprises an aromatic system.

Preferred compounds in this group are 59-0100, 59-103, 59-104, 59-105 and 59-106 (See FIG. 13).

In another group of these compounds with flexible linkers, Z is S, and $Ar^2$ is preferably a substituted or unsubstituted aromatic system containing a 6-membered heterocycle or is of the formula

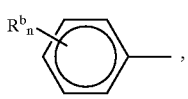

(v)

, wherein $R^b$ is a noninterfering substituent and n is an integer of 0–5; and/or L is —N=N—, —N=CR—, —RC=CR—, —NRNR—, —CR$_2$NR—, —CR$_2$CR$_2$—, —NRCO— or —CONR— where R is H or alkyl (1–6C), and/or the dotted line represents a π bond.

In such compounds, regardless of the choice of AR$^2$, preferred are those compounds wherein each R$^b$ is independently halo, OR, SR, NR$^2$, NO, NO$_2$, OCF$_3$ or CF$_3$ wherein R is H or alkyl (1–6C) or R$^b$ comprises an aromatic system.

Both when Z is S and when Z is NR, it is preferred that m is 0 and/or each R$^b$ is independently OR, SR or halo, where n=2 and at least one R$^b$ is independently OR or SR and/or L is —NHCO— or —CR=CR—.

Preferred compounds in this group include compounds 59-002, 59-0070, 59-0072, 59-0099, 59-0102, the benzothiazole counterpart of 59-0104, 59-0144, 59-0147, 59-0149, 59-0186, 59-0187, 59-0192, 59-0193, 59-0195, 59-0197, 59-0202, 59-0204, 59-0205, 59-0206, 59-0207, 59-0208, and 59-0210, especially the benzothiazole counterpart of 59-0104 or compounds 59-0147, 59-0205 or 59-0210. (See FIG. 13)

Z can also be CR, CR$_2$ or O; here it is also preferred that Ar$^2$ is

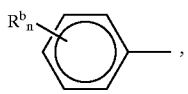

(v)

wherein R$^b$ is a noninterfering substituent and n is an integer of 0–5, and/or L is —N=N—, —N=CR—, —RC=CR—, —NRNR—, —CR$_2$NR—, —CR$_2$CR$_2$—, —NRCO— or —CONR— where R is H or alkyl (1–6C), and/or the dotted line represents a π bond.

In these compounds, too, it is preferred that each R$^b$ is independently halo, OR, SR, NR$_2$, NO, NO$_2$, OCF$_3$ or CF$_3$ wherein R is H or alkyl (1–6C) or R$^b$ comprises an aromatic system. A preferred compound is 896-5005. (See FIG. 4)

The compounds wherein Ar$^1$ is 1a or 2a as above may also contain a constrained linker.

In these compounds, preferred Z is S or NR; and/or those wherein L is selected from the group consisting of

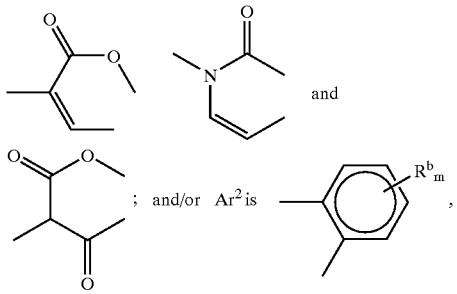

wherein R$^b$ is a noninterfering substituent and m is 0–4.

Preferably, each R$^b$ is independently halo, OR, SR, NR$_2$, NO, NO$_2$, OCF$_3$ or CF$_3$ wherein R is H or alkyl (1–6C) or R$^b$ comprises an aromatic system. A preferred compound is 59-0124. (See FIG. 13)

In another group of preferred embodiments, Ar$^1$ is of the formula

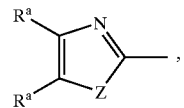

(3a)

wherein each R$^a$ is independently a noninterfering substituent or is H and Z is NR, S or O, wherein R is alkyl (1–6C) or H, especially where Z is S and/or wherein Ar$^2$ is

(v)

wherein R$^b$ is a noninterfering substituent and n is an integer of 0–5; and/or L is —N=N—, —N=CR—, —RC=CR—, —NRNR—, —CR$_2$NR—, —CR$_2$CR$_2$—, —NRCO— or —CONR— where R is H or alkyl (1–6C), and/or the dotted line represents a π bond. Especially preferred are those compounds where each R$^b$ is independently halo, OR, SR, NR$_2$, NO, NO$_2$, OCF$_3$ or CF$_3$ wherein R is H or alkyl (1–6C) or R$^b$ comprises an aromatic system.

In another group of compounds, Ar$^1$ is

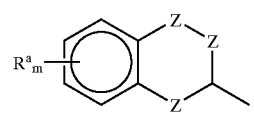

(4a)

wherein R$^a$ is a noninterfering substituent, m is an integer of 0–4, each dotted line represents an optional π-bond, each Z is independently N, NR, CR or CR$_2$, where each R is independently H or alkyl (1–6C) with the proviso that at least one Z is N or NR.

Particularly preferred members of this group are those wherein AR$^1$ is

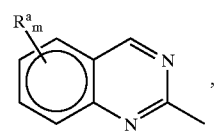

(5a)

especially those wherein Ar$^2$ is

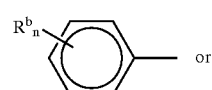

(v)

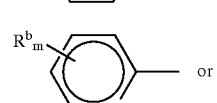

(vi)

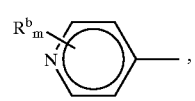

(via)

wherein each R$^b$ is independently a noninterfering substituent, and n is 0–5 and m is 0–4, and/or L is —N=N—, —RC=CR—, —RC=N—, —NRCO—, —NRCR$_2$—, —NRCR$_2$CR$_2$—, —NRCR$_2$CO—, —NRNR—, —CR$_2$CR$_2$—, —NRCR$_2$CR$_2$NR—, —NRCR=CRNR— or —NRCOCR$_2$NR—.

In general, preferably each R$^b$ is independently halo, OR, SR, NR$_2$, NO, NO$_2$, OCF$_3$ or CF$_3$ wherein R is H or alkyl (1–6C) or R$^b$ comprises an aromatic system.

In an especially preferred group, m is 0, each R$^b$ is NR$_2$ or OR and n is 1 or 2, and/or L is —CR=CR—, —N=N— or —NRCO—, especially the compounds of formulas 59-0030, 59-0078, 59-0091, 59-0093, 59-0150, 50-0197, 59-0198, 59-0199 or 59-0480. (See FIG. 13)

Also preferred are those wherein Ar$^1$ has formula (4a) or (5a) and wherein Ar$^2$ is substituted or unsubstituted quinolyl or naphthyl of the formula

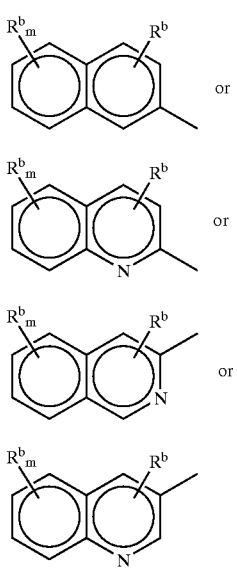

(vii)

(viii)

(ix)

(x)

wherein each R$^b$ is a noninterfering substituent and m is 0–4.

Preferred among these are those wherein L is —N=N—, —RC=CR—, —RC=N—, —NRCO—, —NRCR$_2$—, —NRCR$_2$CR$_2$—, —NRCR$_2$CO—, —NRNR—, —CR$_2$CR$_2$—, —NRCR$_2$CR$_2$NR—, —NRCR=CRNR— or —NRCOCR$_2$NR—, and/or wherein each R$^b$ is independently halo, OR, SR, NR$_2$, NO, NO$_2$, OCF$_3$ or CF$_3$ wherein R is H or alkyl (1–6C) or R$^b$ comprises an aromatic system and m is 0, 1 or 2.

The compounds 59-0089, 59-0090, 59-0092 or 59-0094 are particularly preferred.

Ar$^1$ is also preferably

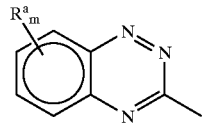

(6a)

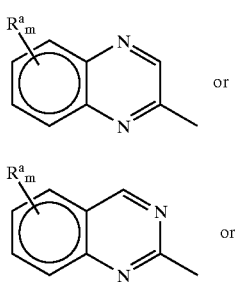

(7a)

-continued

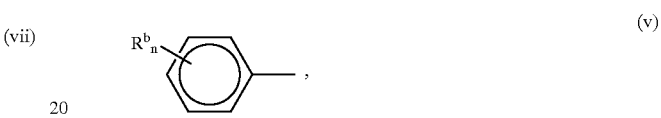

(8a)

wherein each R$^a$ is a noninterfering substituent and m is 0–4, in particular where L is —N=N—, —RC=CR—, —RC=N—, —NRCO—, —NRCR$_2$—, —NRCR$_2$CR$_2$—, —NRCR$_2$CO—, —NRNR—, —CR$_2$CR$_2$—, —NRCR$_2$CR$_2$NR—, —NRCR=CRNR— or —NRCOCR$_2$NR—, and/or Ar$^2$ is

(v)

wherein R$^b$ is a noninterfering substituent and n is an integer of 0–5. Especially preferred are compounds wherein each R$^b$ is independently halo, OR, SR, NR$_2$, NO, NO$_2$, OCF$_3$ or CF$_3$ wherein R is H or alkyl (1–6C) or R$^b$ comprises an aromatic system, in particular compounds 59-203, 59-285 or 59-286. (See FIG. 13)

When Ar$^1$ is of formula (4a), L can also be a constrained linker.

In still another preferred set, Ar$^1$ is

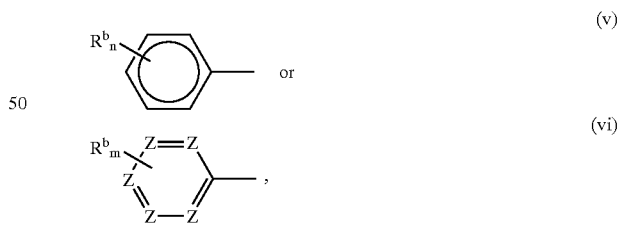

(9a)

wherein each R$^a$ is independently a noninterfering substituent, m is an integer of 0–4, each Z is independently N or CR, where R is H or alkyl (1–6C), with the proviso that at least one Z must be N and at least one Z must be CR.

In these compounds, L is preferably a flexible conjugating or nonconjugating linker, and/or wherein Ar$^2$ is (v)

or (vi)

wherein each R$^b$ is independently a noninterfering substituent, and in (vi) each Z is independently N or CR, where R is H or alkyl (1–6C), with the proviso that at least one Z must be a N and at least one Z must be CR.

Preferred such compounds have the formula

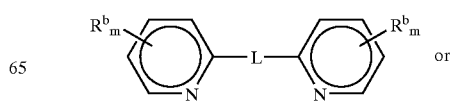

or

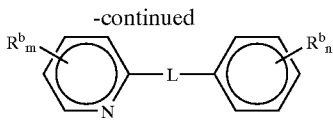

Preferred L embodiments in this group include —N=N—, —RC=CR—, —RC=N—, —NRCO—, —NRCR₂—, —NRCR₂CR₂—, —NRCR₂CO—, —NRNR—, —CR₂CR₂—, —NRCR₂CR₂NR—, —NRCR=CRNR— or —NRCOCR₂NR—; preferred for $R^a$ and $R^b$ are halo, OR, SR, NR₂, NO, NO₂, OCF₃ or CF₃ wherein R is H or alkyl (1–6C) or $R^a$ or $R^b$ comprise aromatic systems and each m and n is independently 0, 1 or 2.

In particular, compounds are preferred where L is —NHCR₂CR₂NH— and $R^a$ is CF₃ para to L, especially compounds 59-0145, 59-0450, 59-0459 or 59-0483. (See FIG. 13)

Finally, in another preferred group, Ar¹ is

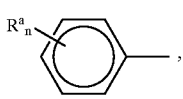

(10a)

wherein each $R^a$ is a noninterfering substituent, and n is an integer of 0 and 5, and wherein L is a flexible linker that contains at least one nitrogen. In the alternative or in addition, Ar² is of the formula

(v)

and L is —N=N—, —RC=CR—, —RC=N—, —NRCO—, —NRCR₂—, —NRCR₂CR₂—, —NRCR₂CO—, —NRNRCR₂CR₂—, —NRNRCR=CR—, —NRNRCOCR₂—, —NRNRCOCR=CR—, —NRNRCSCR₂—, —NRNRCSCR=CR—, —NRNRCONR—, —NRNRCSNR—, —NRNR—, —CR₂CR₂—, —NRCR₂CR₂NR—, —NRCR=CRNR— or —NRCOCR₂NR—. It is preferred that each $R^b$ is independently halo, OR, SR, NR₂, NO, NO₂, OCF₃ or CF₃ wherein R is H or alkyl (1–6C) or $R^b$ comprises an aromatic system.

Especially preferred are those compounds wherein L is —CR=CRCONRNR—, —CR=CRCSNRNR—, —CR₂CONRNR——CR₂CSNRNR—, —NRNRCONR— or —NRNRCSNR— and/or $R^b$ is —NR2 and n=1 wherein $R^b$ is in the para position, especially wherein $R^a$ is —COOR and m is 1; most especially compounds 59-0045, 59-0095, 59-0096, 59-0097 and 59-0098. (See FIG. 13)

Figure 5A:
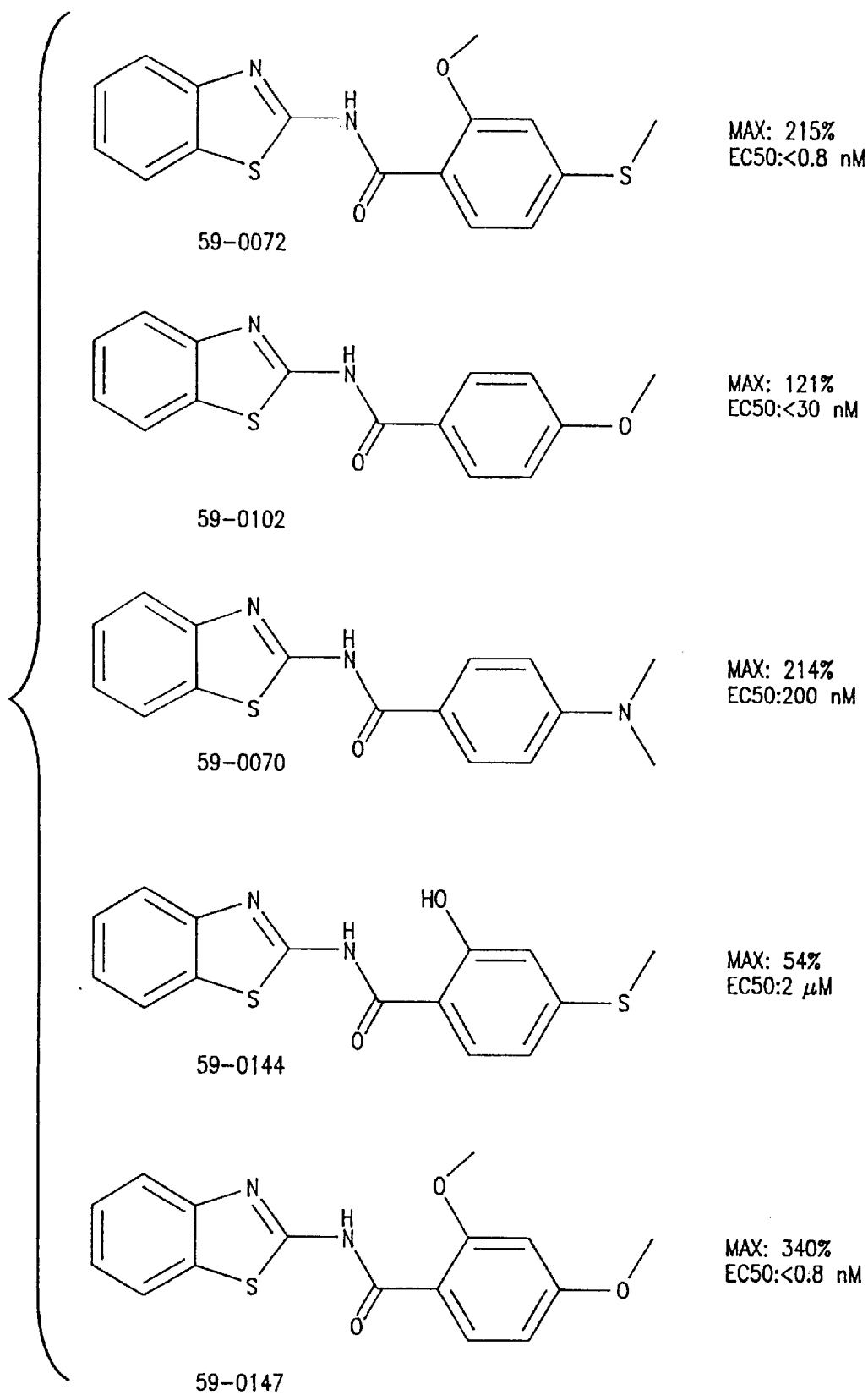
FIGS. 5A, 5B and 5C show structures and results of a screening assay for a group of compounds which varies the parameters of lead compound 59-0072.
Figure 5B:
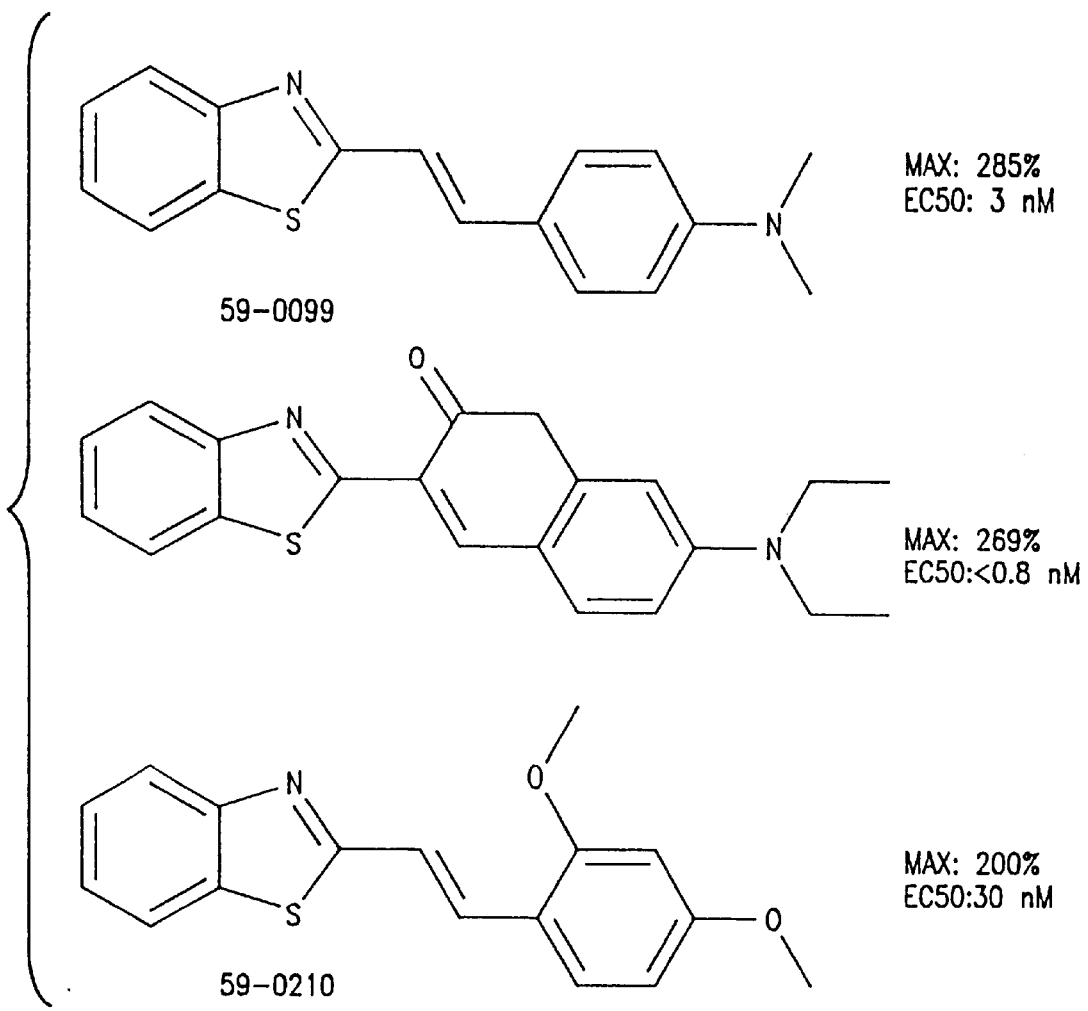
Figure 5C:
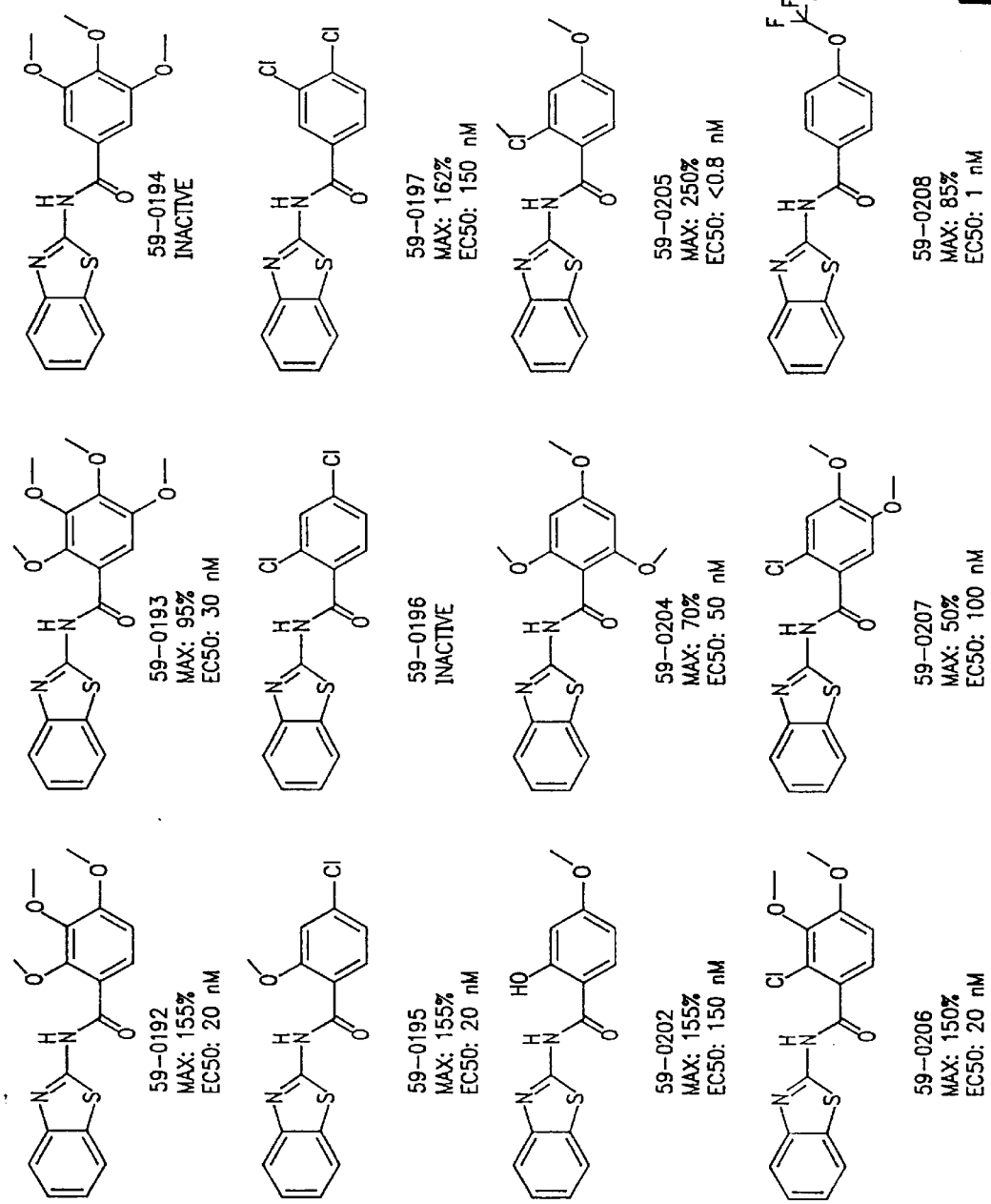

As set forth above, several families of preferred embodiments are defined by specifying Ar¹ and AR², and L. In one such family, wherein Ar¹ is an aromatic system containing a 5-membered heterocyclic ring, the compound 59-0072, wherein Ar¹ is unsubstituted benzothiazole, the linker (Ar¹→Ar²) is NHCO, and Ar² is 2-methoxy-4-methylthiophenyl was used as a lead compound and variations of the structure studied. FIG. 5 shows representative compounds synthesized to analyze the effects of the nature of the linker, various alternatives of Ar¹ wherein Z is O, NR or S, and the effect of substitution on the phenyl moiety, as well as the heterocycle.

FIG. 5 gives the structures of these compounds, along with their maximum activity as compared to 59-0008 at 10 μM (the maximum for 59-0008) in the in vitro bone growth stimulation assay as well as the concentration at which 50% of maximum stimulation of the BMP promoter was obtained (EC₅₀). See Example 1 for the details of this assay. The results of this study indicate that the amide linker in 59-0072 can readily be substituted by —CH=CH— and that the substitution on the phenyl ring had advantageous effects in the order: 2-Cl-4-OMe=2,4-di-OMe=2-OMe-4-SMe>>3,4-di-OMe=4-OMe. In general, compounds 59-0205, 59-0104, 59-0107, 59-0210 and 59-0124 have the best activity in the primary screen, but only 59-0124 is active in the ex vivo calvarial assay described in Example 3.

Figure 6A:
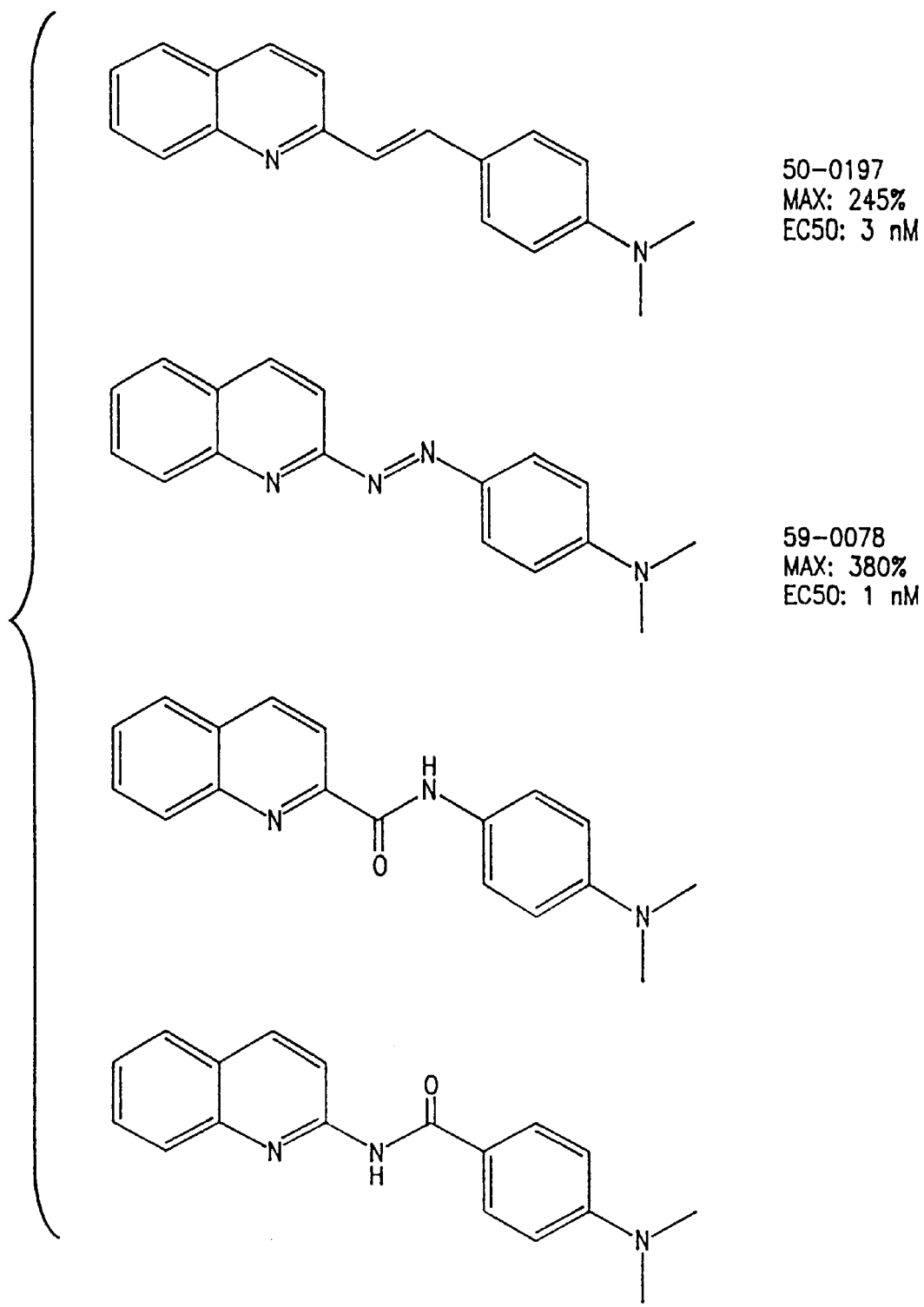
Figure 6B:
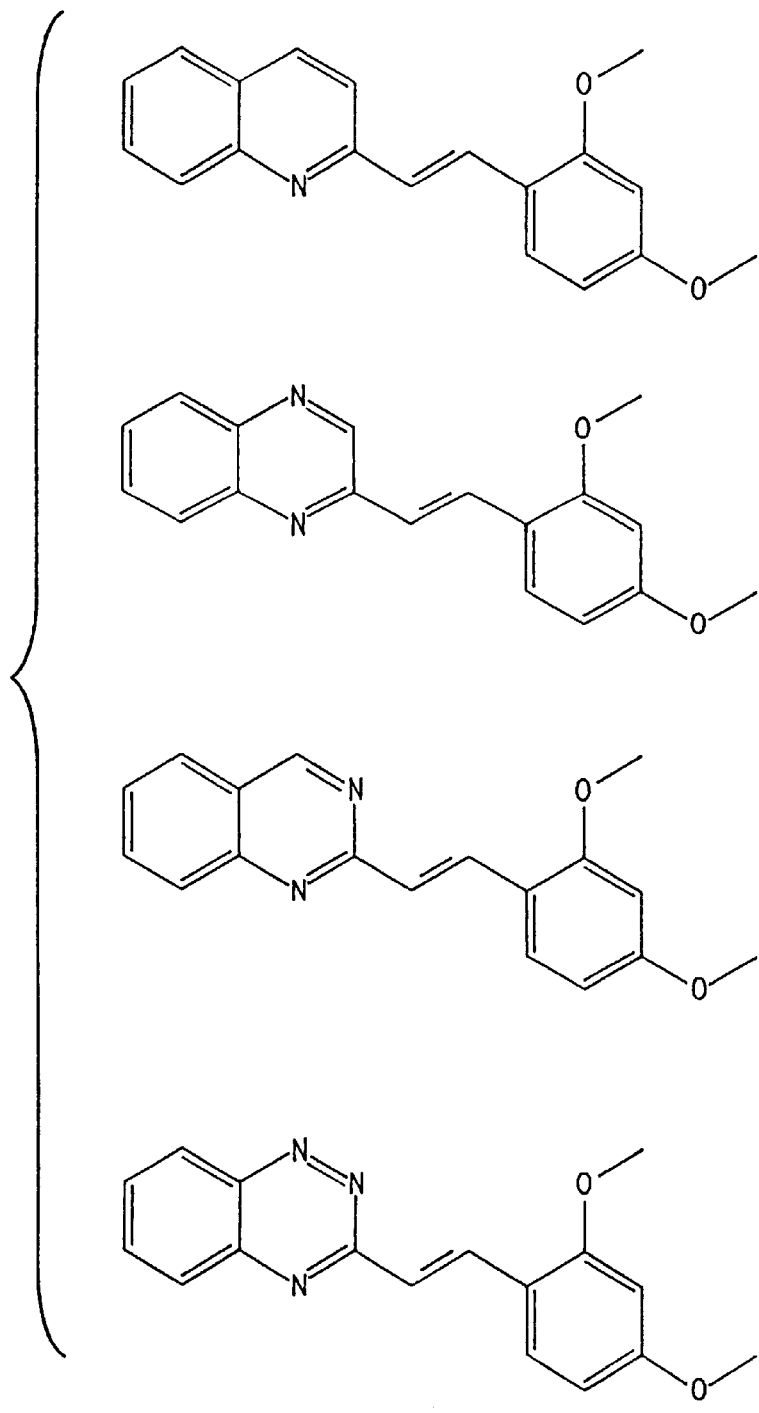

Similar structure/activity relationship studies were conducted for compounds wherein Ar¹ is quinoline. In this study, compound 50-0197, wherein Ar¹ is unsubstituted quinoline, the linker is —CH=CH—, and Ar² is p-dimethylaminophenyl was used as a lead compound. The compounds synthesized in this study are shown in FIG. 6, along with their maximum stimulation characteristics and EC₅₀ in the assay of Example 1. The results of these studies showed that quinoxaline analogs are the most active in the assay, followed by quinoline; the linker can most preferably be —CH=CH— or —N=N— as judged by activity in the assay, but —CH=CH— is preferred in vivo due to its lack of toxicity. Preferred substituents on the phenyl ring in Ar² include 2,4—di—OMe; 4-NMe₂-2-OMe, and 4-NMe₂. For the compounds in FIG. 6, 59-0282 and 50-0197 were moderately active and 59-0203 was highly active in the ex vivo calvarial assay described hereinabove as a modification of Gowen, M. and Mundy, G. *J Immunol* (1986) 136:2478–2482.

Another group of compounds wherein Ar¹ and Ar² are pyridyl heterocycles was also studied. In this case, compound 59-0145 was used as the lead compound; the linker, the nature of the substituents $R^a$ and $R^b$ were varied. In one instance, a quinolyl residue was substituted for a pyrimidine residue as Ar². Representative compounds used in this study are shown in FIG. 7, along with the data from the screening assay.

Using 59-0145 as a lead, a CF₃ group in one of Ar¹ and Ar² appeared essential; however, one of $R^a$ or $R^b$ could also be NO₂ or CN. The most preferred linker is —NHCH₂CH₂NH—; substitution on the amino groups in L by an alkyl group appeared to reduce activity. Enhanced chain lengths also led to loss of activity.

Preferred compounds in this group, which perform better than 59-0008 in the screening assay, included 59-0450, 59-0459, 59-0480, and 59-0483.

Figure 8A:
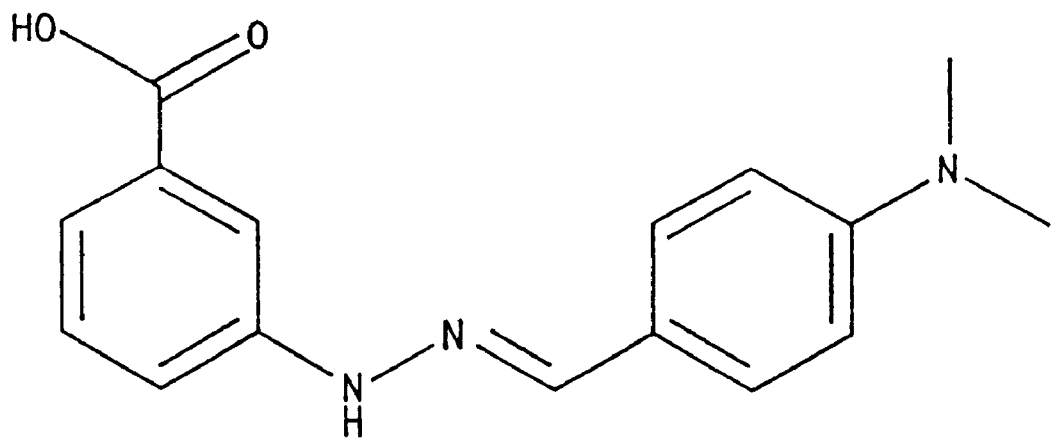
FIGS. 8A, 8B and 8C show structures and results of a screening assay for a group of compounds which varies the parameters of lead compound 59-0045.
Figure 8B:
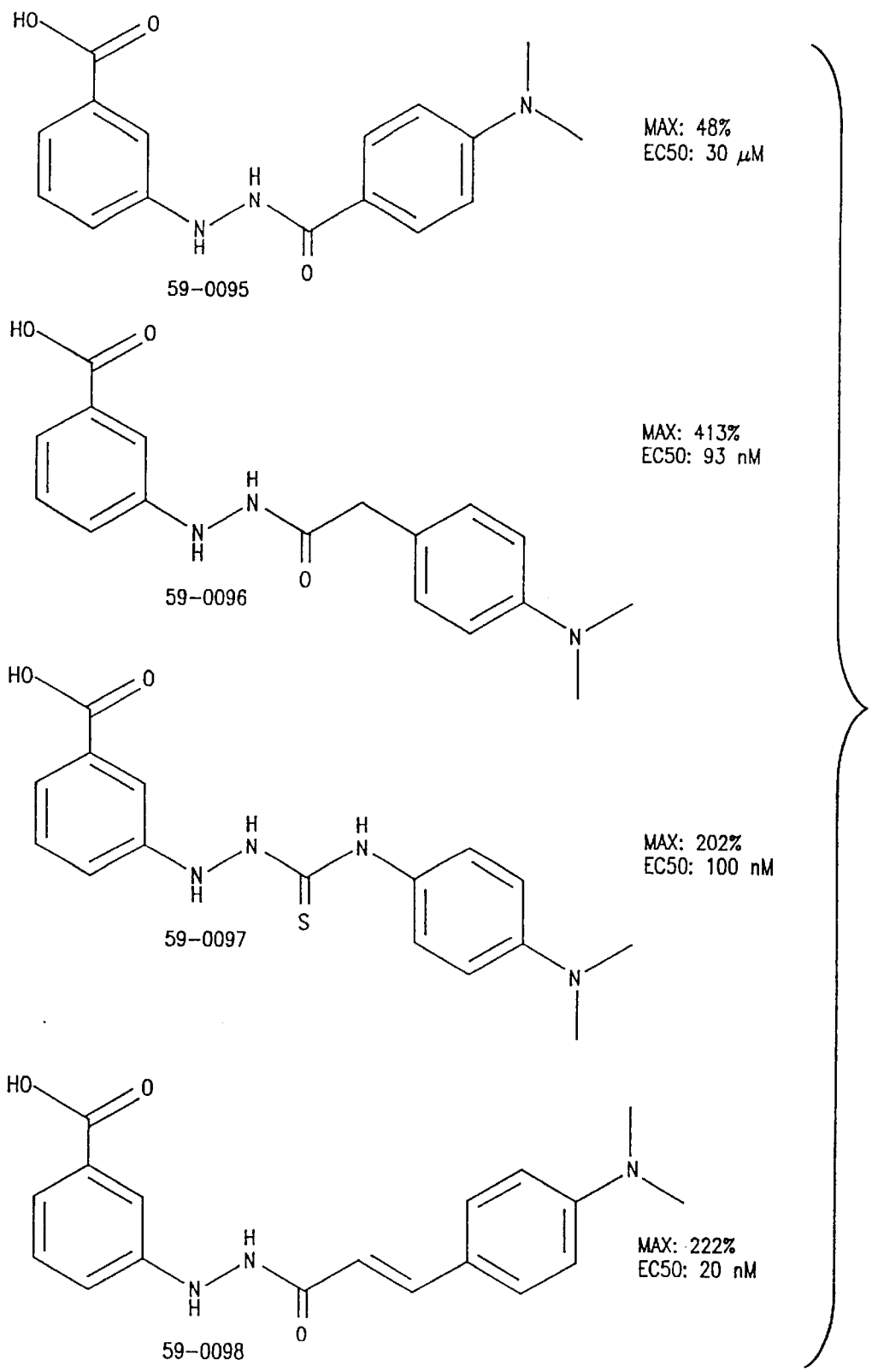
Figure 8C:
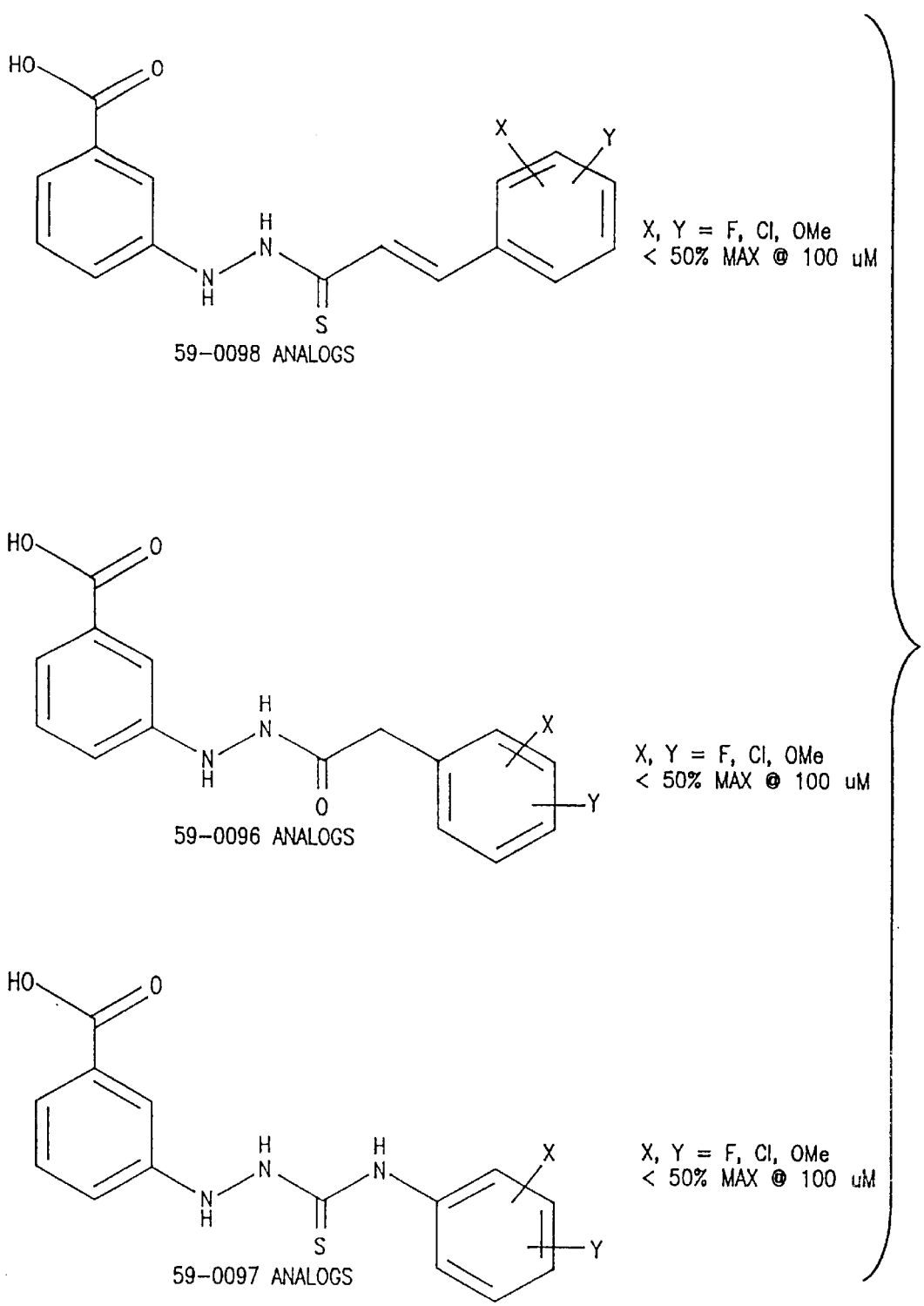

Finally, a series in which Ar¹ is 3-carboxyphenyl was studied using 59-0045 as the lead compound. In 59-0045, L is —NHN=CH— and Ar² is p-dimethylaminophenyl. FIG. 8 shows the compounds synthesized in this series. Under the circumstances of this assay, analogs wherein $R^b$ was, instead of a nitrogen-containing moiety, F, Cl, or OMe were inactive. Preferred compounds in this series are 59-0096 and 59-0098. 59-0098 is very active in the ex vivo calvarial assay described above.

Synthesis of the Compounds Useful in the Invention

Many of the compounds useful in the invention are commercially available and can be synthesized by art-known methods. Those compounds useful in the invention which are new compounds, can similarly be obtained by methods generally known in the art, as described in the Examples below.

The following examples are intended to illustrate, but not to limit, the invention.

PREPARATION A

Compound 59-0008 used as a standard in the assays, was synthesized according to the procedure of McDonald, W. S., et al. *Chem Comm* (1969) 392–393; Irving, H. N. N. H. et al. *Anal Chim Acta* (1970) 49:261–266. Briefly, 10.0 g of dithizone was taken up in 100 ml EtOH and 50 ml AcOH and heated at reflux for 18 h. After cooling, this was diluted first with 100 ml water and then with 50 ml 1N NaOH. This was then further neutralized by the addition of 6 N NaOH to bring the pH to 5.0. This deep purple mixture was then concentrated on a rotavapor to remove organics. Once the liquid had lost all of its purple color, this was filtered to collect the dark precipitate. Purification by flash chromatography (4.5×25.7 cm; EtAc/Hep. (1:4); $R_f$ 0.22) followed by recrystalization from EtOH gave 2.15 g (25% yield) of dark purple crystals, mp=184–185° C. $^1$H NMR (CDCl$_3$) 7.90 (d of d, $J_1$=7.7, $J_2$=2.2, 2H), 7.64 (hump, 1H), 7.49 (m, 3H), 7.02 (m, 1H), 6.91 (m, 2H), 6.55 (d, J=8.1, 1H). MS (EI) 254 (47, M+), 105 (26), 77 [100], 51 (27). HRMS (EI, M+) 254.0626 (calcd 254.0626182). Anal. Calcd For $C_{13}H_{10}N_4S$: C, 61.40; H, 3.96; N, 22.03. Found: C, 61.40; H, 4.20; N, 22.06.

Example 1

High Throughput Screening

Several tens of thousands of compounds were tested in the assay system set forth in WO 96/38590, published Dec. 5, 1996, and incorporated herein by reference. The standard positive control was 59-0008 (also denoted "OS8"), which is of the formula:

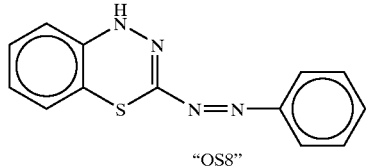

"OS8"

In more detail, the 2T3-BMP-2-LUC cells, a stably transformed osteoblast cell line described in Ghosh-Choudhury et al. *Endocrinology* (1996) 137:331–39, referenced above, was employed. The cells were cultured using α-MEM, 10% FCS with 1% penicillin/streptomycin and 1% glutamine ("plating medium"), and were split 1:5 once per week. For the assay, the cells were resuspended in a plating medium containing 4% FCS, plated in microtiter plates at a concentration of $5 \times 10^3$ cells (in 50 μl)/well, and incubated for 24 hours at 37° C. in 5% $CO_2$. To initiate the assay, 50 μl of the test compound or the control in DMSO was added at 2× concentration to each well, so that the final volume was 100 μl. The final serum concentration was 2% FCS, and the final DMSO concentration was 1%. Compound 59-0008 (10 μM) was used as a positive control.

The treated cells were incubated for 24 hours at 37° C. and 5% $CO_2$. The medium was then removed, and the cells were rinsed three times with PBS. After removal of excess PBS, 25 μl of 1× cell culture lysing reagent (Promega #E153A) was added to each well and incubated for at least ten minutes. Optionally, the plates/samples could be frozen at this point. To each well was added 50 μl of luciferase substrate (Promega #E152A; 10 ml Promega luciferase assay buffer per 7 mg Promega luciferase assay substrate). Luminescence was measured on an automated 96-well luminometer, and was expressed as either picograms of luciferase activity per well or as picograms of luciferase activity per microgram of protein.

In this assay, compound 59-0008 (3-phenylazo-1H-4,1,2-benzothiadiazine) exhibited a pattern of reactivity, as shown in FIG. 2. The activity for compound 59-0008 was maximal at a concentration of approximately 3–10 μM and, more particularly, at about 3 μM, and thus provided a response of approximately 175 light emission units. Accordingly, other tested compounds were evaluated at various concentrations, and these results were compared to the results obtained for 59-0008 at 10 μM (which value was normalized to 100). For instance, any tested compound in FIG. 3 and FIG. 4 that showed greater activity than 10 μM of 59-0008 would result in a value over 100.

As shown in FIG. 3 (46 sheets) and FIG. 4 (28 sheets), several compounds were found to be particularly effective.

Example 2

In vivo Calvarial Bone Growth Data

Compound 59-0008 was assayed in vivo according to the procedure described previously (see "In vivo Assay of Effects of Compounds on Murine Calvarial Bone Growth", sitpra). As compared to a vehicle control, compound 59-0008 induced a 4-fold increase in width of new calvarial bone.

In another experiment, 5 week old Swiss white mice were injected 3 times a day for 5 days over the calvaria with compound 59-0203 using PBS, 5% DMSO and 0.1% BSA as carrier. The drug was tested at 6 different doses, from 0.1–50 mg/kg/day. Animals were sacrificed 3 weeks after the injections started and calvariae were fixed, decalcified, and processed for histology. Bone histomorphometry measuring total bone area (BA/TV) confirms that FGF, used in every experiment as a positive control, shows an increase in the total bone area with all doses tested, but this increase is only significantly different from control at 1 and 5 mg/kg/day. The invention compound 59-0203 shows consistent increases over the 0.1–50 mg/kg/day range at a somewhat lower level than that obtained with FGF.

Similar results are obtained when new bone width in microns is measured. There was no new bone present in the control group. 59-0203 caused new bone formation at all doses, with a significant increase at 25–50 mg/kg/day. New bone as percentage of the total bone area was about 45% for the FGF positive control and from about 15% to 30% over the range of 0.1–50 mg/kg/day for 59-0203. There was no new bone present in the negative control.

Example 3

Ex vivo Calvarial Bone Growth Assay

A number of compounds, in particular, those studied in connection with lead compounds classified as hydrazone/hydrazides (H) exemplified by 59-0045, benzothiazoles (T) exemplified by 59-0104, bis-pyridines (P) exemplified by 59-0145, and quinolines/quinoxalines (Q) exemplified by 59-0197, were tested in the ex vivo calvarial assay described hereinabove. The results of this assay are shown in FIG. 9. In this assay, histomorphotometry and osteoblast numbers are measured and effects are measured on an arbitrary scale from 1–3: i.e., 1, 1+, 2−, 2, 2+, 3−, 3, wherein 1 denotes "inactive." In this assay, for example, FGF scores 2–3.

The scores are assigned to bone formation on the ectocranial periosteal surface. The area immediately surrounding midline suture is excluded from analysis.

| Score | |
|---|---|
| 0 | Toxicity. Cell necrosis, pyknotic nuclei, matrix disintegration. |
| 1 | A score of "1" is the bone forming activity seen in control cultures containing BGJb media +0.1% bovine serum albumin. The periosteal surface is covered by one layer of osteoblasts (at about 50% of the bone surface, with the remaining 50% being covered by bone lining cells). A score of "1–" is assigned if less than 50% of the periosteal surface is covered by osteoblasts due to inhibitory activity or minor toxicity of the agents being tested. A score of "1+" is given if over 50% of the surface is covered by osteoblasts. |
| 2 | A moderate increase in bone forming activity. 20–40% of the periosteal surface is covered by up to two layers of osteoblasts. A score of "2–" is given if less than 20% of the surface is covered by two layers and "2+" if more than 40% of the surface is covered by two layers of osteoblasts. |
| 3 | A score of "3" is the bone forming activity seen in control cultures containing BGJb media +0.1% BSA +10% fetal bovine serum. More than 20% of the periosteal surface is covered by three layers of osteoblasts. The cells appear plump (size can exceed 100 $\mu m2$). A score of "3–" is given if less than 20% of the periosteal surface is covered by three layers of osteoblasts and or osteoblast size is less than 100 $\mu m2$. A score of "3+" has never been observed. |

In all samples, toxicity, ectopic new or woven bone formation associated with osteoblasts, and osteoblast size as reflections of relative activity are noted.

The results shown in FIG. 9 represent those obtained when the measurements were made by two different groups. It is clear that a number of compounds tested have activity in this assay. From the results shown in FIG. 9, 59-0073, 59-0030, 59-0070, 59-007, 59-0019, 59-0099, 59-0072 and 59-0103 show at least some indication of activity. 59-150 and 59-0104 showed activity when measured by one group but not the other; similarly, 50-0197 had this pattern. It appears that 59-0098 and 59-0203 are quite active in this assay and 59-0145 shows a consistent moderate activity.

Example 4

Stimulation of Bone Growth in Ovariectomized Rats (OVX Assay)

The compound 59-0145 was tested at various concentrations in the OVX assay conducted as described above. The increase in bone volume was measured by two different groups; one group found 5 $\mu g/kg/day$ of 59-0145 gave 21% increase over control whereas the second group found a 71% increase. At 50 $\mu g/kg/day$, the first group found a 31% increase, and the second a 54% increase.

Figure 10:
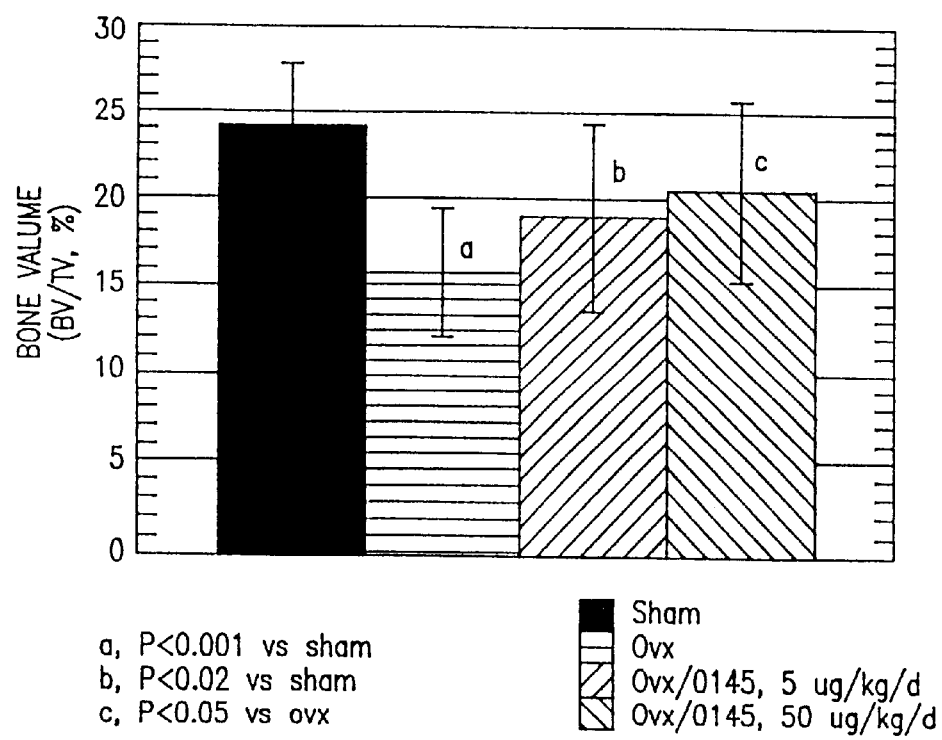
FIG. 10 shows the increase in bone volume effected by subcutaneous administration of compound 59-0145 in the OVX in vivo assay.

In another experiment, the lumbar vertebrae were measured and the above dosages of 59-0145 were shown to provide a beneficial effect, as shown in FIG. 10.

In another experiment, 3 month old Sprague Dawley rats were ovariectomized and depleted for six weeks. At the end of the six weeks, treatment was started with subcutaneous administration of compound 59-0145. The treatment continued for 10 weeks. At the end of the 10 weeks animals were sacrificed, bones were collected for qCT measurements and histology; serum was also collected for osteocalcin determinations.

Figure 11:
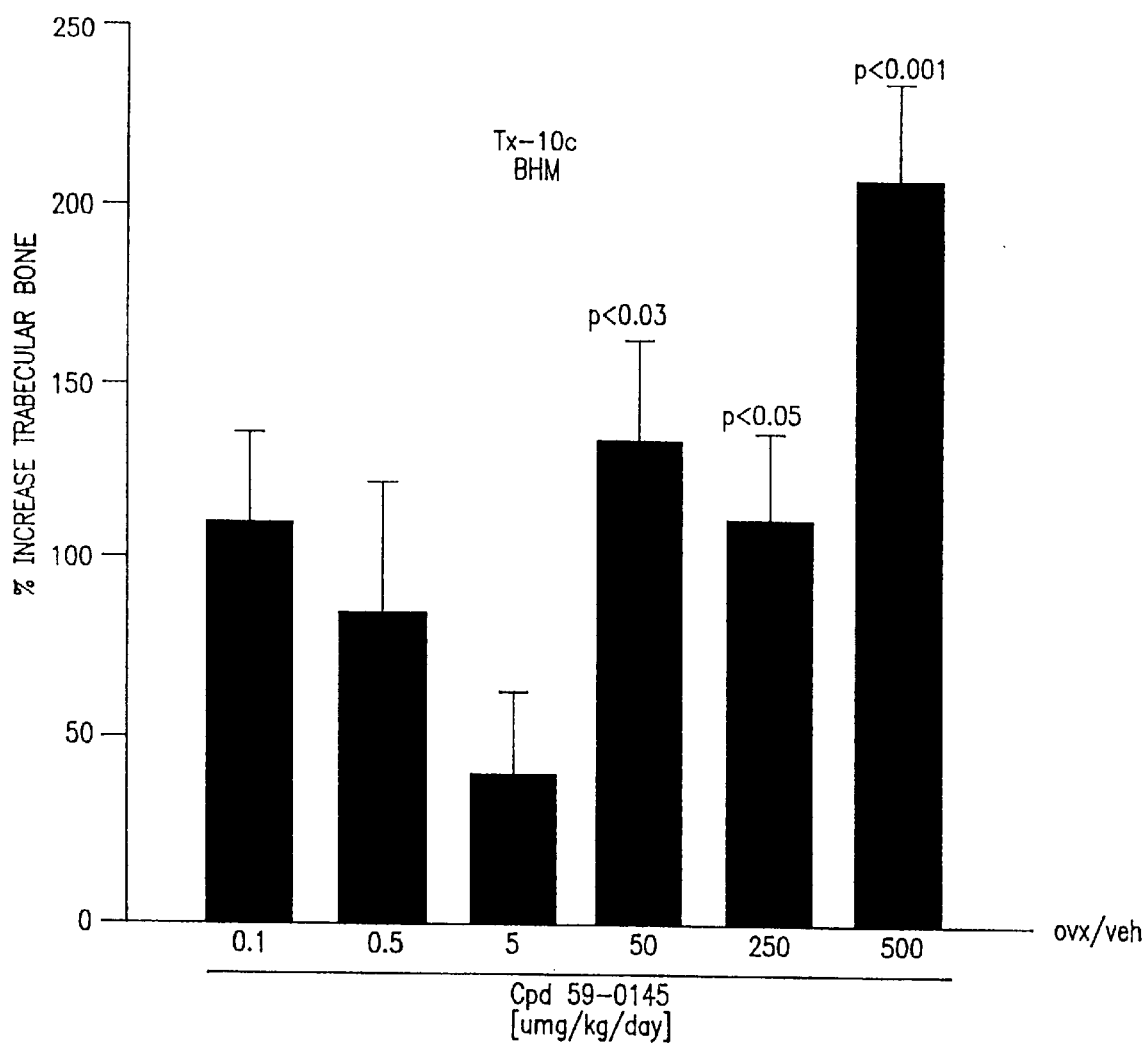
FIG. 11 is a graphical representation of percent increase in trabecular bone in ovariectomized rats treated with compound 59-0145.

FIG. 11 shows the percentage increase in trabecular bone (proximal tibia) compared to the placebo-treated group in chronic ovariectomized rats after 10 weeks of treatment. Compound 59-0145 causes significant increase in trabecular bone at doses of 50–500 $\mu g/kg/day$.

Figure 12:
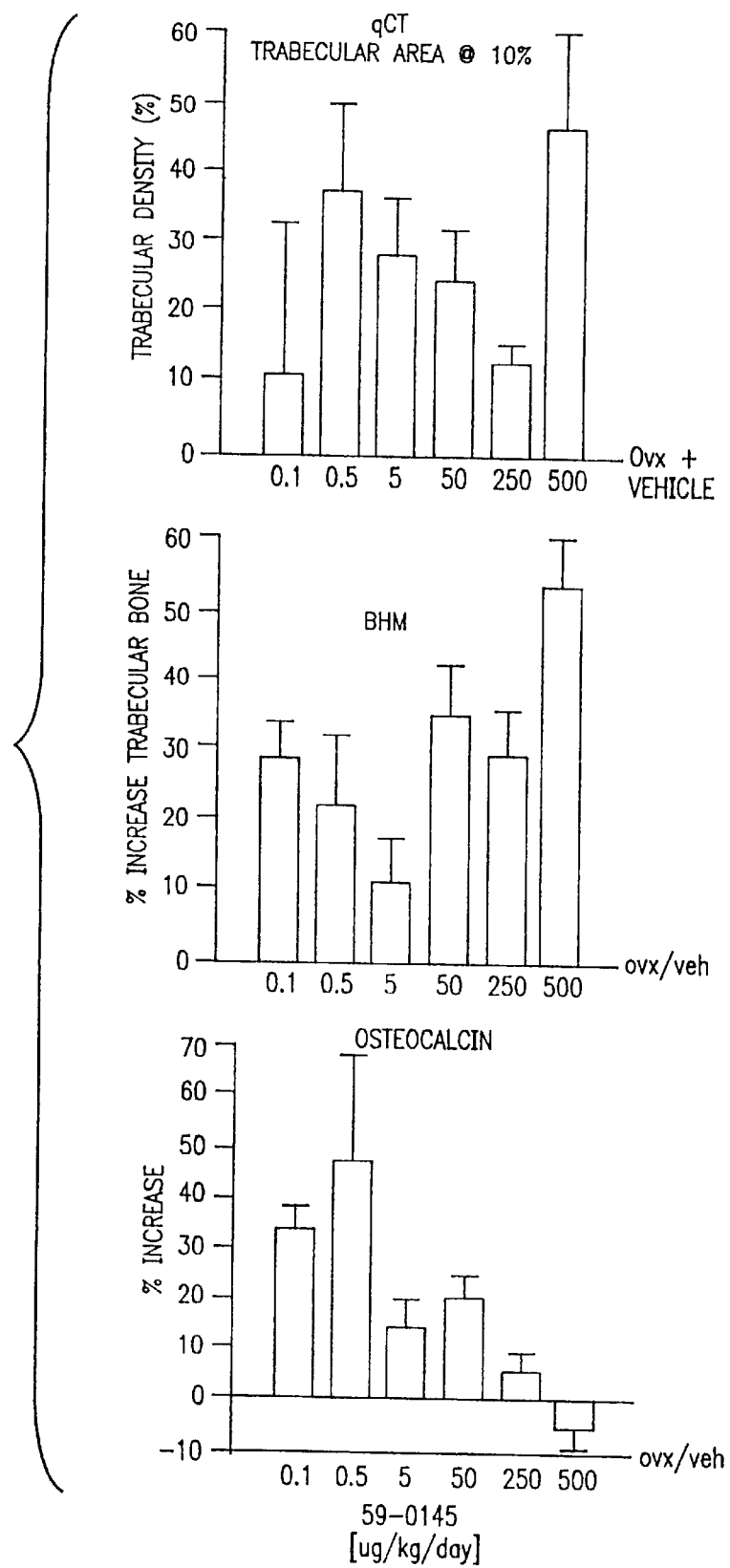
FIG. 12 presents graphs showing results of qCT and bone histomorphometri and serum osteocalcin levels in rats treated with compound 59-0145.
Figure 130:
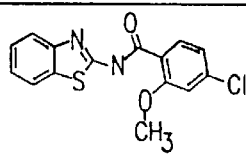
Figure 2:
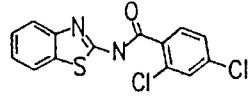

FIG. 12 shows results of qCT and bone histomorphometry in proximal tibia in the first two panels, as well as serum osteocalcin levels at the time of sacrifice as a percentage increase compared to control group (OVX placebo-treated group).

Example 5

Chondrogenic Activity

Compounds 59-008, 59-0102 and 50-0197 were assayed for effects on the differentiation of cartilage cells, as compared to the action of recombinant human BMP-2. Briefly, a mouse clonal chondrogenic cell line, TMC-23, was isolated and cloned from costal cartilage of transgenic mice containing the BMP-2 gene control region driving SV-40 large T-antigen, generated as described in Ghosh-Choudhury et al *Endocrinology* 137:331–39, 1996. These cells were cultured in DMEM/10% FCS, and were shown to express T-antigen, and also to produce aggrecan (toluidine blue staining at pH 1.0) and Type-II collagen (immunostaining) by 7 days after confluence.

For measurement of alkaline phosphatase (ALP) activity, the technique of LF Bonewald et al. *J. Biol Chem* (1992) 267:8943–49, was employed. Briefly, TMC-23 cells were plated in 96 well microtiter plates in DMEM containing 10% FCS at $4 \times 10^3$ cells/well. Two days after plating, the cells were confluent and the medium was replaced with fresh medium containing 10% FCS and different concentrations of compounds or recombinant BMP-2. After an additional 2 or 5 days incubation, the plates were washed twice with PBS, and then lysing solution (0.05% Triton X-100) was added (100 $\mu l$/well). The cells were lysed by three freeze-thaw cycles of $-70°$ C. (30 min), followed by 37° C. (30 min with shaking). Twenty microliters of cell lysates were assayed with 80 $\mu l$ of 5 mM p-nitrophenol phosphate in 1.5 M 2-amino-2-methyl-propanol buffer, pH 10.3 (Sigma ALP kit, Sigma Chemical Co., St. Louis, Mo.) for 10 min at 37° C. The reaction was stopped by the addition of 100 $\mu l$ of 0.5 M NaOH. The spectrophotometric absorbance at 405 nm was compared to that of p-nitrophenol standards to estimate ALP activity in the samples. The protein content of the cell lysates was determined by the Bio-Rad protein assay kit (Bio-Rad, Hercules, Calif.). Specific activity was calculated using these two parameters.

At day 2, compounds 59-0008 ($10^{-9}$ M), 59-0102 ($10^{-7}$ M) and 59-0197 ($10^{-9}$ M) increased ALP levels approximately 3-, 2- and 2.5-fold, respectively, as compared to the vehicle control. Recombinant BMP2 at 100, 50 or 10 ng/ml-induced ALP levels approximately 10-, 4- or 1.5-fold, respectively, as compared to the vehicle control.

Example 6

Synthesis of Exemplary Compounds

A. Compounds of the invention wherein $AR^1$ is of formula (1a) or (2a) can be synthesized by the procedures described in Dryanska, V. and Ivanov, K. *Synthesis* (1976) 1:37–8, using the described embodiments of $Ar^2$ and the appropriate analogous heterocycle embodied in $Ar^1$ substituted for the benzothiazole shown. Alternates to the olefin linker described can also be prepared using standard methods.

Compounds of the invention represented by exemplary Compound 59-0234, wherein Z is O, L is —CH=CH—, and $Ar^2$ is 2,4-dimethyoxy-phenyl, including Compounds 59-0211 and 59-0233, were prepared according to the following procedure describing synthesis of Compound 59-0234. Briefly, to a N,N-dimethylformamide (DMF) solution of 2-methylbenzoxazole (1 mmol) and 2,4-dimethoxybenzaldehyde (1 mmol) was added lithium t-butoxide (2 mmol). The reaction mixture was heated at 130° C. for 3 h. After cooling to room temperature, the reaction mix was poured into ether and washed several times with water. The organic phase was dried over $Na_2SO_4$, filtered. and evaporated to dryness. The residue was dissolved in a minimal amount of hot ether and, on standing overnight, the crystalline product was collected by filtration.

B. Exemplary Compound 59-0150 where $Ar^1$ is of formula 4a was synthesized according to the procedure of Zamboni et al. *J Med Chem* (1992) 35:3832–44. First, 2-triphenylphosphoniumquinaldine bromide was synthesized as follows. Quinaldine (200 mmols), NBS (200 mmols) and a catalytic amount of benzoyl peroxide (10 mmols) were dissolved in 1 L of anhydrous carbon tetrachloride, and the mixture was stirred under reflux for 72 h. The mixture was cooled to RT and washed with water. The organic layer was drawn off, dried over anhydrous sodium sulfate, filtered and concentrated in vacuo to a dark oil. The crude mixture was dissolved in 500 ml of acetonitrile, then triphenylphosphine (200 mmols) was added and the mixture was refluxed under nitrogen overnight. It was then cooled to RT and diluted with anhydrous ether. The precipitated solid was collected by filtration, washed thoroughly with anhydrous ether and dried in vacuo overnight, yielding 25 g of a tan crystalline solid which showed a single spot by TLC (silica gel, 5% MeOH in DCM).

A Wittig reaction was then performed. Briefly, under anhydrous conditions, 0.738 g (1.68 mmol) 2-triphenylphosphoniumquinaldine bromide in dry THF was cooled to $-78°$ C. 1.0 ml (2.5 mmol, 2.5 M in hexanes) n-butyl lithium was slowly added, and this was allowed to react for 20 min. 0.301 g (1.68 mmol) 4-(N,N-dimethylamino)-2-methoxybenzaldehyde was then added. After a few minutes, the cold bath was removed, and this was left at ambient temp. for 18 h. The reaction was quenched by the addition of aq. sat. $NH_4Cl$. This was extracted with EtAc, and the organics washed with additional $NH_4Cl$, sat. $NaHCO_3$, and sat. NaCl. This was dried over anhydrous $Na_2SO_4$ and the solvent stripped on a rotavapor. After flash chromatography (3.8×18.0 cm; EtAc/Hep. (1:3); $R_f$ 0.29), 0.135 g (26% yield) of a red solid was obtained, mp=185–187° C. $^1$H NMR (CDCl$_3$) 8.04 (t, J=9.0, 2H), 7.94 (d, J=16.5, 1H), 7.74 (d, J=8.1, 1H), 7.73 (d, J=8.5, 1H), 7.66 (t of d, $J_t$=7.6, $J_d$=1.4, 1H), 7.61 (d, J=8.8, 1H), 7.43 (t of d, $J_t$=7.6, $J_d$=1.1, 1H), 7.29 (d, J=16.6, 1H), 6.37 (d of d, $J_1$=8.7, $J_2$=2.4, 1H), 6.22 (d, J=2.4, 1H), 3.93 (s, 3H), 3.03 (s, 6H). Anal. Calcd for $C_{20}H_{20}N_2O$: C, 78.92; H, 6.62; N, 9.20. Found:

C. Exemplary Compound 59-0209 was synthesized according to the procedure of McOmie, J. F. W.; and West, D. E., *Org Synth, Collect Vol V* (1973) 412. Under anhydrous conditions, 0.510 g (1.95 mmol) NNC 59-0198 was slowly treated with 0.38 ml (3.9 mmol) BBr$_3$ in dry CH$_2$Cl$_2$ at $-78°$ C. After 15 min, this was allowed to warm to RT. After 2 h, the reaction was re-cooled to $-78°$ C., and was then quenched by the addition of 1.6 ml (12 mmol) TEA in 25 ml MeOH. After 10 min, this was again allowed to warm to ambient temperature. After 1 h, this was concentrated to dryness on a rotavapor, and twice slurred in MeOH and re-stripped. Purification by flash chromatography (3.0×25.6 cm; EtAc/Hep. (1:2); $R_f$ 0.25) gave 0.20 g (41% yield) of a slightly yellow solid, mp=271–272° C. (dec.). $^1$H NMR (DMSO-d6) 9.77 (s, 1H), 8.31 (d, J=8.6, 1H), 7.96 (d, J=8.6, 1H), 7.92 (d, J=8.3, 1H), 7.82 (d, J=8.6, 1H), 7.74 (d, J=16.6, 1H), 7.72 (t, J=7.6, 1H), 7.58 (d, J=8.6, 2H), 7.53 (t, J=7.6, 1H), 7.26 (d, J=16.5, 1H), 6.83 (d, J=8.6, 2H). Anal. Calcd for $C_{17}H_{13}NO$: C, 82.57; H, 5.30; N, 5.66. Found:

D. Exemplary Compound 59-0019 was synthesized as follows: to a xylene solution of 2-methylquinoxaline (10 mmol) and 4-dimethylaminobenzaldehyde (10 mmol) was added piperdine (2 ml). The solution was heated at reflux for 1 day, at which time DBU (200 µL) was added and reflux continued for another 2 days. The solution was cooled to RT and extracted with 1 M citric acid. The aqueous phase was repeatedly extracted with ether. The organic phases were pooled, dried over Na$_2$SO$_4$, filtered and evaporated to dryness. The residue was chromatographed on silica gel. The product was eluted using 8:1:1 dicholormethane:ether: hexane. Fractions containing pure product were pooled and evaporated to dryness. The residue was triturated with ether and filtered to give the desired compound.

E. Exemplary Compound 59-0183 and related Compound 59-0182 were synthesized according to the following procedure. Briefly, quinaldic acid (0.5 mmol) and HATU (0.5 mmol) were dissolved in 2.5 mL of anhydrous DMF in a vial and the solution was stirred at room temperature (RT). Diisopropylethyamine (1 mmol) was added dropwise to the above stirred solution and the mixture was stirred for 15 min. The appropriate amine (0.5 mmol) was then added all at once to the above stirred mixture, and the mixture was stirred overnight at RT. It was then diluted with 25 mL of cold water with vigorous stirring, the precipitate was collected by filtration and washed thoroughly with water several times, and then dried in vacuo overnight. The product was purified by flash column chromatography over silica gel eluting with dichloromethane. The pure product was obtained as a tan powder.

F. Exemplary Compound 59-0209 was synthesized according to the following procedure. Under anhydrous conditions, 0.510 g (1.95 mmol) NNC 59-0198 was slowly treated with 0.38 ml (3.9 mmol) BBr$_3$ in dry CH$_2$Cl$_2$ at $-78°$ C. After 15 min, this was allowed to warm to RT. After 2 h, the reaction was re-cooled to $-78°$ C., and was then quenched by the addition of 1.6 ml (12 mmol) TEA in 25 ml MeOH. After 10 min, this was again allowed to warm to ambient temperature. After 1 h, this was concentrated to dryness on a rotavapor, and twice slurred in MeOH and re-stripped. Purification by flash chromatography (3.0×25.6 cm; EtAc/Hep. (1:2); $R_f$ 0.25) gave 0.20 g (41% yield) of a slightly yellow solid, mp=271–272° C. (dec.). $^1$H NMR (DMSO-d6) 9.77 (s, 1H), 8.31 (d, J=8.6, 1H), 7.96 (d, J=8.6, 1H), 7.92 (d, J=8.3, 1H), 7.82 (d, J=8.6, 1H), 7.74 (d, J=16.6, 1H), 7.72 (t, J=7.6, 1H), 7.58 (d, J=8.6, 2H), 7.53 (t, J=7.6, 1H), 7.26 (d, J=16.5, 1H), 6.83 (d, J=8.6, 2H). Anal. Calcd for $C_{17}H_{13}NO$: C, 82.57; H, 5.30; N, 5.66. Found:

G. Other embodiments wherein $AR^1$ is of formula (4a) can be synthesized as follows:

a. Quinoline azo compounds (59-0030 and 59-0078) may be prepared by reaction of 2-aminoquinoline with a nitrosobenzene (Brown, E. V., et al, *J Org Chem* (1961) 26:2831–33; Brown, E. V. *Mass Spectra of Some Phenylazopyridines and Quinolines* (1969) 6:571–73);

b. Azo derivatives may be obtained by reaction of 2-aminoquinolines with aldehydes, Morimoto, T., et al., *Chem Pharm Bull* (1977) 25:1607–09; Renault, J., et al., *Hebd Seances Acad Sci, Ser C* (1975) 280:1041–43; and Lugovkin, B. P.; *Zh Obshch Khim* (1972) 42:966–69.

c. Imino derivatives may be obtained by reaction of 2-formylquinolines with anilines, Tran Quoc Son, et al, (1983) 21:22–26; Hagen, V. et al. *Pharmazie* (1983)

38:437–39; and Gershuns, A. L., et al., *Tr Kom Anal Khim, Akad Nauk SSSR* (1969) 17:242–50.

d. Alternatively conjugated linkers can be formed by bromination of the olefin of 50-0197 with Br₂ in AcOH followed by elimination with DBU as set forth in Zamboni et al. *J Med Chem* (1992) 35:3832–44.

H. Analogs having the constrained linker depicted below:

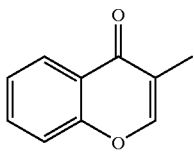

may be synthesized by reference to the methods described in Gorbulenko, N. V. et al. *Dokl Akad Nauk Ukr SSR* (1991) 5: 117–23, substituting the 6-membered heterocycle for benzothiazole.

Related, compounds having the constrained linker depicted below:

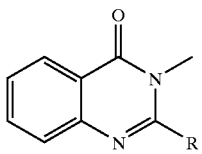

R = alkyl, OH may be synthesized by reference to the methods described in the following publications: Chaurasia, M. R. & Sharma, A. J. *Acta Cienc Indica Chem* (1992) 18:419–22; Kandeel, Maymona M., in *Phosphorus, Sulfur, Silicon, Relat Elem* (1990) 48:149–55; Salem, M. A. & Soliman, E. A. *Egypt J Chem* (1985) 27:779–87;Garin, J. et al. *Synthesis* (1984) 6:520–22, and Ayyangar N. R. et al. *Dyes and Pigments* (1990) 13:301–10.

I. Exemplary Compound 59-0145 can be synthesized according to the following method. Briefly, a mixture of 2-chloro-5-trifluoromethylpyridine (15 mmol), ethylenediamine (6 mmol), and diisopropylethylamine (18 mmol) was heated at reflux for 18 h. After cooling to room temperature, the solid mass was triturated with dichloromethane. The product was filtered and then suspended in hot EtOAc:CHCl₃ (50:50, 800 mL) and filtered to remove insoluble material. The volume was reduced to ~200 mL by heating on a steam bath. On standing, crystals of pure product were deposited.

Related compounds may be synthesized by reference to the method described for Compound 59-0145, and by reference to the methods described in the following publications: Tzikas, A.& Carisch, C., U.S. Pat. No. 5,393,306, issued Feb. 28, 1995; Herzig, P.& Andreoli, A., EP 580554, published Jan. 26, 1994; Pohlke, R. & Fischer, W., DE 3938561, published May 23, 1991. Analogs containing the structure O—(CH₂)ₙ—O may be synthesized by reference to the previous citations, as well as the following publications: Kawato, T. & Newkome, G. *Heterocycles* (1990) 31:1097–104; Kameko, C. & Momose, Y. *Synthesis* (1982) 6:465–66; Tomlin, C. D. S. et al., GB 1161492, published Aug. 13, 1969.

J. Exemplary Compound 59-0097 and exemplary Compound 59-0201 were synthesized according to the following general procedure. Briefly, the isothiocyanate or isocyanate (1 mmol) was dissolved in 5 mL of anhydrous DMF in a vial and the solution was stirred at room temperature (RT). Diisopropylethyamine (2 mmol) was added dropwise to the above stirred solution followed by 3-hydrazinobenzoic acid (1 mmol), and the mixture was stirred overnight at RT. It was then diluted with 50 mL of cold water with vigorous stirring. The precipitate was collected by filtration, washed thoroughly with water several times, and then dried in vacuo overnight. The product was purified by flash column chromatography over silica gel eluting with 5% methanol in dichloromethane. The pure product was obtained as a red to purple powder. The compounds of the invention are produced by substituting for at least one phenyl group the appropriate heterocycle.

K. Compounds of the class represented by exemplary Compound 59-0045 can be synthesized using standard procedures for the synthesis of phenyl hydrazones of aromatic aldehydes, as described in any organic textbook. The synthesis of exemplary Compound 59-0045 may be performed as follows. Briefly, a suspension of 3-hydrazinobenzoic acid (1 mmol), p-dimethylaminobenzaldehyde (1 mmol), and AcOH (50 µL) in EtOH:H₂O (4 mL:1 mL) was heated at 105° C. in a sealed vial for 3 h. After cooling, a bright yellow solid was removed by filtration. The solid was washed with cold MeOH and then with ether to give pure product.

L. Exemplary Compound 59-0096 and related, exemplary Compounds 59-0098, 59-0095, 59-0107, 59-0108, 59-0109, 59-0110 and 59-0200 may be synthesized according to the following general procedure. Briefly, the appropriate carboxylic acid (1 mmol) and HATU ([O-(7-azabenzotriazol-1-yl)-1,1,3,3-tritetramethyluronium hexafluorophosphate]; 1 mmol) were dissolved in 5 mL of anhydrous DMF in a vial and the solution was stirred at room temperature (RT). Disopropylethylamine (3 mmol) was added dropwise to the above stirred solution and the mixture was stirred for 15 min. 3-Hydrazinobenzoic acid (1 mmol) was then added all at once to the above stirred mixture and the mixture was stirred overnight at RT. It was then diluted with 50 mL of cold water with vigorous stirring and the precipitate was collected by filtration and washed thoroughly with water several times and then dried in vacuo overnight. The product was purified by flash column chromatography over silica gel eluting with 5–10% methanol in dichloromethane. The pure product was obtained as a tan crystalline solid.

M. Exemplary Compound 59-0097 and exemplary Compound 59-0201 were synthesized according to the following general procedure. Briefly, the isothiocyanate or isocyanate (1 mmol) was dissolved in 5 mL of anhydrous DMF in a vial and the solution was stirred at room temperature (RT). Diisopropylethyamine (2 mmol) was added dropwise to the above stirred solution followed by 3-hydrazinobenzoic acid (1 mmol), and the mixture was stirred overnight at RT. It was then diluted with 50 mL of cold water with vigorous stirring. The precipitate was collected by filtration, washed thoroughly with water several times, and then dried in vacuo overnight. The product was purified by flash column chromatography over silica gel eluting with 5% methanol in dichloromethane. The pure product was obtained as a red to purple powder.

N. Exemplary Compound 59-0125 where $R^1$ is methoxy, m is 1, the linker is azo and $Ar^2$ is di(2-hydroxyethyl)amino, and related compounds having an azo linker can be prepared in a manner similar to that described by Alberti, G. et al. *Chim Ind (Milan)* (1974) 56:495–97.

O. Exemplary Compound 59-0124 and related, constrained analogs having the structure depicted below:

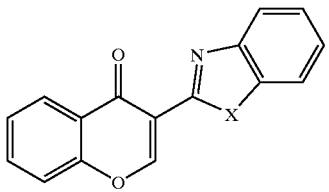

may be synthesized by reference to the methods described in Gorbulenko, N. V. et al. *Dokl Akad Nauk Ukr SSR* (1991) 5:117–23.

Related, constrained analogs having the structure depicted below:

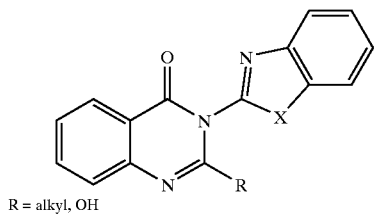

R = alkyl, OH may be synthesized by reference to the methods described in the following publications: Chaurasia, M. R. & Sharma, A. J. *Acta Cienc Indica Chem* (1992) 18:419–22; Kandeel, Maymona M., in *Phosphorus, Sulfur, Silicon, Relat Elem* (1990) 48:149–55; Salem, M. A. & Soliman, E. A. *Egypt J Chem* (1985) 27:779–87; Garin, J. et al. *Synthesis* (1984) 6:520–22, or according to the representative procedure described in Ayyangar N. R. et al. *Dyes and Pigments* (1990) 13:301–10.

What is claimed is:

1. A method to treat a condition in a vertebrate animal characterized by a deficiency in, or need for, bone growth or replacement and/or an undesirable level of bone resorption, which method comprises administering to a vertebrate subject in need of such treatment an effective amount of a compound of the formula (1):

Ar¹—L—Ar² wherein AR¹ is

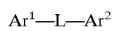

(9a)

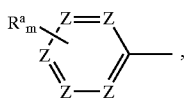

wherein
each $R^a$ is independently a noninterfering substituent;
m is an integer of 0–4;
each Z is independently N or CR, where R is H or alkyl (1–6C), with the proviso that at least one Z must be N and at least one Z must be CR;
L is a flexible conjugating or non-conjugating linker; and
wherein Ar² is a substituted or unsubstituted phenyl, substituted or unsubstituted naphthyl, substituted or unsubstituted aromatic system containing a 6-membered heterocycle or a substituted or unsubstituted aromatic system containing a 5-membered heterocycle.

2. The method of claim 1 wherein Ar² is

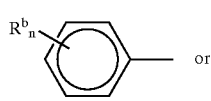

(v)

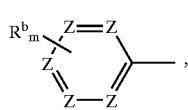

(vi)

wherein
each $R^b$ is independently a noninterfering substituent, and
in (vi) each Z is independently N or CR, where R is H or alkyl (1–6C), with the proviso that at least one Z must be a N and at least one Z must be CR.

3. The method of claim 2 wherein the compound of formula (1) is of the formula

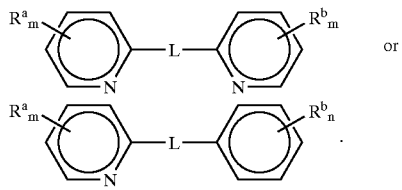

4. The method of claim 3 wherein L is —N═N—, —RC═CR—, —RC═N—, —NRCO—, —NRCR₂—, —NRCR₂CR₂—, —NRCR₂CO—, —NRNR—, —CR₂CR₂—, —NRCR₂CR₂NR—, —NRCR═CRNR— or —NRCOCR₂NR—, and/or
wherein each $R^a$ and $R^b$ is independently halo, OR, SR, NR₂, NO, NO₂, OCF₃ or CF₃ wherein R is H or alkyl (1–6C) or $R^b$ comprises an aromatic system and each m and n is independently 0, 1 or 2.

5. The method of claim 4 wherein L is —NHCR₂CR₂NH—, m is 1 and $R^a$ is CF₃ para to L.

6. The method of claim 5 wherein the compound of formula (1) is

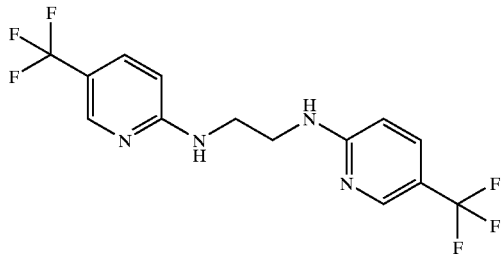

59-0145

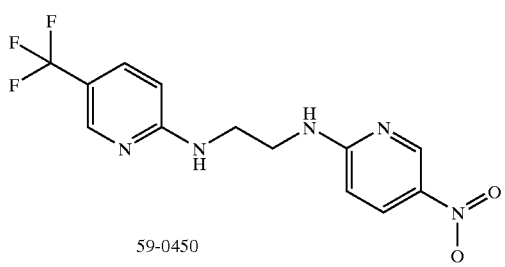

59-0450

-continued
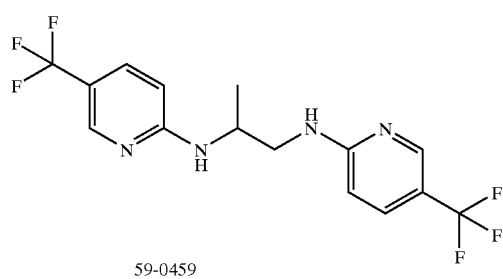
59-0459
or
-continued
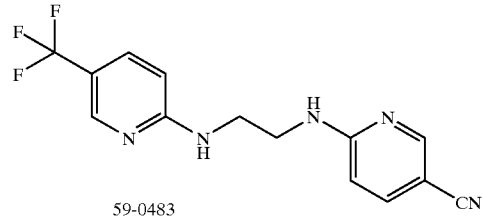
59-0483
\* \* \* \* \*